United States Patent
Edmunds et al.

(10) Patent No.: US 10,645,928 B2
(45) Date of Patent: May 12, 2020

(54) PESTICIDALLY ACTIVE POLYCYCLIC DERIVATIVES WITH SULFUR CONTAINING SUBSTITUENTS

(71) Applicant: Syngenta Participations AG, Basel (CH)

(72) Inventors: Andrew Edmunds, Stein (CH); Andre Jeanguenat, Stein (CH); Pierre Joseph Marcel Jung, Stein (CH); Michel Muehlebach, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/524,926

(22) PCT Filed: Oct. 30, 2015

(86) PCT No.: PCT/EP2015/075205
§ 371 (c)(1),
(2) Date: May 5, 2017

(87) PCT Pub. No.: WO2016/071214
PCT Pub. Date: May 12, 2016

(65) Prior Publication Data
US 2017/0318809 A1 Nov. 9, 2017

(30) Foreign Application Priority Data

Nov. 7, 2014 (EP) .................................. 14192265
Dec. 19, 2014 (EP) .................................. 14199338

(51) Int. Cl.
*A01N 43/50* (2006.01)
*C07D 417/14* (2006.01)
*C07D 417/04* (2006.01)
*C07D 487/04* (2006.01)

(52) U.S. Cl.
CPC ............ *A01N 43/50* (2013.01); *C07D 417/04* (2013.01); *C07D 417/14* (2013.01); *C07D 487/04* (2013.01)

(58) Field of Classification Search
None
See application file for complete search history.

(56) References Cited

U.S. PATENT DOCUMENTS

| 2010/0081812 A1* | 4/2010 | Smith ................. C07D 401/12 544/327 |
| 2017/0233389 A1* | 8/2017 | Jung .................... C07D 471/04 424/403 |
| 2017/0240554 A1* | 8/2017 | Edmunds ............... A01N 43/90 |
| 2017/0260182 A1* | 9/2017 | Edmunds ............. C07D 471/04 |
| 2017/0267672 A1* | 9/2017 | Stoller ................. C07D 417/10 |

FOREIGN PATENT DOCUMENTS

| WO | 2012086848 A1 | 6/2012 |
| WO | 2013191113 A1 | 12/2013 |
| WO | 2015000715 A1 | 1/2015 |

OTHER PUBLICATIONS

Patani, G. A. et al. "Bioisosterism: A rational approach in drug design" Chemical Reviews, 1996, 96(8) 3147-3176. (Year: 1996).*
Extended European Search Report for 12192265.8, dated Apr. 22, 2015.
International Search Report & Written Opinion for PCT/EP2015/075205, dated Dec. 23, 2015.
Patani, G.A. et al.: "Bioisosterism: A Rational Approach in Drug Design" in: Chemical Reviews, American Chemical Society, US, vol. 96, No. 8, 1996, pp. 3147-3176, XP000652176.

* cited by examiner

*Primary Examiner* — Erin E Hirt
(74) *Attorney, Agent, or Firm* — Baker & Hostetler, LLP; Toni-Junell Herbert

(57) ABSTRACT

Polycyclic Compounds of formula (I) wherein the substituents are as defined in claim 1, and the agrochemically acceptable salts, stereoisomers, enantiomers, tautomers and N-oxides of those compounds, can be used as insecticides and can be prepared in a manner known per se.

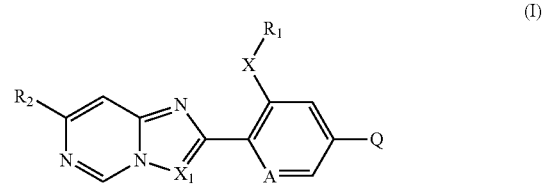

13 Claims, No Drawings

PESTICIDALLY ACTIVE POLYCYCLIC DERIVATIVES WITH SULFUR CONTAINING SUBSTITUENTS

RELATED APPLICATION INFORMATION

This application is a 371 of International Application No. PCT/EP2015/075205, filed 30 Oct. 2015, which claims priority to EP 14192265.8, filed 7 Nov. 2014, and EP 14199338.6, filed 19 Dec. 2014, the contents of which are incorporated herein by reference herein.

The present invention relates to pesticidally active, in particular insecticidally active polycyclic derivatives containing sulfur substituents, to intermediates for the preparation of those compounds, to compositions comprising those compounds, and to their use for controlling animal pests (including arthropods and in particular insects or representatives of the order Acarina).

Heterocyclic compounds with pesticidal action are known and described, for example, in WO 2012/086848 and WO 2013/018928.

There have now been found novel pesticidally active polycyclic ring derivatives with sulfur containing phenyl and pyridyl substituents.

The present invention accordingly relates to compounds of formula I,

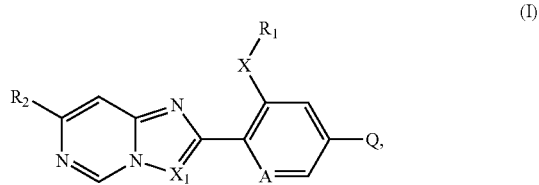

(I)

wherein

A is CH or N;

Q is phenyl which can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or Q is a five- to ten-membered monocyclic or fused bicyclic ring system linked via a carbon atom to the ring which contains the group A, said ring system can be aromatic, partially saturated or fully saturated and contains 1 to 4 hetero atoms selected from the group consisting of nitrogen, oxygen and sulfur, with the proviso that each ring system cannot contain more than 2 oxygen atoms and more than 2 sulfur atoms, said five- to ten-membered ring system can be mono- to polysubstituted by substituents independently selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or Q is a five- to six-membered, aromatic, partially saturated or fully saturated ring system linked via a nitrogen atom to the ring which contains the group A, said ring system can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; and said ring system contains 1, 2 or 3 heteroatoms selected from the group consisting of nitrogen, oxygen and sulfur, with the proviso that said ring system cannot contain more than one oxygen atom and more than one sulfur atom;

or Q is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$ haloalkyl, $C_3$-$C_6$cycloalkyl, and phenyl, whereby the phenyl group can be mono- or polysubstituted by substituents selected from the group consisting of halogen, cyano, hydroxycarbonyl, amidocarbonyl, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ halo-alkylsulfinyl, $C_1$-$C_4$ haloalkylsulfonyl and —C(O)$C_1$-$C_4$ haloalkyl;

or Q is $C_2$-$C_6$alkenyl, or $C_2$-$C_6$alkenyl mono- or polysubstituted by substituents selected from the group consisting of halogen, cyano, $C_1$-$C_4$alkyl, $C_1$-$C_4$ haloalkyl, $C_3$-$C_6$cycloalkyl and phenyl, whereby said phenyl group can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ halo-alkylsulfinyl, $C_1$-$C_4$ haloalkylsulfonyl and —C(O)$C_1$-$C_4$ haloalkyl;

or Q is $C_2$-$C_6$alkynyl, or $C_2$-$C_6$alkynyl mono- or polysubstituted by substituents selected from the group consisting of halogen, cyano, $C_1$-$C_4$alkyl, $C_1$-$C_4$ haloalkyl, $C_3$-$C_6$cycloalkyl, tri($C_1$-$C_4$alkyl)silyl and phenyl, whereby said phenyl group can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ halo-alkylsulfanyl, $C_1$-$C_4$ haloalkylsulfinyl, $C_1$-$C_4$ haloalkylsulfonyl and —C(O)$C_1$-$C_4$ haloalkyl;

or Q is a $C_1$-$C_4$alkyl, which can be mono- or polysubstituted by substituents selected from the group of halogen, cyano, $C_3$-$C_6$cycloalkyl, $C_1$-$C_4$ haloalkoxy, $C_1$-$C_4$alkoxy, $C_1$-$C_4$sulfanyl, $C_1$-$C_4$alkylsulfinyl, $C_1$-sulfonyl and —C(O)$C_1$-$C_4$alkyl;

X is S, SO or $SO_2$;

$R_1$ is $C_1$-$C_4$alkyl, $C_1$-$C_4$ haloalkyl, $C_3$-$C_6$cycloalkyl, $C_3$-$C_6$cycloalkyl-$C_1$-$C_4$alkyl; or $R_1$ is $C_3$-$C_6$cycloalkyl-$C_1$-$C_4$alkyl mono- or polysubstituted by substituents selected from the group consisting of halogen, cyano and $C_1$-$C_4$alkyl; or $R_1$ is $C_2$-$C_6$alkenyl, $C_2$-$C_6$ haloalkenyl or $C_2$-$C_6$alkynyl;

$R_2$ is halogen, cyano, $C_1$-$C_6$ haloalkyl or $C_1$-$C_6$ haloalkyl substituted by one or two substituents selected from the group consisting of hydroxyl, methoxy and cyano; or $R_2$ is $C_1$-$C_4$ haloalkylsulfanyl, $C_1$-$C_4$ haloalkylsulfinyl, $C_1$-$C_4$ haloalkylsulfonyl, O($C_1$-$C_4$ haloalkyl), or —C(O)$C_1$-$C_4$ haloalkyl; or $R_2$ is $C_3$-$C_6$cycloalkyl which can be mono- or polysubstituted by substituents selected from the group consisting of halogen, cyano and $C_1$-$C_4$alkyl;

$X_1$ is $CR_3$, wherein $R_3$ is hydrogen, $C_1$-$C_4$alkyl, $C_2$-$C_6$alkenyl, $C_2$-$C_6$alkynyl, $C_1$-$C_4$alkoxy-$C_1$-$C_4$alkyl or $C_3$-$C_6$cycloalkyl;

and agrochemically acceptable salts, stereoisomers, enantiomers, tautomer's and N-oxides of those compounds.

Compounds of formula I which have at least one basic centre can form, for example, acid addition salts, for example with strong inorganic acids such as mineral acids, for example perchloric acid, sulfuric acid, nitric acid, a phosphoric acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated. $C_1$-di-alkylamino is dimethylamino.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, methoxy, ethoxy, propoxy, i-propoxy, n-butoxy, isobutoxy, sec-butoxy and tert-butoxy and also the isomeric pentyloxy and hexyloxy radicals.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

The cycloalkyl groups preferably have from 3 to 6 ring carbon atoms, for example cyclopropyl, cyclobutyl, cyclopentyl and cyclohexyl.

In the context of this invention, examples of a five- to six-membered, aromatic, partially saturated or fully saturated ring system that are linked via a nitrogen atom to the ring which contains the group A, are pyrazole, pyrrole, pyrrolidine, pyrrolidine-2-one, piperidine, morpholine, imidazole, triazole and pyridine-2-one.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

The compounds of formula I according to the invention also include hydrates which may be formed during the salt formation.

In a preferred group of compounds of formula I,

Q is phenyl which can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or Q is a five- to ten-membered monocyclic or fused bicyclic ring system linked via a carbon atom to the ring which contains the group A, said ring system can be aromatic, partially saturated or fully saturated and contains 1 to 4 hetero atoms selected from the group consisting of nitrogen, oxygen and sulfur, with the proviso that each ring system cannot contain more than 2 oxygen atoms and more than 2 sulfur atoms, said five- to ten-membered ring system can be mono- to polysubstituted by substituents independently selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or Q is a five- to six-membered, aromatic, partially saturated or fully saturated ring system linked via a nitrogen atom to the ring which contains the group A, said ring system can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; and said ring system contains 1, 2 or 3 heteroatoms selected from the group consisting of nitrogen, oxygen and sulfur, with the proviso that said ring system cannot contain more than one oxygen atom and more than one sulfur atom;

or Q is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$ haloalkyl, $C_3$-$C_6$cycloalkyl, and phenyl, whereby the phenyl group can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ halo-alkylsulfinyl, $C_1$-$C_4$ haloalkylsulfonyl and —C(O)$C_1$-$C_4$ haloalkyl; or Q is $C_2$-$C_6$alkenyl, or $C_2$-$C_6$alkenyl mono- or polysubstituted by substituents selected from the group consisting of halogen, cyano, $C_1$-$C_4$alkyl, $C_1$-$C_4$ haloalkyl, $C_3$-$C_6$cycloalkyl and phenyl, whereby the phenyl group can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ halo-alkylsulfinyl, $C_1$-$C_4$ haloalkylsulfonyl and —C(O)$C_1$-$C_4$ haloalkyl; or Q is $C_2$-$C_6$alkynyl, or $C_2$-$C_6$alkynyl mono- or polysubstituted by substituents selected from the group consisting of halogen, cyano, $C_1$-$C_4$alkyl, $C_1$-$C_4$ haloalkyl, $C_3$-$C_6$cycloalkyl, tri($C_1$-$C_4$alkyl)silyl and phenyl, whereby the phenyl group can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ halo-alkylsulfanyl, $C_1$-$C_4$ haloalkylsulfinyl, $C_1$-$C_4$ haloalkylsulfonyl and —C(O)$C_1$-$C_4$ haloalkyl.

In a preferred embodiment of the invention a five- to ten-membered monocyclic or fused bicyclic hetero-ring system which can be aromatic, partially saturated or fully saturated and contains 1 to 4 hetero atoms selected from the group consisting of nitrogen, oxygen and sulfur, with the proviso that each ring system cannot contain more than 2 oxygen atoms and more than 2 sulfur atoms or a three- to ten-membered, monocyclic or fused bicyclic ring system which may be aromatic, partially saturated or fully saturated; is selected from the group consisting of pyrrolyl, pyrazolyl, isoxazolyl, furanyl, thienyl, imidazolyl, oxazolyl, thiazolyl, isothiazolyl, triazolyl, oxadiazolyl, thiadiazolyl, tetrazolyl, furyl, pyridyl, pyrimidyl, pyrazinyl, pyridazinyl, triazinyl, pyranyl, quinazolinyl, isoquinolinyl, indolizinyl, isobenzofuranylnaphthyridinyl, quinoxalinyl, cinnolinyl, phthalazinyl, benzothiazolyl, benzoxazolyl, benzotriazolyl, indazolyl, indolyl, (1H-pyrrol-1-yl), (1H-pyrrol-2-yl)-, (1H-pyrrol-3-yl), (1H-pyrazol-1-yl), (1H-pyrazol-3-yl), (3H-pyrazol-3-yl), (1H-pyrazol-4-yl)-, (3-isoxazolyl)-, (5-isoxazolyl)-, (2-furanyl)-, (3-furanyl)-, (2-thienyl)-, (3-thienyl)-, (1H-imidazol-2-yl)-, (1H-imidazol-4-yl)-, (1H-imidazol-5-yl)-, (2-oxazol-2-yl)-, (oxazol-4-yl)-, (oxazol-5-yl)-, (thiazol-2-yl)-, (thiazol-4-yl)-, (thiazol-5-yl)-, (isothiazol-3-yl)-, (isothiazol-5-yl)-, (1H-1,2,3-triazol-1-yl)-, (1H-1,2,4-triazol-3-yl)-, (4H-1,2,4-triazol-4-yl)-, (1H-1,2,4-triazol-1-yl)-(1,2,3-oxadiazol-2-yl)-, (1,2,4-oxadiazol-3-yl)-, (1,2,4-oxadiazol-4-yl), (1,2,4-oxadiazol-5-yl)-, (1,2,3-thiadiazol-2-yl)-, (1,2,4-thiadiazol-3-yl)-, (1,2,4-thiadiazol-4-yl)-, (1,3,4-thiadiazol-5-yl)-, (1H-tetrazol-1-yl)-, (1H-tetrazol-5-yl), (2H-tetrazol-5-yl)-, (2-pyridyl)-, (3-pyridyl)-, (4-pyridyl)-, (2-pyrimidinyl)-, (4-pyrimidinyl)-, (5-pyrimidinyl)-, (2-pyrazinyl)-, (3-pyridazinyl)-, (4-pyridazinyl)-, (1,3,5-triazin-2-yl)-, (1,2,4-triazin-5-yl), (1,2,4-triazin-6-yl)-, (1,2,4-triazin-3-yl)-, (furazan-3-yl)-, (2-quinolinyl)-, (3-quinolinyl)-, (4-quinolinyl)-, (5-quinolinyl)-, (6-quinolinyl)-, (3-isoquinolnyl)-, (4-isoquinolnyl)-, (2-quinozolinyl)-, (2-quinoxalinyl)-, (5-quinoxalinyl)-, (pyrido[2,3-b]pyrazin-7-yl), (benzoxazol-5-yl)-, (benzothiazol-5-yl)-, (benzo[b]thien-2-yl)- and (benzo[1,2,5]oxadiazol-5-yl), indolinyl and tetrahydroquinolynyl.

Preferably Q is phenyl which can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or Q is a five- to ten-membered monocyclic or fused bicyclic ring system linked via a carbon atom to the ring which contains the group A, said ring system can be aromatic, partially saturated or fully saturated and contains 1 to 4 hetero atoms selected from the group consisting of nitrogen, oxygen and sulfur, with the proviso that each ring system cannot contain more than 2 oxygen atoms and more than 2 sulfur atoms, said five- to ten-membered ring system can be mono- to polysubstituted by substituents independently selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or Q is a five- to six-membered, aromatic, partially saturated or fully saturated ring system linked via a nitrogen atom to the ring which contains the group A, said ring system can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; and said ring system contains 1, 2 or 3 heteroatoms selected from the group consisting of nitrogen, oxygen and sulfur, with the proviso that said ring system cannot contain more than one oxygen atom and more than one sulfur atom.

In preferred compounds of formula I, Q is selected from the group consisting of J-1 to J-47:

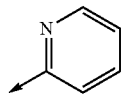
J-1

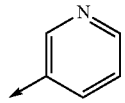
J-2

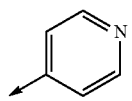
J-3

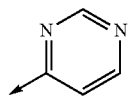
J-4

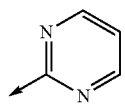
J-5

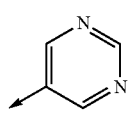
J-6

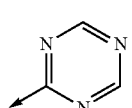
J-7

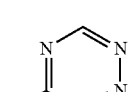
J-8

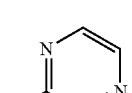
J-9

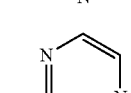
J-10

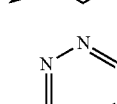
J-11

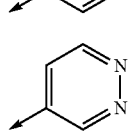
J-12

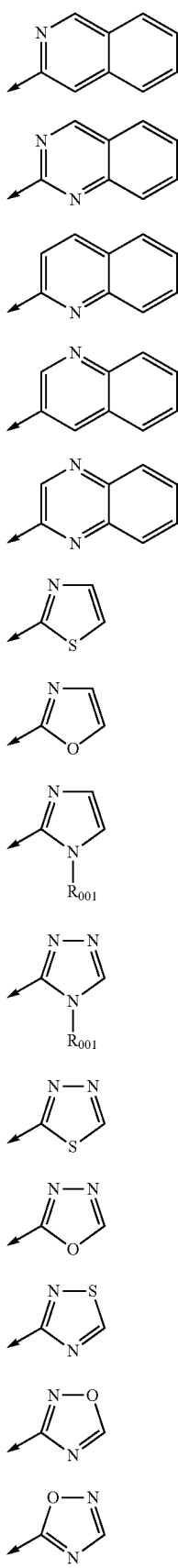
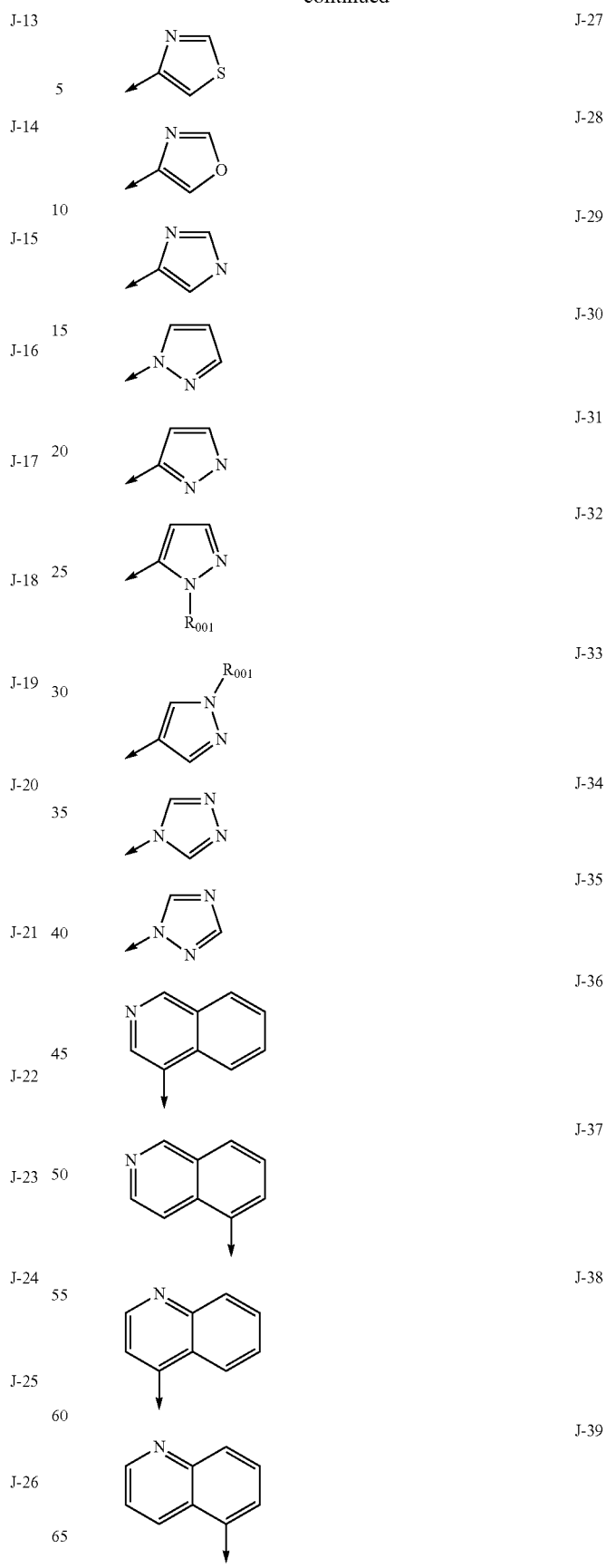

-continued

J-40
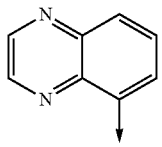

J-41
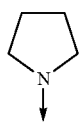

J-42
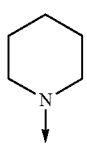

J-43

J-44

J-45

J-46

J-47
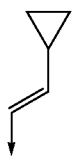

wherein each group J-1 to J-47 is mono- di- or trisubstituted with Rx, wherein each Rx is, independently selected from the group consisting of hydrogen, halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$ haloalkylsulfinyl, $C_1$-$C_4$ haloalkylsulfonyl and —C(O)$C_1$-$C_4$ haloalkyl, and $R_{001}$ is hydrogen or $C_1$-$C_2$alkyl, preferably hydrogen.

A further preferred group of compounds of formula I is represented by the compounds of formula I-1

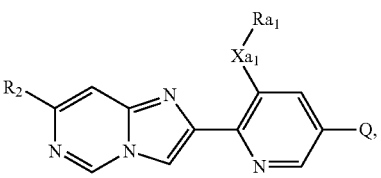

(I-1)

wherein $R_2$ and Q are as defined under formula I above; and wherein $Xa_1$ is S, SO or $SO_2$; $Ra_1$ is methyl, ethyl, n-propyl, i-propyl or cyclopropylmethyl; and agrochemically acceptable salts, stereoisomers, enantiomers, tautomers and N-oxides of those compounds. In this preferred group of compounds of formula I-1, $R_2$ is preferably $C_1$-$C_4$ haloalkyl, $Xa_1$ is preferably $SO_2$ and $Ra_1$ is preferably ethyl. In this preferred group of compounds of formula I, Q is selected from the group consisting of J-1 to J-47, more preferably J-1 to J42 (where the arrow represents the pount of attachment of the substituents to the radical Q):

J-1
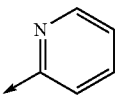

J-2
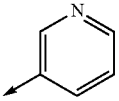

J-3
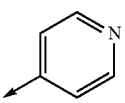

J-4
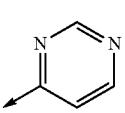

J-5
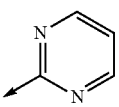

J-6
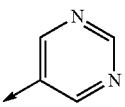

J-7
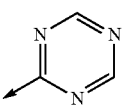

J-8
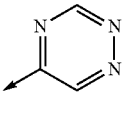

J-9
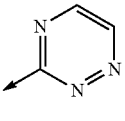

-continued
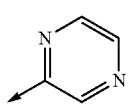
J-10
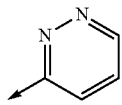
J-11
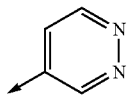
J-12
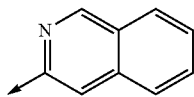
J-13
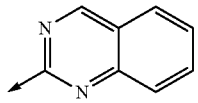
J-14
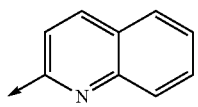
J-15
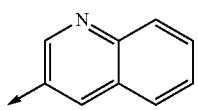
J-16
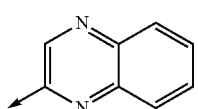
J-17
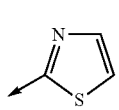
J-18
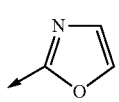
J-19
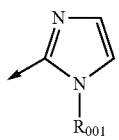
J-20
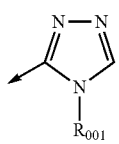
J-21
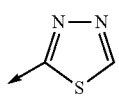
J-22
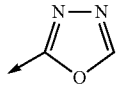
J-23
-continued
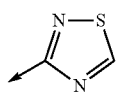
J-24
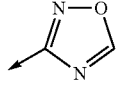
J-25
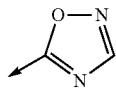
J-26
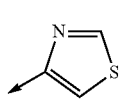
J-27
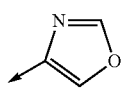
J-28
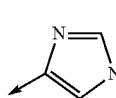
J-29
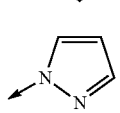
J-30
J-31
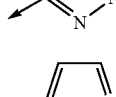
J-32
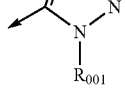
J-33
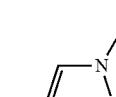
J-34
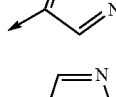
J-35
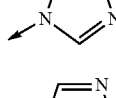
J-36
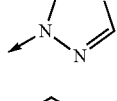
J-37

-continued

J-38 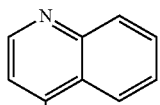

J-39 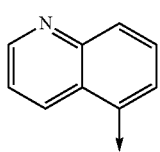

J-40 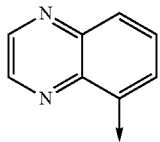

J-41 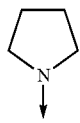

J-42 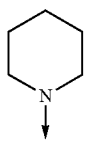

J-43 

J-44 

J-45 

J-46 

J-47 

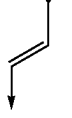

wherein each group J-1 to J-47 is mono- di- or trisubstituted with Rx, wherein each Rx is, independently selected from the group consisting of hydrogen, halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl, and $R_{001}$ is $C_1$-$C_2$alkyl. In another embodiment of the invention, $R_{001}$ is hydrogen.

A further preferred group of compounds of formula I is represented by the compounds of formula I-2

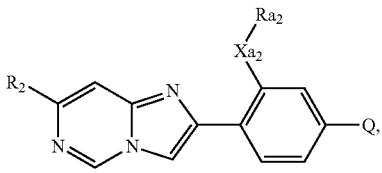
(I-2)

wherein $R_2$ and Q are as defined under formula I above; and wherein $Xa_2$ is S, SO or $SO_2$; $Ra_2$ is methyl, ethyl, n-propyl, i-propyl or cyclopropylmethyl; and agrochemically acceptable salts, stereoisomers, enantiomers, tautomers and N-oxides of those compounds. In this preferred group of compounds of formula I-2, $R_2$ is preferably $C_1$-$C_4$ haloalkyl, $Xa_2$ is preferably $SO_2$ and $Ra_2$ is preferably ethyl.

Especially preferred compounds of formula I are represented by the compounds of formula Ia-1

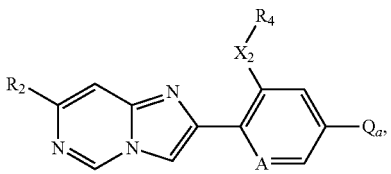
(Ia-1)

wherein

A is CH or N;

$X_2$ is S or $SO_2$;

$R_4$ is $C_1$-$C_4$alkyl;

$R_6$ is $C_1$-$C_4$ haloalkyl; and $Q_a$ is selected from the group consisting of the substituents

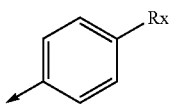
J-0a

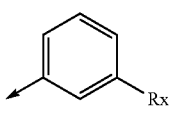
J-0b

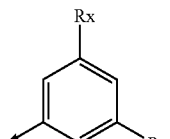
J-0c

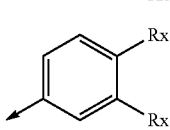
J-0d

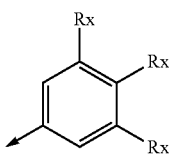
J-0e

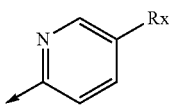
J-1a

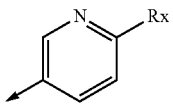
J-2a

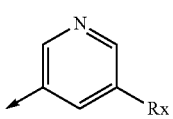
J-2b

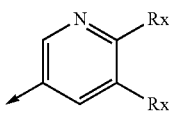
J-2c

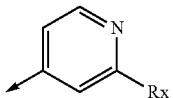
J-3a

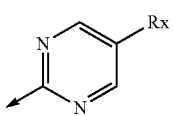
J-5a

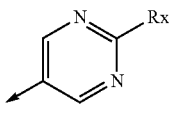
J-6a

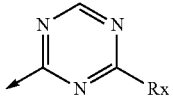
J-7a

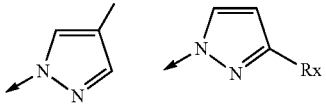
J-33a

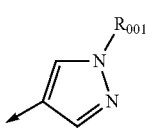
J-41a

J-43a

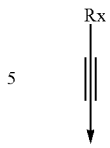
J-44a

J-45a

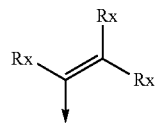
J-46a

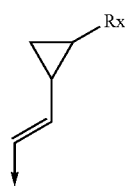
J-47a wherein each preferred group $Q_a$ is mono- di- or trisubstituted with Rx, wherein each Rx is, independently selected from the group consisting of hydrogen, halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ alkylsulfanyl, $C_1$-$C_4$ alkylsulfinyl, $C_1$-$C_4$ alkylsulfonyl, —C(O)$C_1$-$C_4$ alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl.

In said preferred compounds of formula Ia-1, $Q_a$ is preferably mono- or disubstituted with Rx, whereby each Rx is, independently preferably selected from the group consisting of hydrogen, halogen, $C_1$-$C_4$ alkyl, $C_1$-$C_4$ haloalkyl, $C_1$-$C_4$ alkoxy and $C_1$-$C_4$ haloalkoxy, and $R_{001}$ is hydrogen or $C_1$-$C_2$ alkyl, preferably $R_{001}$ is $C_1$-$C_2$ alkyl. In another embodiment of the invention, in formula Ia-1, $R_{001}$ is hydrogen. In particular preferred compounds, $Q_a$ is selected from the group consisting of the substituents

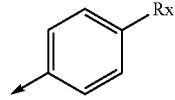
J-0a

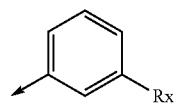
J-0b

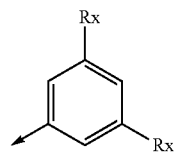
J-0c

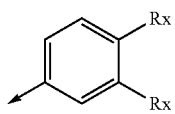 J-0d
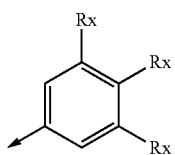 J-0e
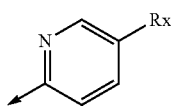 J-1a
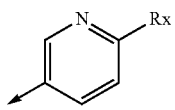 J-2a
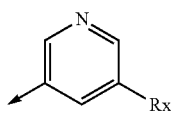 J-2b
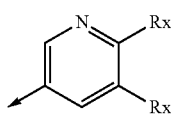 J-2c
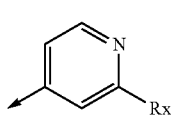 J-3a
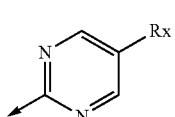 J-5a
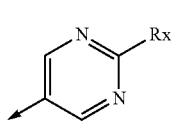 J-6a
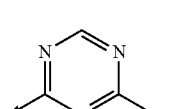 J-7a
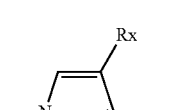 J-30a
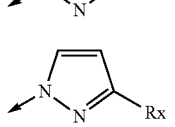 J-30b
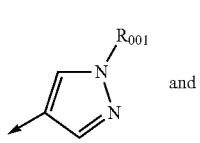 J-33a and
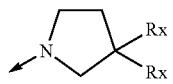 J-41a
Even more preferred compounds of formula I are represented by the compounds of formula Ia-2
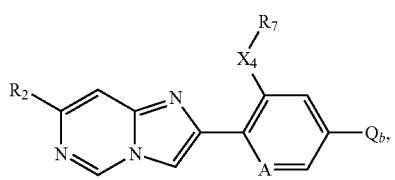 (Ia-2)
wherein
A is CH or N;
$X_4$ is $SO_2$;
$R_7$ is $C_1$-$C_4$ alkyl;
$R_8$ is $C_1$-$C_4$ haloalkyl; and
$Q_b$ is preferably selected from the group consisting of the substituents
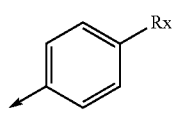 J-0a
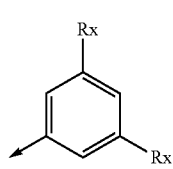 J-0c
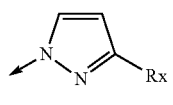 J-30b
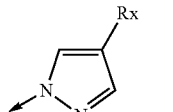 J-30a
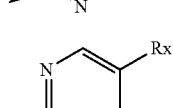 J-5a
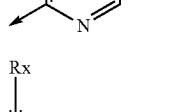 J-44a
and
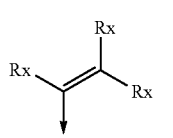 J-46c -continued

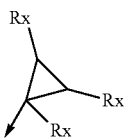
J-43c wherein each Rx is, independently selected from the group consisting of hydrogen, halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl. In highly preferred compounds $Q_b$ is selected from the group consisting of the substituents

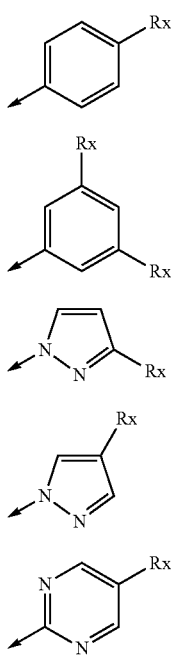

J-0a

J-0c

J-30b

J-30a

J-5a

In said preferred compounds of formula Ia-2, Rx is especially selected from the group consisting of hydrogen, cyano, halogen, $C_1$-$C_4$alkyl, $C_1$-$C_4$ haloalkyl, $C_1$-$C_4$alkoxy and $C_1$-$C_4$ haloalkoxy; in particular from hydrogen, halogen, $C_1$-$C_4$alkyl, $C_1$-$C_4$ haloalkyl, $C_1$-$C_4$alkoxy and $C_1$-$C_4$ haloalkoxy. An especially preferred group of compounds of formula I are represented by the compounds of formula Ia-3

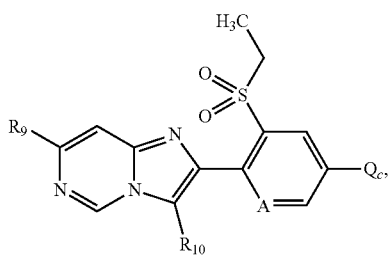
(Ia-3)

wherein
A is CH or N;
$R_9$ is $C_1$-$C_4$ haloalkyl;
$R_{10}$ is hydrogen or $C_1$-$C_2$alkyl, and $Q_c$ is selected from the group consisting of the substituents

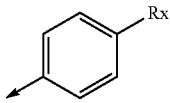
J-0a

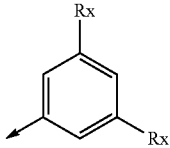
J-0c

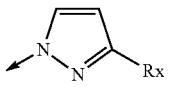
J-30b

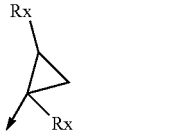
J-43c

J-44a

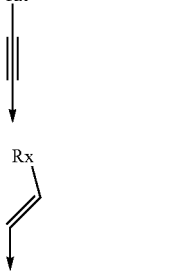
J-46c wherein Rx is selected from the group consisting of hydrogen, halogen, cyano, $C_1$-$C_4$alkyl, $C_1$-$C_4$ haloalkyl, $C_1$-$C_4$alkoxy and $C_1$-$C_4$ haloalkoxy, in particular hydrogen, halogen, $C_1$-$C_4$alkyl, $C_1$-$C_4$ haloalkyl, $C_1$-$C_4$alkoxy and $C_1$-$C_4$ haloalkoxy. In said preferred compounds of formula Ia-3, Rx is preferably independently selected from the group consisting of hydrogen, cyano, $C_1$-$C_4$ haloalkyl and halogen.

In each of the compounds of formula I-1, I-2, Ia-1 and Ia-2, Q is most preferably J-0a, J-0c, J-30b, or J43c

J-0a

J-0c

J-30b

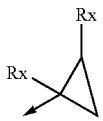

J-43c wherein Rx is hydrogen, halogen, cyano, or $C_1$-$C_4$alkyl, $C_1$-$C_4$ haloalkyl.

In outstanding compounds of formula I,
$X_1$ is CH;
X is $SO_2$;
A is CH or N;
$R_1$ is $C_1$-$C_4$alkyl;
$R_2$ is $C_1$-$C_4$ haloalkyl; and
Q is pyrazolyl, which can be mono-substituted by $C_1$-$C_4$ haloalkyl, or is phenyl which can be mono- or di-substituted by substituents selected from the group consisting of $C_1$-$C_4$ haloalkyl, halogen, $C_1$-$C_4$alkylsulfanyl, cyano and $C_1$-$C_4$ haloalkoxy; or is pyrimidinyl; or is $C_3$-$C_6$cycloalkyl which can be mono-substituted by cyano; or is $C_2$-$C_6$alkenyl; or is $C_1$-$C_4$ haloalkyl which can be substituted by cyano.

The process according to the invention for preparing compounds of formula I is carried out by methods known to those skilled in the art. Compounds of formula I, wherein $R_2$, $R_1$, X, $X_1$, A and Q are as defined in formula I, can be prepared (as shown in scheme 1) by a Suzuki reaction, which involves for example, reacting compounds of formula II, wherein $Xb_1$ is a leaving group like, for example, chlorine, bromine or iodine, or an aryl- or alkylsulfonate such as trifluoromethanesulfonate with compounds of formula IIIa, wherein $Y_{b1}$ can be a boron-derived functional group, as for example $B(OH)_2$ or $B(OR_{b1})_2$ wherein $R_{b1}$ can be a $C_1$-$C_4$alkyl group or the two groups $OR_{b1}$ can form together with the boron atom a five membered ring, as for example a pinacol boronic ester. The reaction can be catalyzed by a palladium based catalyst, for example tetrakis(triphenylphosphine)-palladium or (1,1'bis(diphenylphosphino)-ferrocene)dichloropalladium-dichloromethane (1:1 complex), in presence of a base, like sodium carbonate or cesium fluoride, in a solvent or a solvent mixture, like, for example a mixture of 1,2-dimethoxyethane and water or of dioxane and water, preferably under inert atmosphere. The reaction temperature can preferentially range from ambient temperature to the boiling point of the reaction mixture. Such Suzuki reactions are well known to those skilled in the art and have been reviewed, for example *J. Orgmet. Chem.* 576, 1999, 147-168.

Scheme 1:

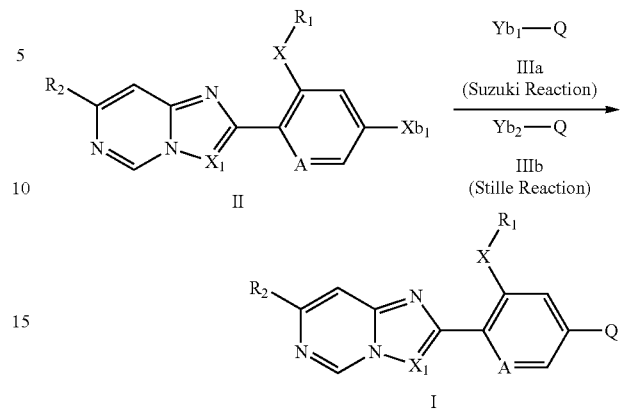

Alternatively compounds of formula I can be prepared by a Stille reaction of compounds of formula IIIb wherein $Y_{b2}$ is a trialkyl tin derivative, preferably tri-n-butyl tin, with compounds of formula II. Such Stille reactions are usually carried out in the presence of a palladium catalyst, for example tetrakis(triphenylphosphine)palladium(0), or (1,1'bis(diphenylphosphino)-ferrocene)dichloropalladium-dichloromethane (1:1 complex), in an inert solvent such as DMF, acetonitrile, or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example *J. Org. Chem.,* 2005, 70, 8601-8604, *J. Org. Chem.,* 2009, 74, 5599-5602, and *Angew. Chem. Int. Ed.,* 2004, 43, 1132-1136.

Compounds of formula I wherein Q is a nitrogen bearing heterocyclic system, and X, $X_1$, $R_1$, $R_2$ and A are as defined in formula I, can be prepared from compounds of formula II, wherein X, $X_1$, $R_1$, $R_2$ and A are as defined in formula I, and $Xb_1$ is a leaving group such as chlorine, bromine or iodine, or an aryl- or alkylsulfonate such as trifluoromethanesulfonate by reacting the heterocycle Q (which contains a an appropriate NH functionality), in the presence of a base, such as $K_2CO_3$ or $Cs_2CO_3$, optionally in the presence of a copper catalyst, for example copper (I) iodide in an inert solvent such as N-methyl pyrollidone or DMF at temperatures between 30-150° C. The reaction is illustrated for the heterocycle J-30b in scheme 2, which gives compounds of formula Iaa, wherein $R_2$, $R_1$, X, $X_1$, A and $R_x$ are as previously defined.

Scheme 2

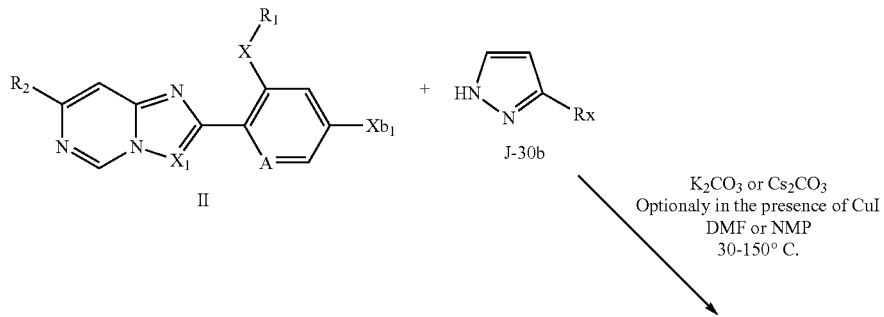

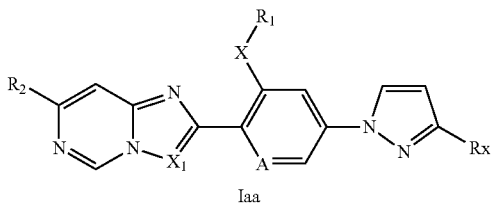

Iaa

Compounds of formula I can also be prepared (as depicted in scheme 3) by a Suzuki reaction as described above, which involves reacting compounds of formula IV with compounds of formula V, wherein $X_{b2}$ can be a halogen, preferentially chlorine, bromine or iodine, or a sulfonate, like for example a trifluoromethanesulfonate and $Y_{b3}$ can be a boron-derived functional group, as for example $B(OH)_2$ or $B(OR_{b2})_2$ wherein $R_{b2}$ can be a $C_1$-$C_4$alkyl group or the two groups $OR_{b2}$ can form together with the boron atom a five membered ring, as for example a pinacol boronic ester. In formula IV, A, $X_1$, $R_1$, $R_2$, and X are as described in formula I. The reaction can be catalyzed by a palladium based catalyst, for example tetrakis(triphenylphosphine)-palladium, in presence of a base, like sodium carbonate, in a solvent or a solvent mixture, like, for example a mixture of 1,2-dimethoxyethane and water, preferably under inert atmosphere. The reaction temperature can preferentially range ambient temperature to the boiling point of the reaction mixture.

or tert-butylhydroperoxide, or an inorganic oxidant, like a monoperoxo-disulfate salt or potassium permanganate. In a similar way, compounds of formula I-b2, wherein A, $R_1$, $R_2$, and $X_1$ have the values defined in formula I, and X is —SO—, can be prepared by oxidation of compounds of formula I-b1, wherein A, $R_1$, $R_2$, $X_1$ and Q have the values defined in formula I, and X is —S—, under analogous conditions described above. These reactions can be performed in various organic or aqueous solvents compatible to these conditions, by temperatures from below 0° C. up to the boiling point of the solvent system. The transformation of compounds of the formula I-b1 into compounds of the formula I-b2 and 1-b3 is represented in scheme 4. The reactions can occur in a stepwise fashion through compounds of formula I-b2. Those skilled in the art will appreciate that is therefore possible to control the reaction (depending on amount of oxidant added, the temperature, and time of reaction) to allow isolation of compounds of formula I-b2.

Scheme 3

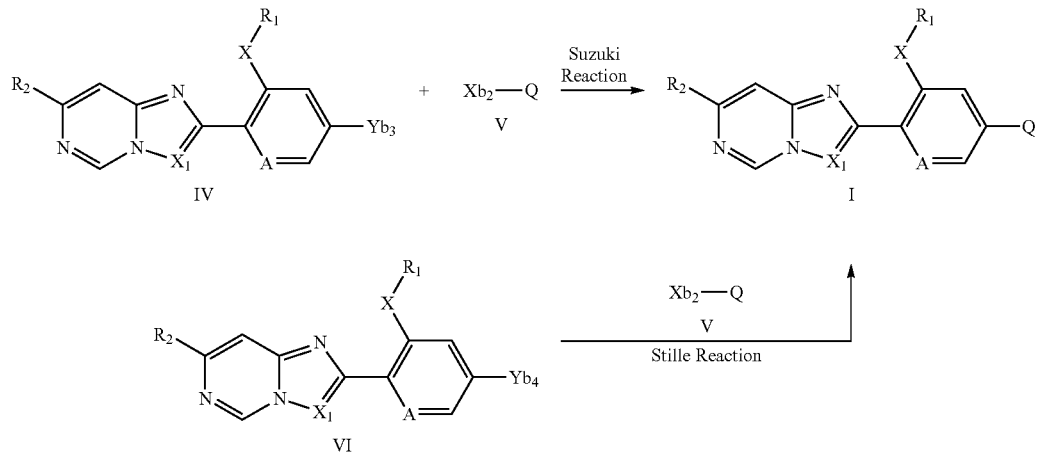

In a similar manner, compounds of formula I can be prepared by a Stille coupling (Scheme 3) of compounds of formula V with compounds of formula VI, wherein $R_1$, $R_2$, $X_1$, A, X are as described above, and $Y_{b4}$ is a trialkyl tin derivative, preferably tri-n-butyl tin, under conditions described as in scheme 1.

Compounds of formula I-b3, wherein A, $R_1$, $R_2$, $X_1$ and Q have the values defined in formula I, and X is —$SO_2$—, can be prepared by oxidation of compounds of formula I-b2, wherein A, $R_1$, $R_2$, and $X_1$ have the values defined in formula I, and X is —SO— (as shown in scheme 4) The reaction can be performed with reagents like, for example, a peracid such as peracetic acid or m-chloroperbenzoic acid, or a hydroperoxide, such as for example, hydrogen peroxide Compounds of formula I-b1 may be prepared (scheme 4) by reacting a compound of the formula VII with a compound of the formula VIIIa, wherein A, $R_1$, $R_2$, and $X_1$ have the values defined in formula I and X is sulfur and M is a metal or non-metal cation. In scheme 4, the cation M is assumed to be monovalent, but polyvalent cations associated with more than one S—$R_1$ group can also be considered. Preferred cations are, for example lithium, sodium, potassium or cesium. For this transformation to work, $Xb_3$ is a leaving group like, for example, fluorine, chlorine, bromine or iodine, or an aryl- or alkylsulfonate, but many other leaving groups could be considered (for example $NO_2$). The reaction can be performed in a solvent, preferably aprotic, at temperatures below 0° C. or up to boiling temperature of the reaction mixture.

Scheme 4

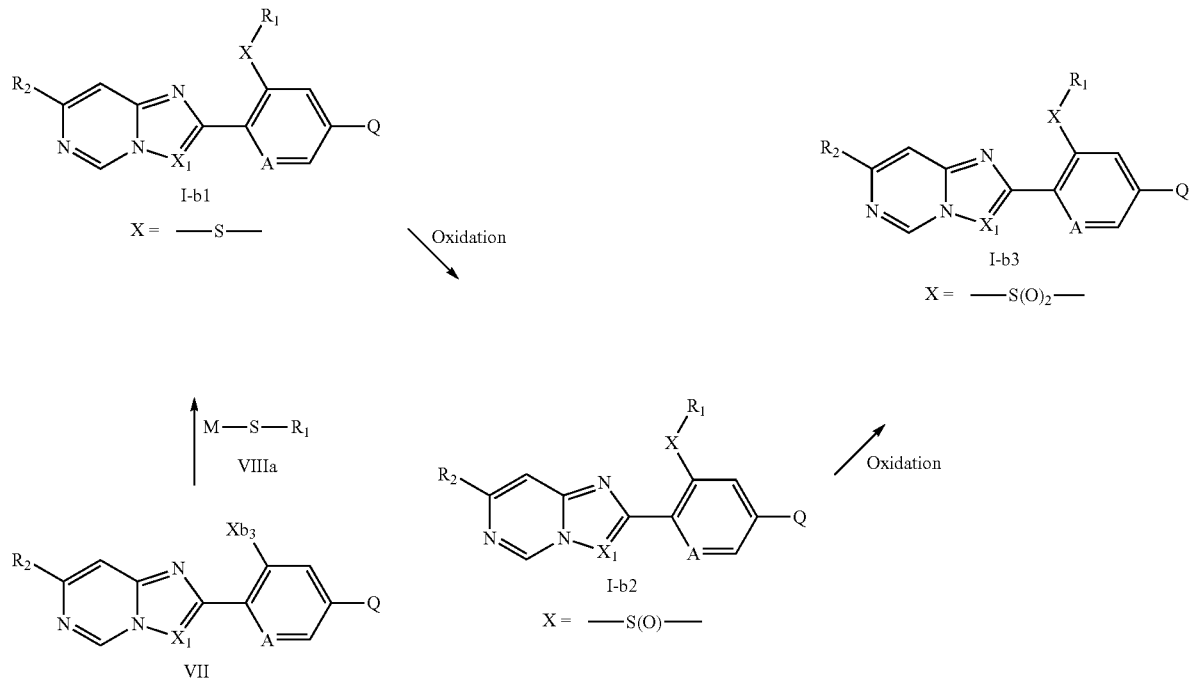

Compounds of formula VII, wherein $Xb_3$ is a leaving group like, for example, fluorine, chlorine, bromine iodine, or an aryl- or alkylsulfonate such as trifluoromethanesulfonate, or any other similar leaving group, can be prepared (scheme 5) by reacting compounds of formula V with compounds of formula VIII, wherein $X_{b3}$ can be a halogen, preferentially chlorine, bromine or iodine, or a sulfonate, like for example a trifluoromethanesulfonate, most preferably bromine or iodine and $Y_{b5}$ can be a boron-derived functional group, as for example $B(OH)_2$ or $B(OR_{b4})_2$ thoxyethane and water, preferably under inert atmosphere. The reaction temperature can preferentially range from ambient temperature to the boiling point of the reaction mixture. In a similar manner, compounds of formula VII can be prepared from compounds of formula X, wherein A, $X_1$, $R_2$, and $X_{b3}$ are as previously defined, and $Y_{b6}$ is a trialkyl tin derivative, preferably tri-n-butyl tin, with compounds of formula V, under conditions described for those described for the chemistry illustrated in scheme 1.

Scheme 5

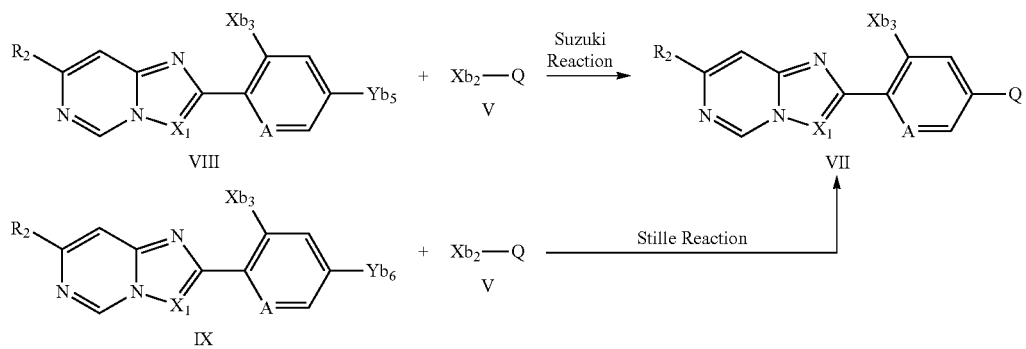

wherein $R_{b4}$ can be a $C_1$-$C_4$alkyl group or the two groups $OR_{b4}$ can form together with the boron atom a five membered ring, as for example a pinacol boronic ester. In formula VIII and V, A, $X_1$, $R_2$, and Q are as described in formula I. The reaction can be catalyzed by a palladium based catalyst, for example tetrakis(triphenylphosphine)-palladium, in presence of a base, like sodium carbonate, in a solvent or a solvent mixture, like, for example a mixture of 1,2-dime- In an alternative way, depicted in scheme 6, compounds of formula VII can also be prepared by reacting compounds of formula X, wherein $Xb_3$ and $Xb_4$ are leaving groups, for example, fluorine, chlorine, bromine or iodine, or an aryl- or alkylsulfonate such as trifluoromethanesulfonate, or any other similar leaving group, with compounds of formula IIIa (Suzuki reaction) or IIIb (Stille reaction). The chemistry is carried out analogously to that discussed for scheme 1.

Scheme 6

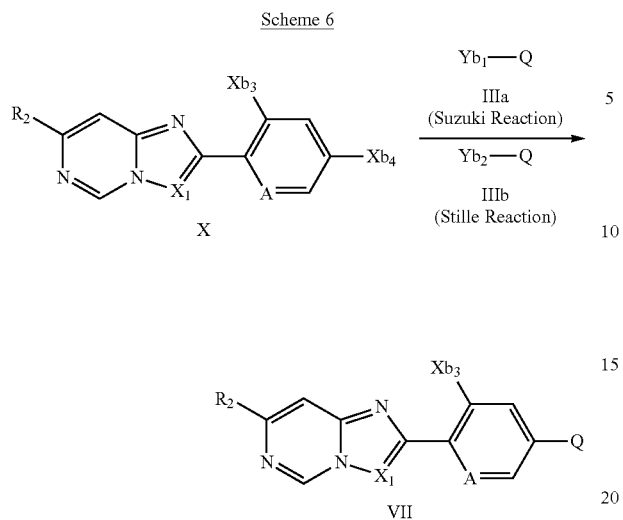

Scheme 8

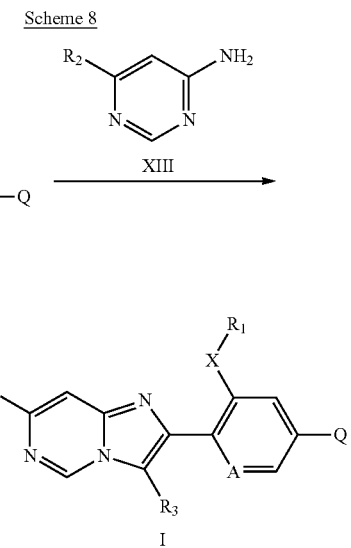

A further route to prepare compounds of formula II, respectively II-c1, involves reaction of compounds of formula X with compounds of formula VIIIa as shown in scheme 7.

Scheme 7:

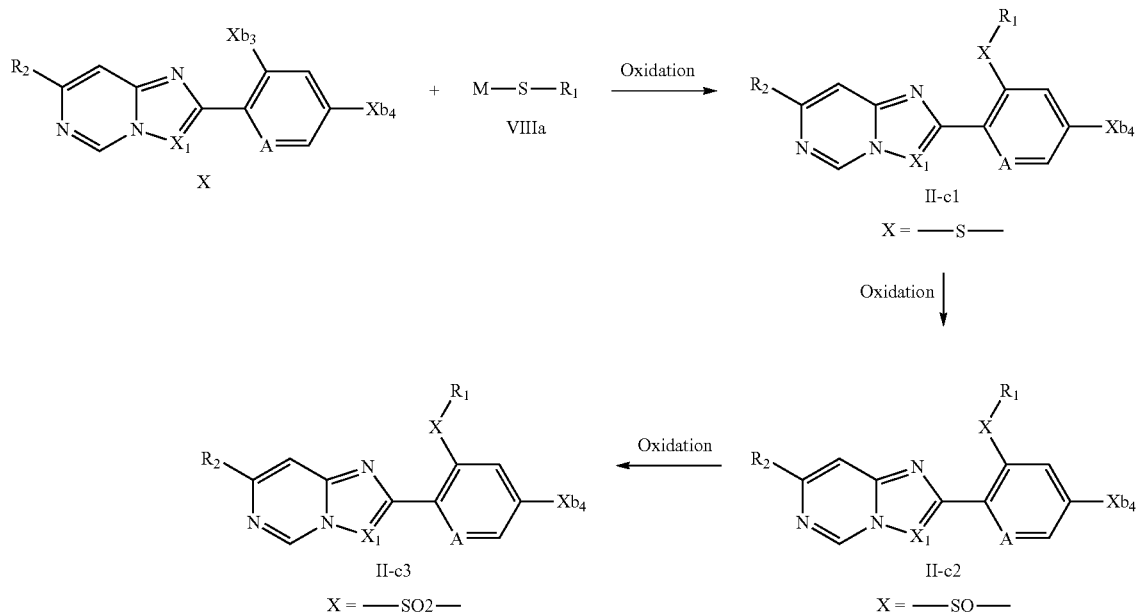

In scheme 7, compounds of formula X are reacted with compounds of formula VIIIa to give compounds of formula II-c1 according the conditions described in scheme 4 (which depending on conditions known to those skilled in the art will generate compounds of the formulas II-c2 and II-c3. It is particularly preferred to have compounds of formula X with Xb3 is fluorine or nitro in such reactions to allow selective introduction of the group —SR$_1$.

Compounds of formula I can be also prepared according to the chemistry shown in scheme 8:

In scheme 8, compounds of formula XIII, wherein R$_2$ is as described in formula I, are reacted with compounds of formula XII, wherein Xb6 is a halogen and Q, X, A, R$_1$ and R$_3$ are as defined above, in an inert solvent, for example ethanol or acetonitrile, optionally in the presence of a suitable base at temperatures between 80-150° C., to give compounds of formula I. The reaction may optionally be carried out in a microwave optionally in a micro wave, to give compounds of formula I. Such reactions are well described in the literature, for example WO 2012/49280 or WO 03/031587.

A further process to prepare compounds of formula I, involves reacting a compound of formula XIII with a compound of formula XIV

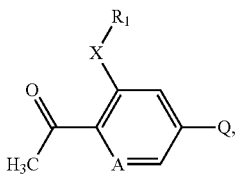

(XIV)

In the presence of a Lewis acid, such as Zinc(II)iodide or Indium(III) triflate, in an inert solvent such as chlorobenzene or 1,2,dichlorobenzene, with a catalytic copper(II) salt, such as Cu(II)acetate, under an oxygen or air atmosphere at temperatures between 100-180° C., preferably 110-140° C., to give compounds of formula I wherein $R_3$ is hydrogen. Such reactions have previously been described in the literature (see *Adv. Synth. Catal.* 2013, 355, 1741-1747, and *J. Org. Chem.*, 2013, 78, 12494-12504). Halogenation of compounds of formula I, wherein $R_3$ is hydrogen, with a halogenating agent such as N-chlorosuccinamide, N-bromosuccinamide, or N-iodosuccinamide, in a polar aprotic solvent such as acetonitrile or dimethylformamide, at ambient temperature, leads to compounds of formula I-u

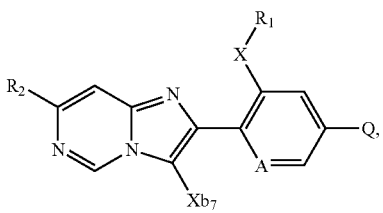

(I-u)

wherein Q, $R_1$, $R_2$, X, and A are as described in formula (I), and $X_{b7}$ is halogen. Compounds of formula I-u can be reacted with compounds $R_3$—$Y_{b7}$, wherein $Y_{b7}$ is a boron-derived functional group, as for example $B(OH)_2$ or $B(OR_{b4})_2$ wherein $R_{b4}$ can be a $C_1$-$C_4$alkyl group or the two groups $OR_{b4}$ can form together with the boron atom a five membered ring, as for example a pinacol boronic ester, in the presence of a palladium catalyst to give compounds of formula I-$u_1$, wherein $R_1$, $R_2$, $R_3$, A, X and Q are as defined as in formula I. The reaction is usually carried out in the presence of a base, for example potassium carbonate, cesium carbonate, or potassium phosphate, in an inert solvent, such as dioxane, optionally in the presence of water, with a palladium(0) catalyst, for example tetrakis(triphenylphosphine)palladium, at a temperature between 80-120° C. Such Suzuki reactions are well precedented in the literature, see for example Masuda, Naoyuki et al, WO 2012133607. The chemistry is illustrated in scheme 9

Scheme 9

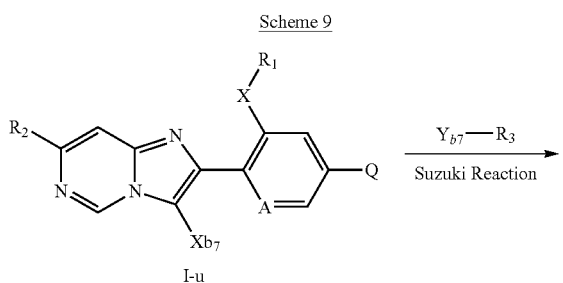

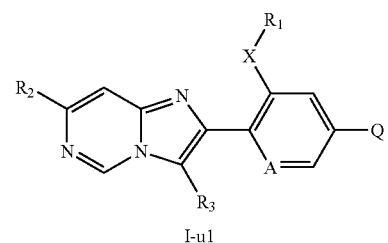

I-u1

Compounds of formula XII and XIV can be prepared from compounds of formula XVI by, for example, the methods shown in scheme 10.

Scheme 10

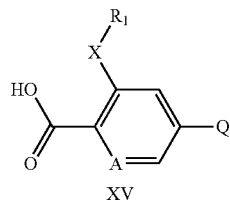

XV $(COCl)_2$, Inert solvent, e.g. $CH_2Cl_2$ room temp, or $SOCl_2$, $CH_2Cl_2$ room temp.

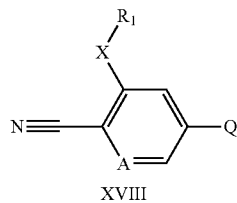

XVIII $R_3CH_2MgHal$  inert solvent, e.g. THF or ether, 0° C. to room temp,

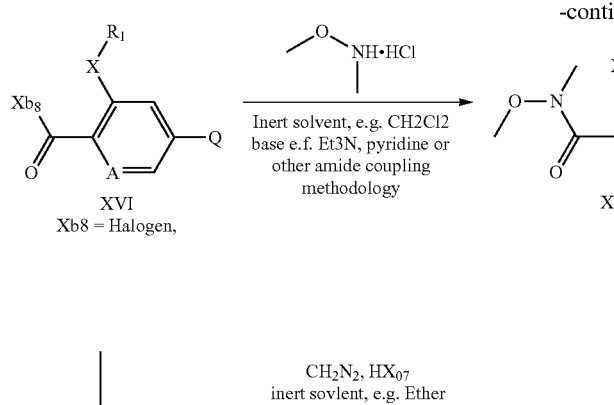
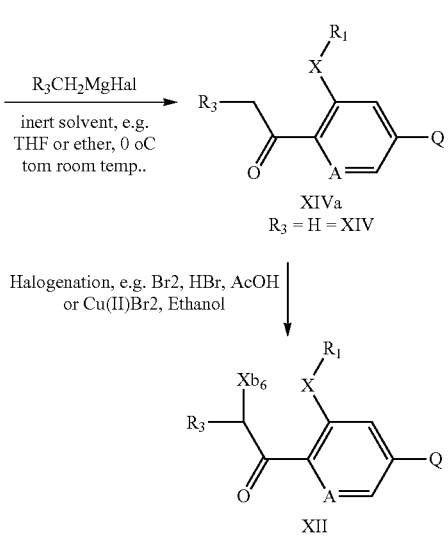

In scheme 10, an acyl halide of formula XVI (easily prepared from compounds of formula XV by methods known to those skilled in the art) is converted to a Weinreb amide XVII upon reaction with N,O-Dimethylhydroxylamine by methods described for example in C. Ferri, "Reaktionen der Organischen Synthese", Georg Thieme Verlag, Stuttgart, 1978, page 223ff. The Weinreb amide of formula XVII is then reacted with a Grignard reagent of formula $R_3CH_2MgHal$ according to the method of Weinreb (*Tetrahedron Letters* 1981, 22, 3815-3818) to give compounds of formula XIVa and XIV. Compounds of formula XIVa and XIV can also be prepared by treatment of nitrile compounds of formula XVIII, wherein Q, X, $R_1$, and A are as described in formula I, with a Grignard reagent of formula $R_3CH_2MgHal$, followed by acidic hydrolysis (as described in C. Ferri, "Reaktionen der Organischen Synthese", Georg Thieme Verlag, Stuttgart, 1978, page 223ff.).

The compounds of formula XIII

wherein $R_2$ is $C_2$-$C_3$ haloalkyl or $C_1$ haloalkylsulfanyl are novel, especially developed for the preparation of the compounds of formula I of this invention and therefore represent a further object of the invention.

The compounds of formula $Z_0$;

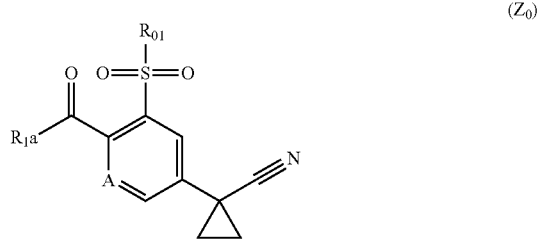

wherein $R_{01}$ is $C_1$-$C_4$alkyl, $C_3$-$C_6$cycloalkyl, or $C_3$-$C_6$cycloalkyl-$C_1$-$C_4$alkyl;

$R_{1a}$ is $C_1$-$C_4$alkyl, hydroxy, $C_1$-$C_4$alkoxy, or $C_1$-$C_4$ haloalkyl; and A is nitrogen or CH, are novel, especially developed for the preparation of the compounds of formula I of this invention and therefore represent a further object of the invention.

Compounds of formula XIVa and XIV can be halogenated to compounds of formula XII, with for example mixtures of bromine and hydrobromic acid in acetic acid (as described in *Phosphorus, Sulfur and Silicon and the Related Elements*, 2013, 188(12), 1835-1844) or with, for example, copper(II) bromide in an inert solvent, for example chloroform, ethyl acetate and the like, as described in *J. Med. Chem.*, 2013, 56(1), 84-96. Alternatively, compounds of formula XII where $R_3$ is hydrogen, can be prepared directly from compounds of formula XVI by treatment with diazomethane or trimethyl silyl diazomethane and subsequent treatment with an halogen acid, for example, hydrobromic acid or hydrochloric acid in an inert solvent such as diethyl ether. Such procedures are well known in the literature, for example see *Eu. J. Med. Chem.*, 1987, 22(5), 457-62 and WO 2009010455.

Compounds of formula XV can be prepared (as shown in scheme 11) by ester hydrolysis of compounds of formula XX, wherein A, Xb3, and $R_1$ are as previously defined, and $R_{11}$ is $C_1$-$C_6$alkyl, by methods known to those skilled in the art, for example by treatment with an alkaline earth metal base, such as lithium hydroxide, typically in water with sufficient miscible organic solvent, for example THF or acetone, to dissolve compounds of the formula XX. Compounds XX can be prepared by a Suzuki reaction, which involves for example, reacting compounds of formula XIX, wherein Xb3 is a leaving group like, for example, chlorine, bromine or iodine, or an aryl- or alkylsulfonate such as trifluoromethanesulfonate (especially preferred are those in which Xb1 is fluoro or bromo) with compounds of formula IIIa, wherein $Y_{b1}$ can be a boron-derived functional group, as for example $B(OH)_2$ or $B(OR_{b1})_2$ wherein $R_{b1}$ can be a $C_1$-$C_4$alkyl group or the two groups $OR_{b1}$ can form together with the boron atom a five membered ring, as for example a pinacol boronic ester. The reaction can be catalyzed by a palladium based catalyst, for example tetrakis(triphenylphosphine)-palladium or (1,1'bis(diphenylphosphino)-ferrocene)dichloropalladium-dichloromethane (1:1 complex), in presence of a base, like sodium carbonate or cesium fluoride, in a solvent or a solvent mixture, like, for example a mixture of 1,2-dimethoxyethane and water or of dioxane and water, preferably under inert atmosphere. The reaction temperature can preferentially range from ambient temperature to the boiling point of the reaction mixture. Such Suzuki reactions are well known to those skilled in the art and have been reviewed, for example *J. Orgmet. Chem.* 576, 1999, 147-168.

Scheme 11

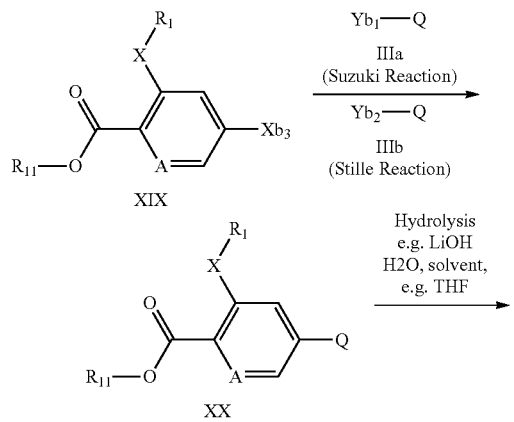

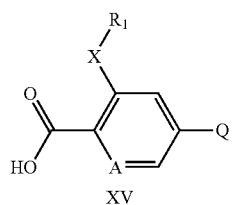

Alternatively compounds of formula XX can be prepared by a Stille reaction of compounds of formula IIIb wherein $Y_{b2}$ is a trialkyl tin derivative, preferably tri-n-butyl tin, with compounds of formula XIX. Such Stille reactions are usually carried out in the presence of a palladium catalyst, for example tetrakis(triphenylphosphine)palladium(0), or (1,1'bis(diphenylphosphino)-ferrocene)dichloropalladium-dichloromethane (1:1 complex), in an inert solvent such as DMF, acetonitrile, or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example *J. Org. Chem.*, 2005, 70, 8601-8604, *J. Org. Chem.*, 2009, 74, 5599-5602, and *Angew. Chem. Int. Ed.*, 2004, 43, 1132-1136.

In a very similar manner compounds of formula Xa can similarly be prepared as shown in scheme 12, using analogous procedures and strategies to those described in scheme 8.

Scheme 12.

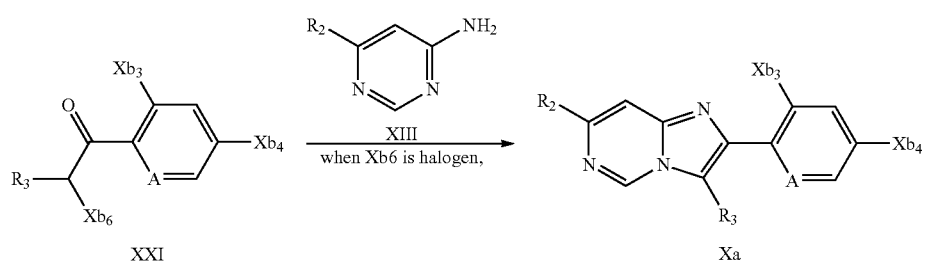

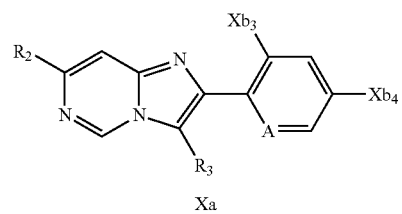

The intermediates required to synthesize compounds of formula XXI, can be obtained analogously to the chemistry shown in scheme 10, and illustrated here again in scheme 13.

mediate of the formulae IIIa or IIIb is from a compound of the formula IIIc which is obtained by via metal-halogen exchange of compound of formula V with an organometallic

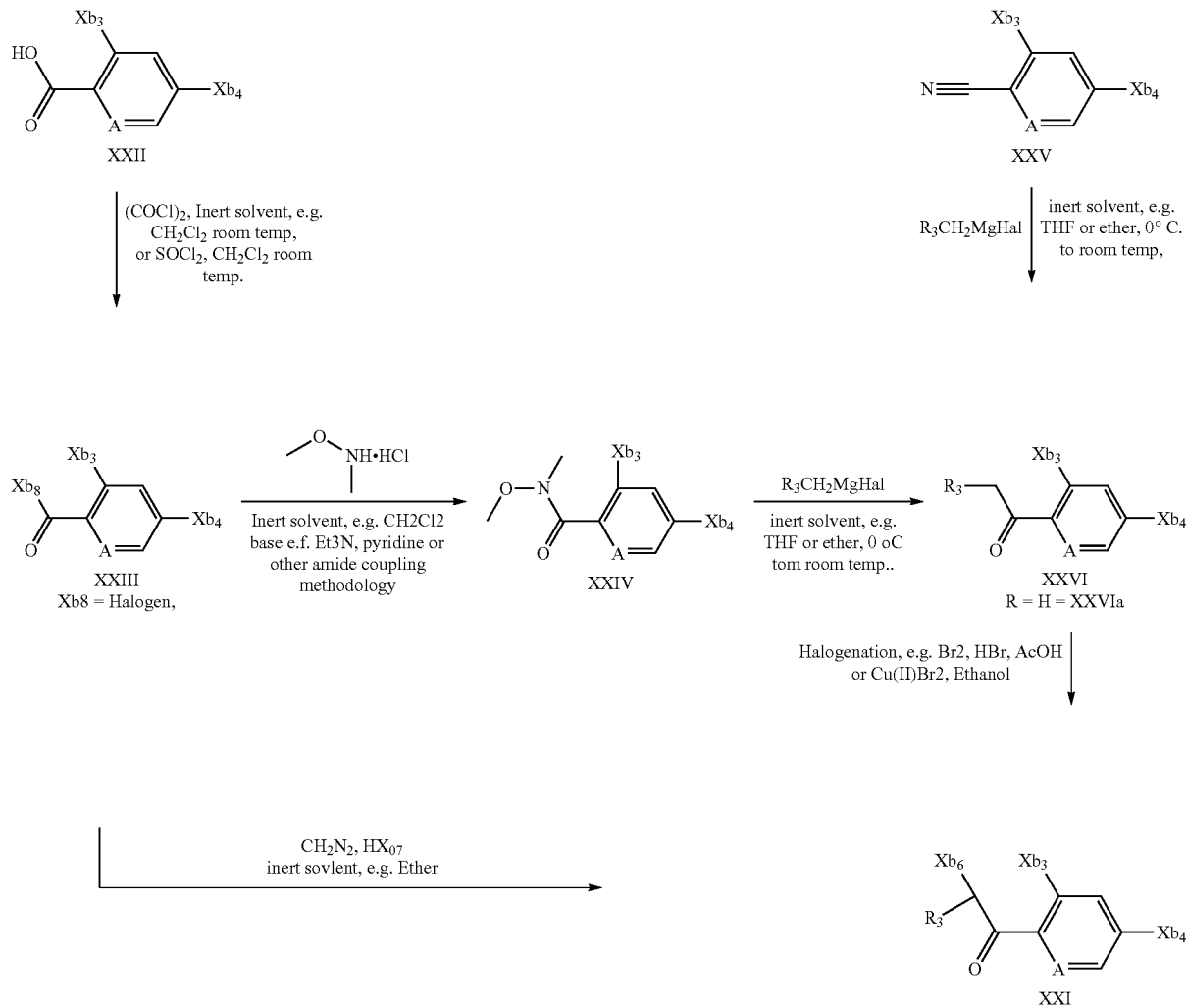

A large number of compounds of the formula V are commercially available or can be prepared by those skilled in the art. Many chemical transformations, well known by those skilled in the art, can be used to access boronic acid derivatives of formula IIIa, starting from various and easily available starting materials, as for example, to cite only a few (scheme 13), hydrogen abstraction on a heteroaromatic compound of the formula V wherein Xb2 is hydrogen, with a strong base (step A), like butyl lithium or lithium diisopropylamide or (i-PrMgCl. LiCl), followed by reaction of the metalated intermediate of the formula IIIc, wherein $Zb_2$ is a metal such as $Li^+$ or $MgCl^+$ for example, with, for example, a trialkylborate (step B), or a tri-n-butyl tin chloride (step B). Another way to access an organometal interspecies (step C), using for example butyl lithium or an organ magnesium compound, or direct metalation with a metal, like magnesium.

Introduction of a pinacolborate functional group via a palladium catalyzed reaction with bispinacol diborane, or hexa-n-butyldistannane, on a compound of the formula V, wherein Xb2c, is another common strategy (scheme 13, step D). In the compounds of formula IIIa, and IIIb within scheme 13, Q has the values defined for the formula I. A person skilled in the art will be able to select an adequate preparation method to access compounds of formula IIIa and IIIb depending on the values of Q.

Scheme 13

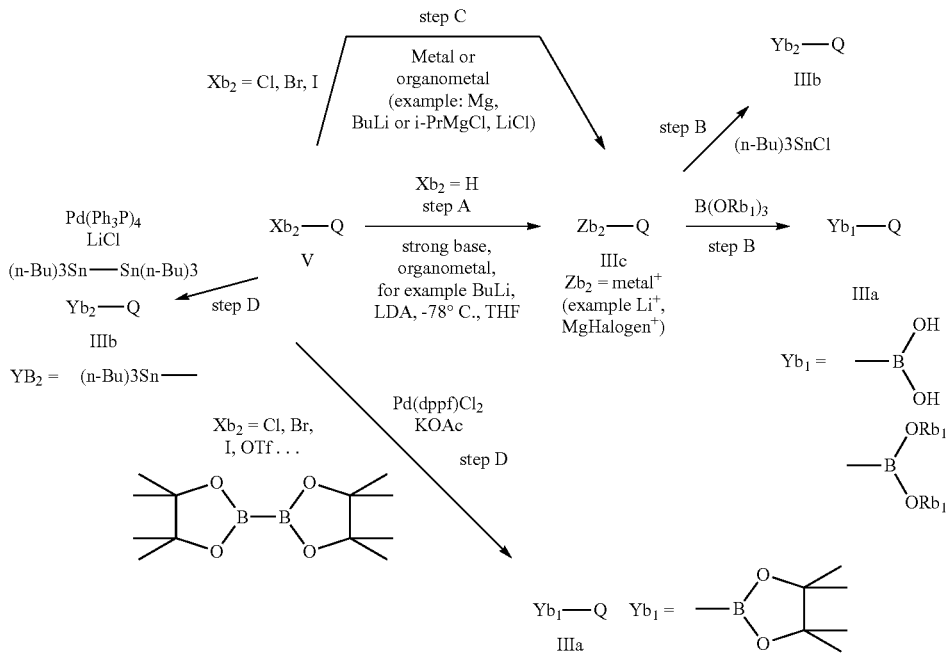

Compounds of formula IV, wherein A, X, $X_1$, $R_1$ and $R_2$ are as described in formula I, can be prepared from compounds of formula II (scheme 14), wherein A, X, $X_1$, $R_1$ and $R_2$ are as described in formula I. Indeed, compounds of formula II, wherein $Xb_1$ is chlorine, bromine or iodine, can be treated with an organometallic species like, for example, butyl lithium or an organomagnesium compound, to generate an intermediate compound of the formula II-a, wherein $Zb_3$ is as defined in the scheme, via metal-halogen exchange. This reaction is preferentially performed in an anhydrous aprotic solvent, such as THF, at low temperature (between −120° C. and 0° C.), preferentially between −110° C. and −60° C.). The intermediate organometal compound of formula II-a is preferably directly converted into compound of formula IV by reaction with a boronate compound $B(OR_{b2})_3$, wherein $R_{b2}$ is a $C_1$-$C_4$alkyl group. Depending on nature of the boronate, the reaction treatment conditions and the workup conditions, the boronic acid IV, wherein $Yb_3$ is —$B(OH)_2$, or a dialkylboronate IV, wherein $Yb_3$ is —$B(OR_{b2})_2$, can be formed.

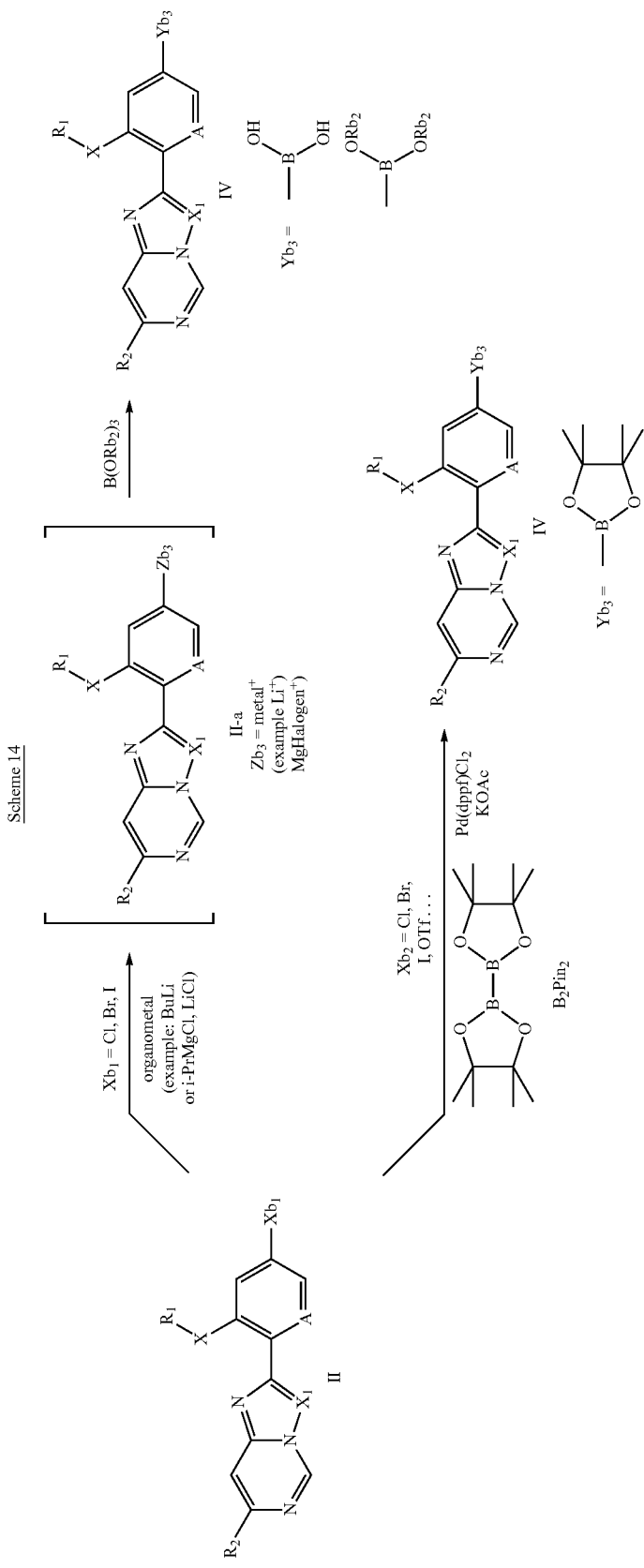

Introduction of a pinacolborate functional group via a palladium catalyzed reaction with bispinacol diborane on compound of the formula II, wherein Xb1 is chlorine, bromine, iodine or triflate, is another common strategy (scheme 14). In the compounds of formula II within scheme 14, A, $R_1$, $R_2$, X, and $X_1$, have the values defined for the formula I, and Xb1 is chlorine, bromine, fluorine, iodine or triflate. A person skilled in the art will be able to select an adequate preparation method to access compounds of formula IIa from II depending on the values A, $R_1$, $R_2$, X, and $X_1$.

In a similar fashion to the chemistry shown in scheme 14, compounds of formula VIII can be obtained from compounds of formula X (scheme 15).

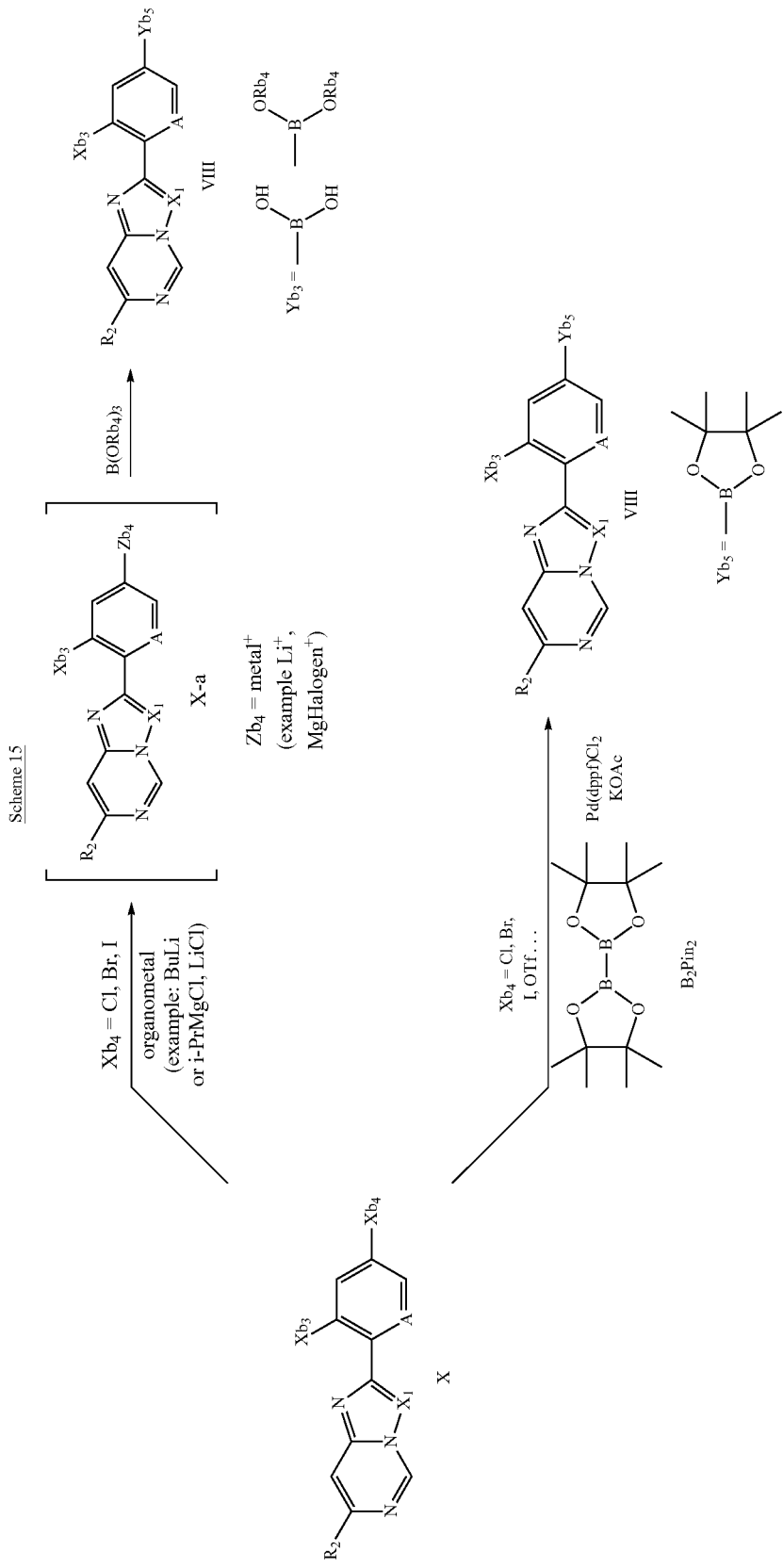

The very similar preparation methods described in schemes 14 and 15 may be applied for the synthesis of intermediates of the formula IX and VI, but in this case instead of using boronic compounds e.g. of formula $B(OR_{b2})_3$, those skilled in the art would know to use a tin compound of formula $(n\text{-butyl})_3SnCl$ (as described as for example in *Eu. J. Chem.*, 4098-4104, 20, 2014) or instead of bispinacol diborane, the use of hexabutylditin (as described in for example Eur. Pat. Appl., 2749561, 2014). This is illustrated for compound VI in scheme 16.

mine or iodine, or a sulfonate, like for example a trifluoromethanesulfonate. In formula II and H—C≡C-Qd, A, X, $X_1$, $R_1$, $R_2$ and Qd are as described above in formula I-c. This type of reaction is well known to a person skilled in the art and commonly described as the Sonogashira cross-coupling reaction. In this reaction, the substituted aromatic component of formula II is reacted with the terminal alkyne of formula H—C≡C-Qd in the presence of a copper(I) salt, like CuI, preferably in catalytic amount, and in the presence of a palladium based catalyst, for example bis(triphenyl- Scheme 16.

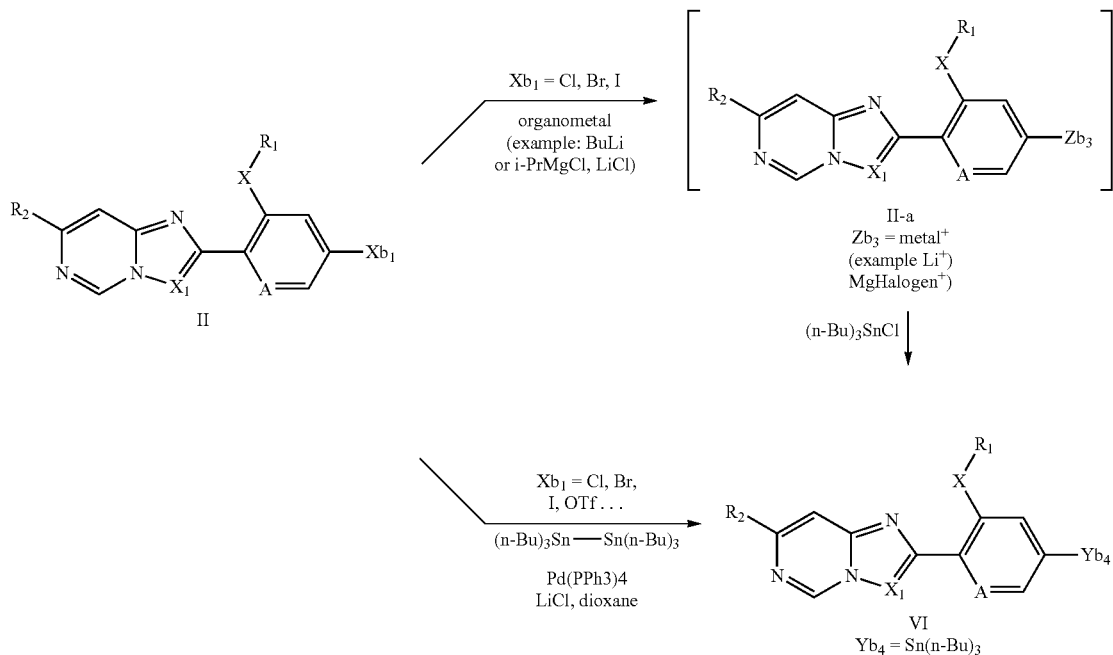

A particular case of compounds of formula I is represented by compounds of formula I-c, wherein A, $R_1$, $R_2$, X and $X_1$ are as described in formula I and Q is a 1-alkynyl group of the structure —C≡C-Qd:

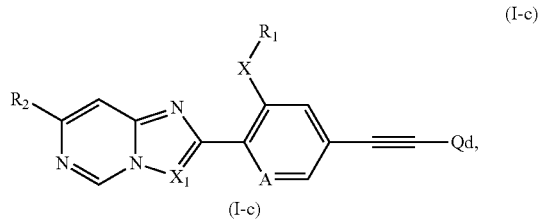

(I-c)

wherein Qd is hydrogen, halogen, cyano, $C_1$-$C_4$alkyl, $C_1$-$C_4$ haloalkyl, $C_3$-$C_6$cycloalkyl, tri($C_1$-$C_4$alkyl)silyl or phenyl, or is phenyl which can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ halo-alkylsulfanyl, $C_1$-$C_4$ haloalkylsulfinyl, $C_1$-$C_4$ haloalkylsulfonyl and —C(O)$C_1$-$C_4$ haloalkyl. Compounds of the formula I-c can be prepared, for example, by reacting compounds of formula II with terminal alkynes of formula H—C≡C-Qd (scheme 17), wherein $X_{b1}$ can be a halogen, preferentially chlorine, brophosphine)-palladium dichloride or (1,1'bis(diphenylphosphino)-ferrocene)dichloropalladium-dichloromethane (1:1 complex), preferably in catalytic amount, and in the presence of a base, such as a tertiary amine, for example triethylamine or Hünig's base (N,N-diisopropylethylamine), preferably in equivalent amount or in excess. The reaction can be performed in the amine as solvent or another compatible solvent can be used as dilutant, as for example an ether, like tetrahydrofurane. The reaction is best performed under inert atmosphere and can take place at temperatures in the range from below 0° C. to the boiling point of the reaction mixture.

Scheme 17:

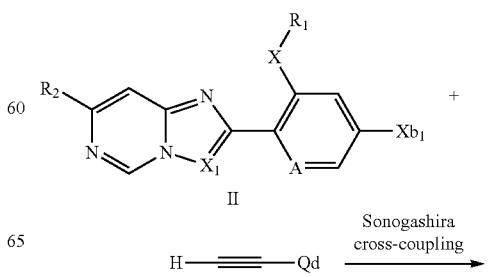

-continued

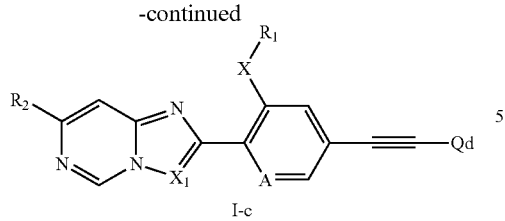

I-c

A further particular example of compounds of formula I is represented by compounds of formula I-d.

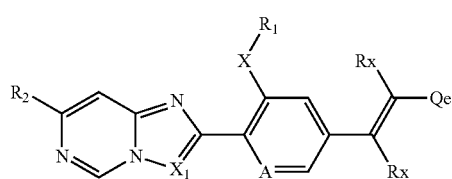

I-d wherein Rx is as described above, and Qe is hydrogen, halogen, cyano, $C_1$-$C_4$alkyl, $C_1$-$C_4$ haloalkyl, $C_3$-$C_6$cycloalkyl, or is phenyl which can be mono- or polysubstituted by substituents selected from the group consisting of halogen, cyano, $C_1$-$C_4$alkyl, $C_1$-$C_4$ haloalkyl, $C_1$-$C_4$ haloalkoxy, $C_1$-$C_4$alkoxy, $C_1$-$C_4$ halo-alkylsulfanyl, $C_1$-$C_4$ haloalkylsulfinyl, $C_1$-$C_4$ haloalkylsulfonyl and —C(O)$C_1$-$C_4$ haloalkyl.

Compounds of the formula I-d can be prepared, for example, by reacting compounds of formula II with terminal alkenes of formula CH($R_x$)=C($R_x$)–Qe (scheme 18), wherein $X_{b1}$ can be a halogen, preferentially chlorine, bromine or iodine, or a sulfonate, like for example a trifluoromethanesulfonate. In formula II and CH($R_x$)=C($R_x$)–Qe, A, X, $X_1$, $R_1$, $R_2$ and Qe are as described above in formula I-d.

This type of reaction is well known to a person skilled in the art, and commonly described as the Heck cross-coupling reaction.

Scheme 18:

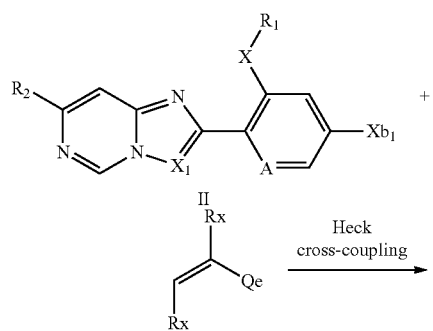

-continued

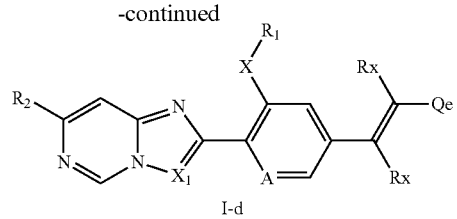

I-d

In this reaction, the substituted aromatic component of formula II is reacted with the terminal alkyne of formula CH($R_x$)=C($R_x$)–Qe in the presence of a palladium catalyst, optionally in the presence of a ligand, and a base in a solvent (for example dimethyl formamide) at elevated temperatures. The catalyst can be for example tetrakis(triphenylphosphine)palladium(0), palladium chloride or palladium(II)acetate. The ligand can be for example triphenylphosphine, or BINAP, and the base for example triethylamine, potassium carbonate or sodium acetate. Such reactions are well known in the literature and have been described for example in *Chem. Rev.* 100 (8): 3009-3066. 2000. The compounds formed may have the trans-stereochemistry shown in scheme 18, but depending on the reaction conditions, one skilled in the art can also obtain compounds of formula I-d with a cis-double bond configuration.

Compounds of formula I-d can be further elaborated to compounds of formula 1-e (Scheme 19) by Cyclopropanation, for example with diazomethane in the presence of a palladium catalyst (for example Pd(OAc)$_2$ (for example as described in *J. Org. Chem.*, 1980, 45, 695 and *Synthesis*, 1981, 714) or by Simmons-Smith zinc carbene chemistry (see *Org. React.* 1973, 20, page 1). Those skilled in the art will appreciate there are many other methods to cyclopropanate double bonds.

Scheme 19:

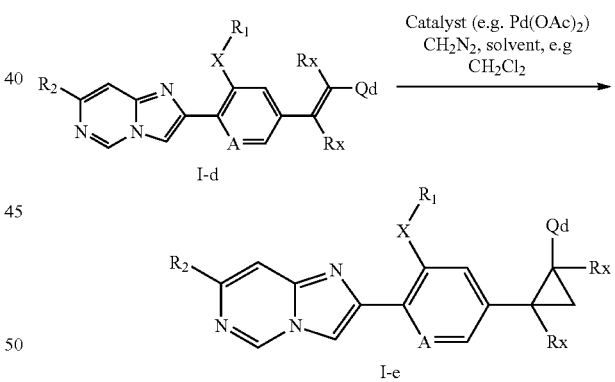

Compounds of formula I wherein Q is $C_3$-$C_6$cycloalkyl, mono- or polysubstituted by substituents selected from the group consisting of halogen, cyano, hydroxycarbonyl, amidocarbonyl, $C_1$-$C_4$ haloalkyl, and phenyl, may be prepared by methods described above. For the special case of compounds of formula I wherein Q is cycloalkyl substituted by cyano and $C_1$-$C_4$ haloalkyl, the compounds can be prepared by the methods shown in Scheme 20.

Scheme 20:
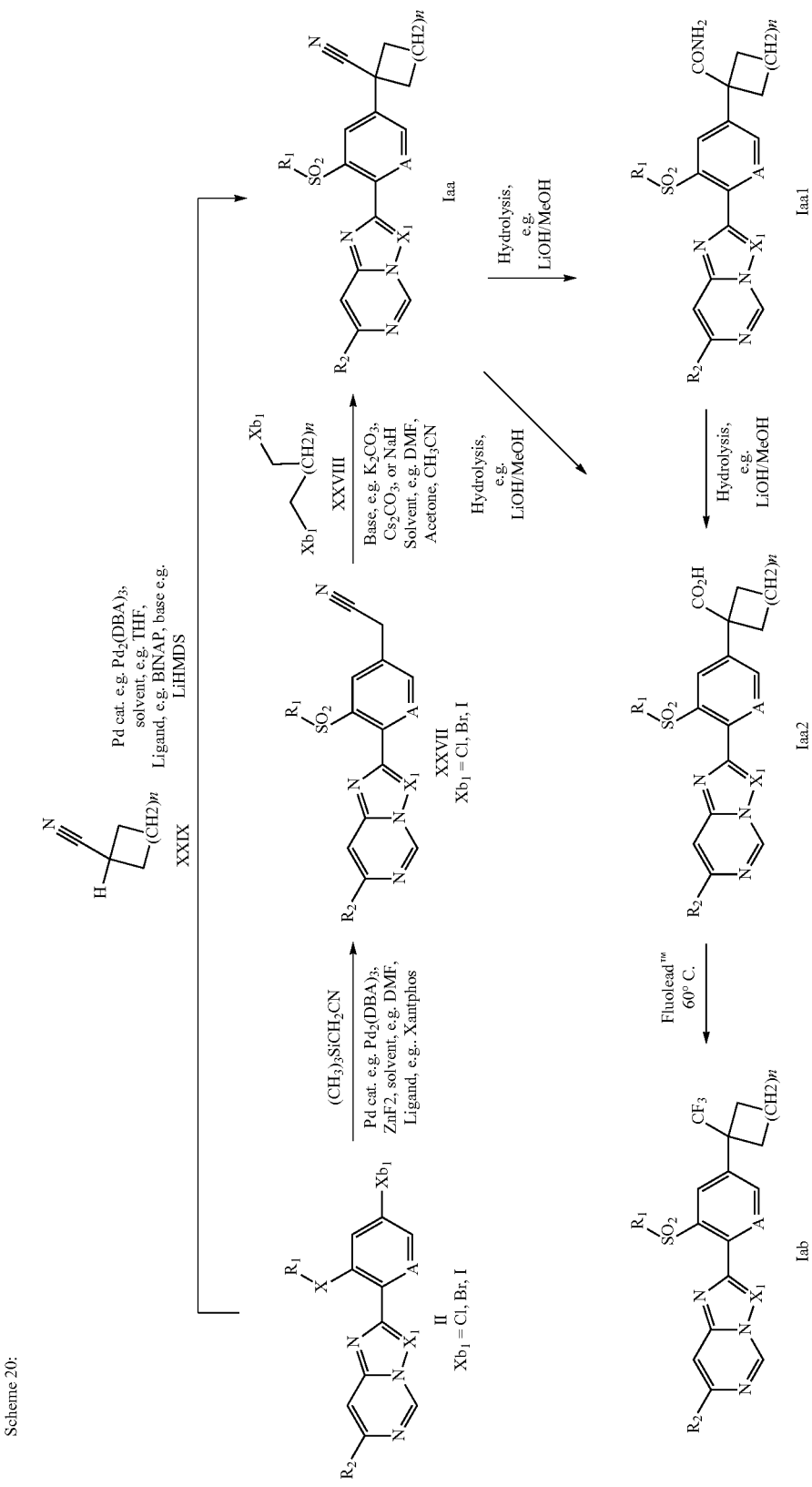

As shown in Scheme 20, treatment of compounds of formula II, where X is SO2, with trimethylsilylacetonitrile, in the presence of zinc(II)fluoride, and a palladium(0)catalyst such as Tris(dibenzylideneacetone)dipalladium(0)-chloroform adduct (Pd₂(dba)₃), a ligand, for example Xantphos, in an inert solvent, such as DMF at temperatures between 100-160° C., optionally under microwave heating, leads to compounds of formula XXVII. Such chemistry has been described in the literature, e.g. in *Org. Lett.*, 16(24), 6314-6317; 2014. Compounds of formula XXVII can be treated with compounds of formula XXVIII, wherein n is 1, 2 or 3, in the presence of a base such as sodium hydride, K₂CO₃, or Cs₂CO₃, in an inert solvent such as DMF, acetone, or acetonitrile, to give compounds of formula Iaa. Alternatively, compounds of formula Iaa can be prepared directly from compounds of formula II by treatment with compounds of formula XXIX, wherein n is 1, 2 or 3, with Pd₂(dba)₃, a ligand, such as BINAP, a strong base such as LiHMDS, in an inert solvent such as THF at temperatures between 40-70° C. Such chemistry has been described in, for example, *J. Am. Chem. Soc.*, 127(45), 15824-15832; 2005. Compounds of formula Iaa can be converted to compounds of formula Iaa1 and Iaa2 by basic hydrolysis as known to those skilled in the art. Compounds of formula Iaa3, wherein Q is a C1-C6alylky substituted by cyano and halogen, can be prepared from compounds of formula Iaa by treatment with a halogen source, for example Cu(II)Br₂, Br₂, or HBr in an inert solvent for example EtOH or acetic acid (Scheme 21).

Scheme 21:

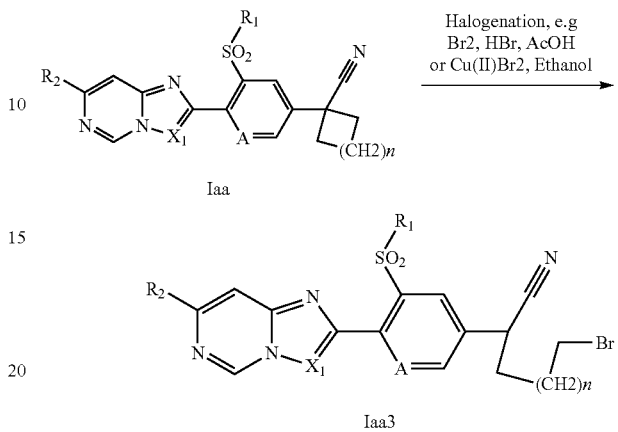

Alternatively compounds of formula Iaa can be prepared as shown in Scheme 22.

Scheme 22.

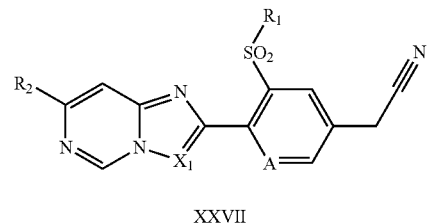

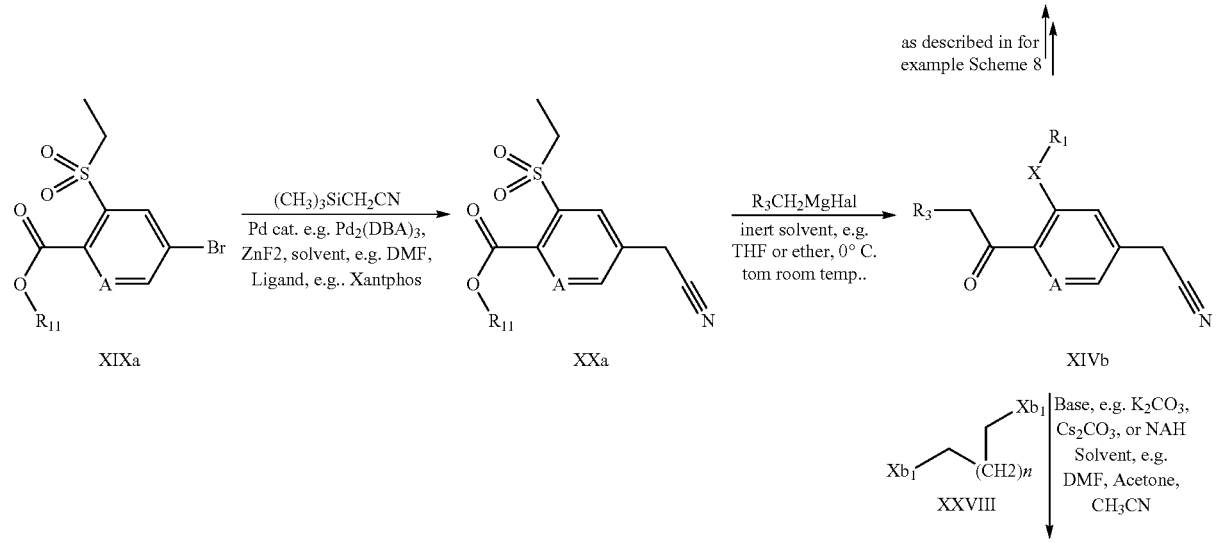

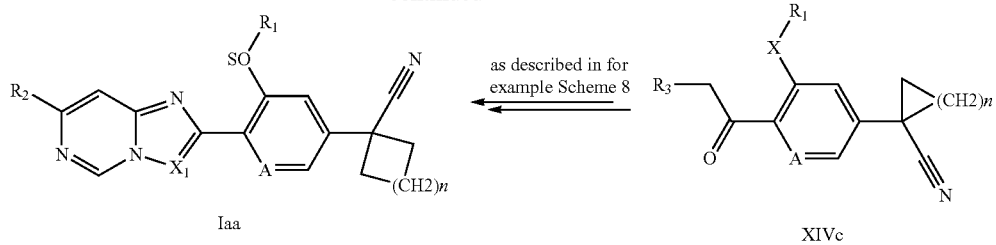

As shown in Scheme 22, the chemistry used is identical to that described in Scheme 20, it is just that the substrates for the reactions are different. Thus, reaction of the previously described compound XIXa with TMS-acetonitrile as described in scheme 20, leads to compounds of formula XXa. Reaction of compounds of formula XXa with a Grignard $R_3CH_2MgHal$ leads to compounds of formula XIVb. This can be converted to compounds of formula XXVII by the chemistry described in scheme 8.

Compounds of formula XIVb can be reacted with compounds of formula XXVIII to give compounds of formula XIVc, as described vide supra. The compounds of formula XIVc can be converted to compounds of formula Iaa analogously to the chemistry described in scheme 8.

Intermediates of formula XIII are known in the literature or can be prepared from known compounds by those skilled in the art. Compounds of formula XIII wherein $R_2$ is $C_1$-$C_2$ haloalkyl, $C_1$ haloalkylsulfanyl, $C_1$ haloalkylsulfinyl, $C_1$ haloalkylsulfonyl, or $C_3$-$C_6$cycloalkyl can be prepared as shown in scheme 20.

solvent, such as DMF or NMP, at temperatures between 50-120° C. leads to compounds of formula XIIIb and XIIIc, respectively. Such reactions are well precedented in the literature, see for example, *Angew. Chem. Int. Ed.* 2011, 50, 3793 and *Org. Lett.* 2014, 16, 1744 ($R_2$ is $CF_3$), and *Angew. Chem. Int. Ed.* 2012, 51, 536 ($R_2$ is $CF_2CF_3$). Compounds of formula XIIIa can be converted to compounds of formula XIIId by treatment with hydroiodic acid, optionally in the presence of sodium iodide, according to those skilled in the art and as described for example in *Bio. Med. Chem.*, 15(4), 1586-1605, 2007. Reaction of compounds of formula XIIId with (bpy)$CuSCF_3$ in an inert solvent, such as DMF or NMP, at temperatures between 50-120° C. leads to compounds of formula XIIIf. Such reactions have precedence in the literature, for example in *Angew. Chem. Int. Ed.* 2013, 52, 1548-1552. Compounds of formula XIIIf can be further oxidized to compounds of formula XIIIg and XIIIh by oxidation, for example with MCPBA or other methods known to those skilled in the art. Compounds of formula XIII, wherein $R_2$ is $C_3$-$C_6$cycloalkyl can be prepared for

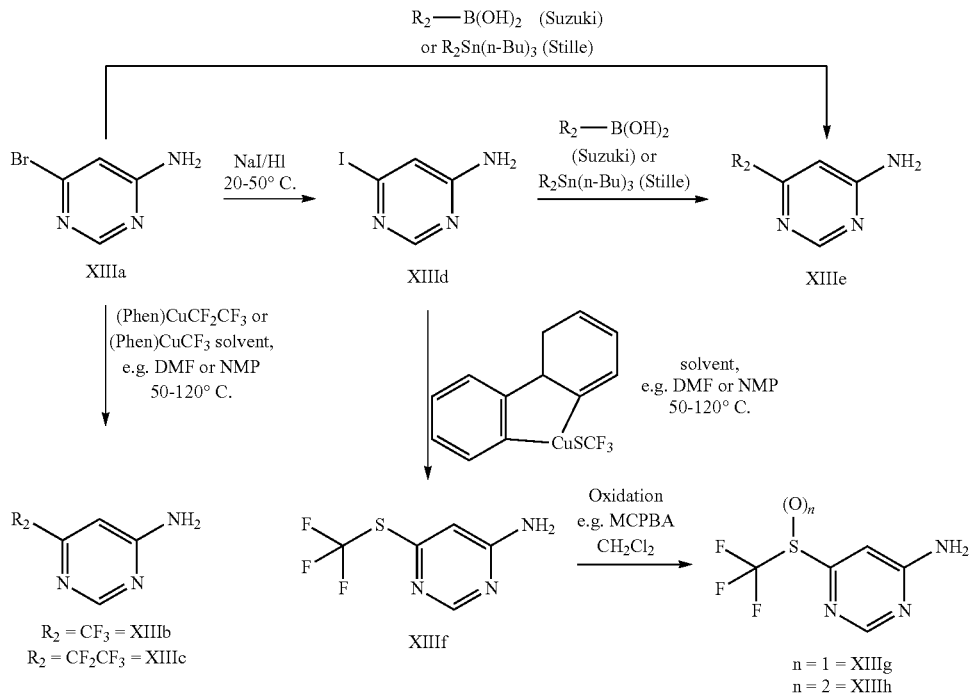

As shown in scheme 23, reaction of the known compound XIIIa with (Phen)$CuCF_3$ or (Phen)Cu $CF_2CF_3$ in an inert compounds of formula XIIIa or XIIId via Suzuki reactions with a compound of formula $R_2B(OH)_2$ or Stille reactions with compounds of formula $R_2Sn(n-Bu)3$. Suzuki and Stille reactions are general reactions already discussed in this application, and also well known to those skilled in the art.

For preparing all further compounds of the formula I functionalized according to the definitions of $R_1$, $R_2$, Q, $X_1$ and $X_2$, there are a large number of suitable known standard methods, for example alkylation, halogenation, acylation, amidation, oximation, oxidation and reduction, metal (for example palladium, copper, and nickel) catalysed C—C and C-Heteroatom coupling reactions available, the choice of the preparation methods which are suitable depending on the properties (reactivity) of the substituents in the intermediates The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties, can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 6 below can be prepared according to the methods described above. The examples which follow are intended to illustrate the invention and show preferred compounds of formula I.

Table X: This table discloses 44 substituent definitions X.001 to X.0044 of the formula I-1a:

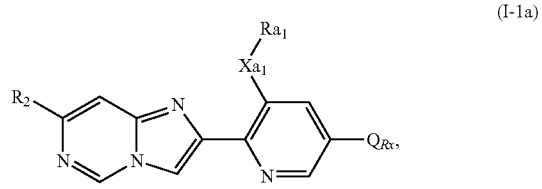

(I-1a)

wherein $Ra_1$, $R_2$ and $Q_{Rx}$ are as defined below, and the arrow shows the point of attachment to the aromatic ring.

TABLE X

| Comp. No | $R_2$ | $R_{a1}$ | $Q_{Rx}$ |
|---|---|---|---|
| X.001 | $CF_3$ | $CH_2CH_3$ | phenyl |
| X.002 | $CF_3$ | $CH_2CH_3$ | 4-Cl-phenyl |
| X.003 | $CF_3$ | $CH_2CH_3$ | 4-$CF_3$-phenyl |
| X.004 | $CF_3$ | $CH_2CH_3$ | pyrazol-1-yl |
| X.005 | $CF_3$ | $CH_2CH_3$ | 4-$CF_3$-pyrazol-1-yl |
| X.006 | $CF_3$ | $CH_2CH_3$ | 3-$CF_3$-pyrazol-1-yl |
| X.007 | $CF_3$ | $CH_2CH_3$ | pyrimidin-2-yl |
| X.008 | $CF_3$ | $CH_2CH_3$ | 5-Cl-pyrimidin-2-yl |
| X.009 | $CF_3$ | $CH_2CH_3$ | cyclopropyl |
| X.010 | $CF_3$ | $CH_2CH_3$ | vinyl (CH=CH$_2$) |
| X.011 | $CF_3$ | $CH_2CH_3$ | ethynyl (C≡CH) |
| X.012 | $CF_3$ | $CH_2CH_3$ | 2-$CF_3$-cyclopropyl |
| X.013 | $CF_3$ | $CH_2CH_3$ | (E)-2-(1-methyl-4-trifluoromethyl-imidazol-2-yl)vinyl |
| X.014 | $CF_3$ | $CH_2CH_3$ | (pyrimidin-2-yl)ethynyl |
| X.015 | $CF_3$ | $CH_2CH_3$ | 1-CN-cyclopropyl |
| X.016 | $CF_3$ | $CH_2CH_3$ | 2-CH$_3$-cyclopropyl |
| X.017 | $CF_3$ | $CH_2CH_3$ | 1-(C(O)OCH$_3$)-cyclopropyl |
| X.018 | $CF_3$ | $CH_2CH_3$ | 1-(C(O)N(CH$_3$)$_2$)-cyclopropyl |
| X.019 | $CF_3$ | $CH_2CH_3$ | 1-$CF_3$-cyclopropyl |
| X.020 | $CF_3$ | $CH_2CH_3$ | 1-CH$_3$-cyclopropyl |
| X.021 | $CF_3$ | $CH_2CH_3$ | 2,2-di-CH$_3$-cyclopropyl |

TABLE X-continued

| Comp. No | R₂ | R_{a1} | Q_{Rx} |
|---|---|---|---|
| X.022 | CF₃ | CH₂CH₃ | cyclopropyl-CONH₂ |
| X.023 | CF₃ | CH₂CH₃ | cyclopropyl-CO₂H |
| X.024 | CF₃ | CH₂CH₃ | 3-(methylthio)phenyl |
| X.025 | CF₃ | CH₂CH₃ | 4-cyanophenyl |
| X.026 | CF₃ | CH₂CH₃ | 2,4-difluorophenyl |
| X.027 | CF₃ | CH₂CH₃ | 4-(trifluoromethoxy)phenyl |
| X.028 | CF₃ | CH₂CH₃ | 4-bromo-2-cyanobutyl |
| X.029 | CF₃ | CH₂CH₃ | 3,5-difluorophenyl |
| X.030 | CF₂CF₃ | CH₂CH₃ | 4-chlorophenyl |
| X.031 | CF₂CF₃ | CH₂CH₃ | 3,5-difluoropyridin-2-yl |
| X.032 | SCF₃ | CH₂CH₃ | 3-(trifluoromethyl)-1H-pyrazol-1-yl |
| X.033 | CF₂CF₃ | CH₂CH₃ | pyrimidin-2-yl |
| X.034 | CF₂CF₃ | CH₂CH₃ | 4-(trifluoromethyl)phenyl |
| X.035 | CF₂CF₃ | CH₂CH₃ | 4-fluorophenyl |
| X.036 | SCF₃ | CH₂CH₃ | 3-(trifluoromethyl)-1H-pyrazol-1-yl |
| X.037 | CF₃ | CH₂CH₃ | 3,5-dichlorophenyl |
| X.038 | CF₃ | CH₂CH₃ | 3-fluorophenyl |
| X.039 | CF₃ | CH₂CH₃ | 3-chlorophenyl |
| X.040 | SCF₃ | CH₂CH₃ | 2,3-dichloropyridin-6-yl |
| X.041 | SCF₃ | CH₂CH₃ | 4-(trifluoromethyl)pyridin-2-yl |
| X.042 | SCF₃ | CH₂CH₃ | 3-chloro-1H-pyrazol-1-yl |
| X.043 | CF₃ | CH₂CH₃ | (3,5-difluorophenyl)ethynyl |

TABLE X-continued

| Comp. No | R$_2$ | R$_{a1}$ | Q$_{Rx}$ |
|---|---|---|---|
| X.044 | CF$_3$ | CH$_2$CH$_3$ |  | and the N-oxides of the compounds of Table X.

Table 1:

This table discloses the 44 compounds 1.001 to 1.044 of the formula I-1a, wherein Xa$_1$ is S, and Ra$_1$, R$_2$ and Q$_{Rx}$ are as defined in Table X. For example, compound No. 1.001 has the following structure:

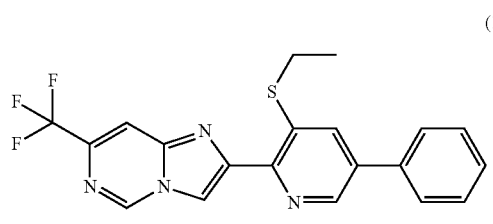
(1.001)

Table 2:

This table discloses the 44 compounds 2.001 to 2.044 of the formula I-1a, wherein Xa$_1$ is SO, and Ra$_1$, R$_2$ and Q$_{Rx}$ are as defined in Table X.

Table 3:

This table discloses the 44 compounds 3.001 to 3.044 of the formula I-1a, wherein Xa$_1$ is SO$_2$, and Ra$_1$, R$_2$ and Q$_{Rx}$ are as defined in Table X.

Table Y:

This table discloses 44 substituent definitions Y.001 to Y.044 of the formula I-2a:

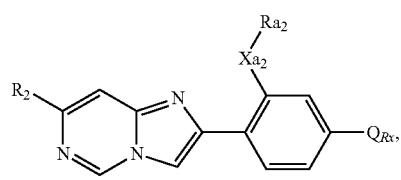
(I-2a)

wherein Ra$_2$, R$_2$ and Q$_{Rx}$ are as defined below, and the arrow shows the point of attachment to the aromatic ring.

TABLE Y

| Comp. No | R$_2$ | Ra$_1$ | Q$_{Rx}$ |
|---|---|---|---|
| Y.001 | CF$_3$ | CH$_2$CH$_3$ | 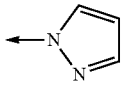 |
| Y.002 | CF$_3$ | CH$_2$CH$_3$ | 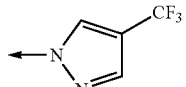 |
| Y.003 | CF$_3$ | CH$_2$CH$_3$ | 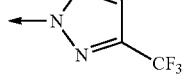 |
| Y.004 | CF$_3$ | CH$_2$CH$_3$ | 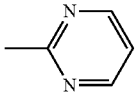 |
| Y.005 | CF$_3$ | CH$_2$CH$_3$ | 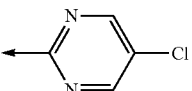 |
| Y.006 | CF$_3$ | CH$_2$CH$_3$ |  |
| Y.007 | CF$_3$ | CH$_2$CH$_3$ | 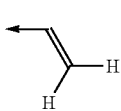 |
| Y.008 | CF$_3$ | CH$_2$CH$_3$ |  |
| Y.009 | CF$_3$ | CH$_2$CH$_3$ |  |
| Y.010 | CF$_3$ | CH$_2$CH$_3$ | 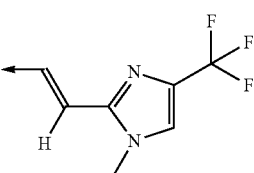 |
| Y.011 | CF$_3$ | CH$_2$CH$_3$ | 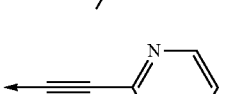 |
| Y.012 | CF$_3$ | CH$_2$CH$_3$ |  |
| Y.013 | CF$_3$ | CH$_2$CH$_3$ | 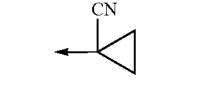 |
| Y.014 | CF$_3$ | CH$_2$CH$_3$ | 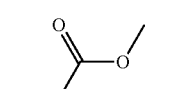 |
| Y.015 | CF$_3$ | CH$_2$CH$_3$ |  |
| Y.016 | CF$_3$ | CH$_2$CH$_3$ | 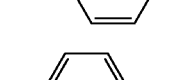 |
| Y.017 | CF$_3$ | CH$_2$CH$_3$ | 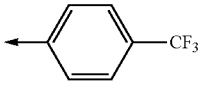 |

TABLE Y-continued

| Comp. No | R₂ | Ra₁ | Q_Rx |
|---|---|---|---|
| Y.018 | CF₃ | CH₂CH₃ | 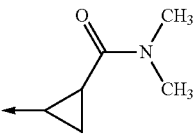 |
| Y.019 | CF₃ | CH₂CH₃ | 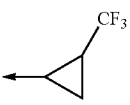 |
| Y.020 | CF₃ | CH₂CH₃ | 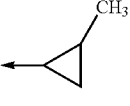 |
| Y.021 | CF₃ | CH₂CH₃ | 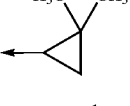 |
| Y.022 | CF₃ | CH₂CH₃ | 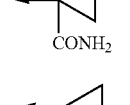 |
| Y.023 | CF₃ | CH₂CH₃ | 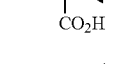 |
| Y.024 | CF₃ | CH₂CH₃ | 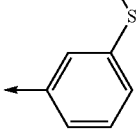 |
| Y.025 | CF₃ | CH₂CH₃ | 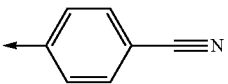 |
| Y.026 | CF₃ | CH₂CH₃ | 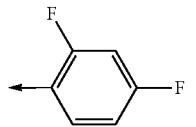 |
| Y.027 | CF₃ | CH₂CH₃ | 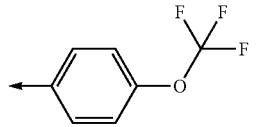 |
| Y.028 | CF₃ | CH₂CH₃ | 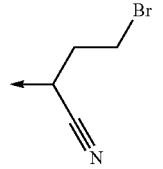 |
| Y.029 | CF₃ | CH₂CH₃ | 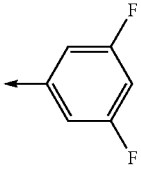 |

TABLE Y-continued

| Comp. No | R₂ | Ra₁ | Q_Rx |
|---|---|---|---|
| Y.030 | CF₂CF₃ | CH₂CH₃ | 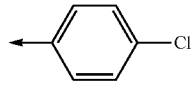 |
| Y.031 | CF₂CF₃ | CH₂CH₃ | 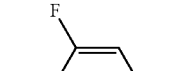 |
| Y.032 | SCF₃ | CH₂CH₃ | 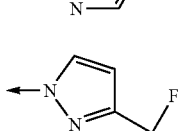 |
| Y.033 | CF₂CF₃ | CH₂CH₃ | 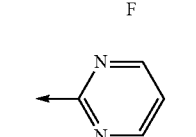 |
| Y.034 | CF₂CF₃ | CH₂CH₃ | 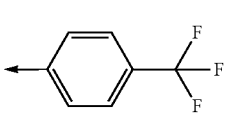 |
| Y.035 | CF₂CF₃ | CH₂CH₃ |  |
| Y.036 | SCF₃ | CH₂CH₃ | 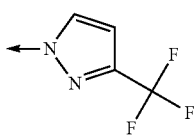 |
| Y.037 | CF₃ | CH₂CH₃ | 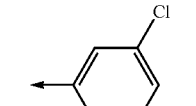 |
| Y.038 | CF₃ | CH₂CH₃ | 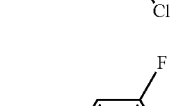 |
| Y.039 | CF₃ | CH₂CH₃ | 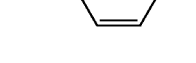 |
| Y.040 | SCF₃ | CH₂CH₃ | 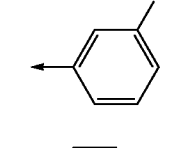 |

TABLE Y-continued

| Comp. No | R$_2$ | Ra$_1$ | Q$_{Rx}$ |
|---|---|---|---|
| Y.041 | SCF$_3$ | CH$_2$CH$_3$ | 4-(trifluoromethyl)pyridin-2-yl |
| Y.042 | SCF$_3$ | CH$_2$CH$_3$ | 3-chloro-1H-pyrazol-1-yl |
| Y.043 | CF$_3$ | CH$_2$CH$_3$ | (3,5-difluorophenyl)ethynyl |
| Y.044 | CF$_3$ | CH$_2$CH$_3$ | prop-2-ynenitrile derivative | and the N-oxides of the compounds of Table Y.

Table 4:
This table discloses the 44 compounds 4.001 to 4.044 of the formula I-2a, wherein Xa$_2$ is S, and Ra$_2$, R$_2$ and Q$_{Rx}$ are as defined in Table Y.

Table 5:
This table discloses the 44 compounds 5.001 to 5.044 of the formula I-2a, wherein Xa$_2$ is SO, and Ra$_2$, R$_2$ and Q$_{Rx}$ are as defined in Table Y.

Table 6:
This table discloses the 44 compounds 6.001 to 6.044 of the formula I-2a, wherein Xa$_2$ is SO$_2$, and Ra$_2$, R$_2$ and Q$_{Rx}$ are as defined in Table Y.

The compounds of formula I according to the invention are preventively and/or curatively valuable active ingredients in the field of pest control, even at low rates of application, which have a very favourable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate.

Examples of the abovementioned Animal Pests are:
from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizogly-phus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*; *Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nip-*

*polachnus piri* Mats, *Odonaspis ruthae, Oregma lanigera* Zehnter, *Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplo-campa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. *B. elatior, B. semperflorens, B. tubéreux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. Walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale*), *Viola* spp. (*pansy*), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*),

*Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba*.

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cystforming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); *ochlodina; Deroceras* (*D. agrestis, D. empiricorum, D. laeve, D. reticulatum*); *Discus* (*D. rotundatus*); *Euomphalia; Galba* (*G. trunculata*); *Helicelia* (*H. itala, H. obvia*) Helicidae *Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides*.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium, Anthracnose*, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store ambients and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO 2006/128870, EP 1724392, WO 2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against wood borers listed in the following tables A and B:

TABLE A

Examples of exotic woodborers of economic importance.

| Family | Species | Host or Crop Infested |
| --- | --- | --- |
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
| --- | --- | --- |
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |

TABLE B-continued

Examples of native woodborers of economic importance.

| Family | Species | Host or Crop Infested |
| --- | --- | --- |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus* verstitus and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs. The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* Spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp.,

*Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylpheno-xypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In general, the pre-mix compositions of the invention contain 0.5 to 99.9 especially 1 to 95, advantageously 1 to 50%, by mass of the desired ingredients, and 99.5 to 0.1, especially 99 to 5%, by mass of a solid or liquid adjuvant (including, for example, a solvent such as water), where the auxiliaries (or adjuvant) can be a surfactant in an amount of 0 to 50, especially 0.5 to 40%, by mass based on the mass of the pre-mix formulation.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.

Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

PREPARATORY EXAMPLES

Example H1: 2-[2-ethylsulfonyl-4-[3-(trifluoromethyl)pyrazol-1-yl]phenyl]-7-(trifluoromethyl)imidazo[1,2-c]pyrimidine (Compound P1, Table P)

(Compound P1, Table P)

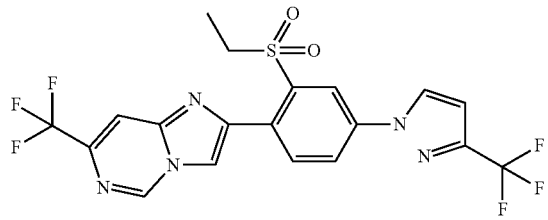

Step A:
1-(4-bromo-2-ethylsulfanyl-phenyl)ethanone

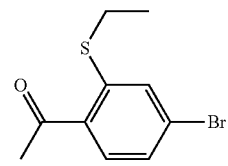

To a solution of 1-(4-bromo-2-fluoro-phenyl)ethanone (0.6 g, 2.76 mmol, CAS [625446-22-2]) in THF (5 mL) was added NaSEt (0.31 g, 3.32 mmol) portionwise, and finally a few crystals of 18-Crown-6. The reaction mixture was stirred 1 hour at −10° C. and 1 hour at ambient temperature. LCMS analysis after this time showed reaction completion. The reaction mixture was diluted with saturated aqueous NH$_4$Cl (30 ml) followed by water (5 ml) and ethyl acetate (20 ml). The organic layer was decanted and the aqueous phase back extracted with ethyl acetate (2×30 ml). The organic layer was washed with water and brine, dried over Na$_2$SO$_4$, filtered and concentrated in vacuo to give the title product as yellow solid which was used in the next step without further purification.

LCMS (method 1); Rt=1.03 min, [M+H] 259/261. $^1$H NMR (400 MHz, chloroform-d) δ ppm: 1.39 (t, J=7.52 Hz, 3H); 2.60 (s, 3H); 2.93 (q, J=7.58 Hz, 2H); 7.32 (dd, J=8.44, 1.83 Hz, 1H); 7.47 (d, J=1.83 Hz, 1H); 7.66 (d, J=8.44 Hz, 1H).

Step B: 1-[2-ethylsulfanyl-4-[3-(trifluoromethyl) pyrazol-1-yl]phenyl]ethanone

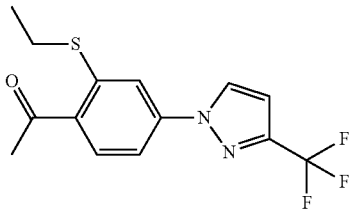

In a Supelco vial, copper(I) iodide (0.038 g, 0.193 mmol), N,N'-dimethylethane-1,2-diamine, (0.034 g, 0.042 ml, 0.39 mmol) and potassium carbonate (0.108 g, 0.77 mmol) were added to a solution of 3-(trifluoromethyl)-1h-pyrazole (0.58 g, 4.24 mmol) and 1-(4-bromo-2-ethylsulfanyl-phenyl)ethanone (1.0 g, 3.86 mmol) in dimethyl formamide (4 ml). The resulting mixture was stirred at 120° C. under an argon atmosphere for 12 hours. LCMS after this time showed incomplete reaction and thus N,N'-dimethylethane-1,2-diamine, (0.034 g, 0.042 ml, 0.39 mmol) and potassium carbonate (0.108 g, 0.77 mmol) were added and the resulting mixture stirred one for a further 12 hours at 120° C. The crude reaction mixture (containing DMF) was purified by directly Combi flash chromatography using a column of 24 g and a gradient cyclohexane 0-30% ethyl acetate to give the title compound.

LCMS (method 1); Rt=1.08 min, [M+H] 315. $^1$H NMR (400 MHz, chloroform-d) δ ppm 1.44 (t, J=7.34 Hz, 3H); 2.66 (s, 3H); 3.03 (q, J=7.58 Hz, 2H); 6.78 (d, J=2.57 Hz, 1H); 7.47 (dd, J=8.44, 2.20 Hz, 1H); 7.77 (d, J=2.20 Hz, 1H); 7.94 (d, J=8.44 Hz, 1H); 8.03 (dd, J=2.57, 0.73 Hz, 1H).

Step C: 1-[2-ethylsulfonyl-4-[3-(trifluoromethyl) pyrazol-1-yl]phenyl]ethanone

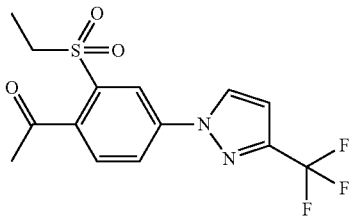 [SMILES: CCS(=O)(=O)c1cc(-n2ccc(C(F)(F)F)n2)ccc1C(C)=O]

In a three neck flask under rargon, 1-[2-ethylsulfanyl-4-[3-(trifluoromethyl)pyrazol-1-yl]phenyl]ethanone (1.02 g, 2.92 mmol) was dissolved in dichloromethane (20 ml) and cooled down to 0° C. To this solution was added meta-chloroperbenzoic acid (1.51 g, 6.13 mmol) and the reaction stirred for 30 min at 0° C., then allowed to warm to ambient temperature and stirred for 18 hours. The reaction mixture was quenched with 1M aqueous sodium hydroxide (10 ml) and saturated aqueous sodium thiosulfate (5 ml). The aqueous layer was extracted 3 times with dichloromethane and the combined organic phases washed successively with 1M aqueous sodium hydroxide (10 ml), 1M aqueous HCl, and brine, dried over Na$_2$SO$_4$, filtered and concentrated in vacuo to give the title compound as a yellow oil.

LCMS (method 1); Rt=0.94 min, [M+H] 347. $^1$H NMR (400 MHz, CHLOROFORM-d) δ ppm 1.37 (t, J=7.34 Hz, 3H); 2.69 (s, 3H); 3.48 (q, J=7.34 Hz, 2H); 6.82 (d, J=2.57 Hz, 1H); 7.62 (d, J=8.44 Hz, 1H); 8.08-8.13 (m, 1H); 8.16 (dd, J=8.44, 2.20 Hz, 1H); 8.30 (d, J=2.20 Hz, 1H).

Step D: 2-bromo-1-[2-ethylsulfonyl-4-[3-(trifluoromethyl)pyrazol-1-yl]phenyl]ethanone

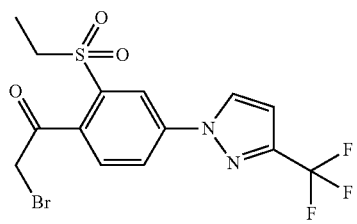 [SMILES: CCS(=O)(=O)c1cc(-n2ccc(C(F)(F)F)n2)ccc1C(=O)CBr]

A solution of 1-[2-ethylsulfonyl-4-[3-(trifluoromethyl) pyrazol-1-yl]phenyl]ethanone (0.9 g, 2.599 mmol) in chloroform (4.5 ml) and ethyl acetate (4.5 ml) in Supelco microwave vial, was treated with copper(II)bromide (1.16 g, 5.2 mmol) and the reaction mixture was stirred in the microwave for 50 min at 140° C. After this time, the reaction mixture was diluted with ethyl acetate, washed with water, the organic phase dried over Na$_2$SO$_4$, filtered and concentrated in vacuo. Purification by Combi flash chromatography with a column of 24 g and a gradient of cyclohexane 0-60% ethyl acetate gave the title compound as a white solid.

LCMS (method 1); Rt=1.01 min, [M+H] 425/427. $^1$H NMR (400 MHz, CHLOROFORM-d) δ ppm 1.36 (t, J=7.52 Hz, 3H); 3.35 (q, J=7.34 Hz, 2H); 4.50 (s, 2H); 6.83 (d, J=2.93 Hz, 1H); 7.69 (d, J=8.44 Hz, 1H); 8.12 (dd, J=2.57, 0.73 Hz, 1H); 8.17 (dd, J=8.44, 2.20 Hz, 1H); 8.32 (d, J=2.20 Hz, 1H).

Step D: 2-[2-ethylsulfonyl-4-[3-(trifluoromethyl) pyrazol-1-yl]phenyl]-7-(trifluoromethyl)imidazo[1, 2-c]pyrimidine Compound (P1, Table P)

(Compound P1, Table P)

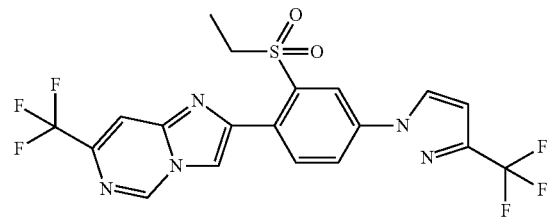

A solution of 6-(trifluoromethyl)pyrimidin-4-amine (0.143 g, 0.877 mmol) and 2-bromo-1-[2-ethylsulfonyl-4-[3-(trifluoromethyl)pyrazol-1-yl]phenyl]ethanone (0.34 g, 0.80 mmol) in acetonitrile (7 ml) in a Supelco microwave vial, was stirred for 1 hr at 150° C. LC-MS showed the desired product and starting material. The reaction was thus stirred 1 hour more at 150° C. after which LCMS showed more product, less starting material. After a further 1 hour at 150° C. the reaction mixture was diluted with ethyl acetate, dried over Na₂SO₄, filtered and concentrated in vacuo. The crude product was purified by Combi flash chromatography with a column of 12 g and a gradient cyclohexane 0-60% ethyl acetate, to give the title compound as a beige solid.

LCMS (method 1); Rt=1.05 min, [M+H] 425/427.

¹H NMR (400 MHz, CHLOROFORM-d) δ ppm 1.26 (t, J=7.34 Hz, 3H); 3.37 (q, J=7.34 Hz, 2H); 6.84 (d, J=2.57 Hz, 1H); 7.96 (d, J=8.44 Hz, 1H); 7.98 (s, 1H); 8.16 (d, J=1.83 Hz, 1H) 8.24 (dd, J=8.44, 2.20 Hz, 1H) 8.33 (s, 1H) 8.52 (d, J=2.57 Hz, 1H) 9.19 (s, 1H)

Example H2: 2-[2-ethylsulfonyl-4-[4-(trifluoromethyl)phenyl]phenyl]-7-(trifluoromethyl)imidazo[1,2-c]pyrimidine (compound P2, Table P)

(Compound P2, Table P)

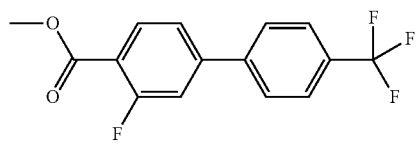 [SMILES: COC(=O)c1ccc(-c2ccc(C(F)(F)F)cc2)cc1F]

Step A: Methyl 2-fluoro-4-[4-(trifluoromethyl)phenyl]benzoate

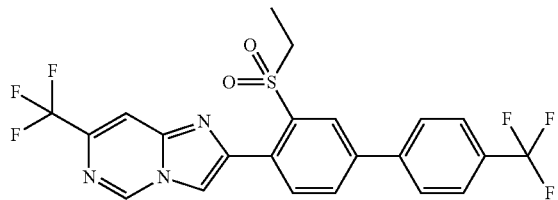

Methyl 4-bromo-2-fluoro-benzoate (1.92 g, 8.24 mmol, CAS [179232-29-2]) was dissolved in 1,4-dioxane (48.0 mL). To this solution was added [4-(trifluoromethyl)phenyl]boronic acid (2.03 g, 1.30 eq, 10.7 mmol) and potassium carbonate (3.42 g, 24.7 mmol) and the mixture was purged with argon for 10 min. To this was added Pd(PPh₃)₄ (0.954 g, 0.824 mmol) and the brown solution was heated at 100° C. for 17 hr. The reaction mixture was then diluted with saturated aqueous NH₄Cl, water and ethyl acetate. The organic layer was separated, washed with brine, dried over Na₂SO₄, filtered concentrated in vacuo at 40° C. to give a yellow solid. The crude product was dissolved in dichloromethane, adsorbed on Teflon Bulk Sorbents and then purified over a silica gel cartridge (Rf200) eluting with cyclohexane/ethyl acetate, to give the title product as a yellow solid.

LCMS (method 1); Rt=1.19 min, [M+H] 299. ¹H NMR (400 MHz, CHLOROFORM-d) δ ppm 1.26 (t, J=7.15 Hz, 2H); 3.96 (s, 3H); 4.12 (q, J=6.97 Hz, 1H); 7.34-7.41 (m, 1H); 7.44 (dd, J=8.07, 1.83 Hz, 1H); 7.66-7.77 (m, 4H); 8.04 (t, J=7.70 Hz, 1H).

Step B: 2-fluoro-4-[4-(trifluoromethyl)phenyl]benzoic Acid

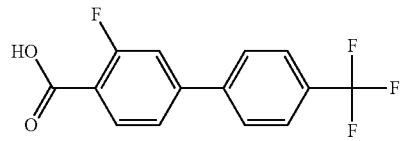

Methyl 2-fluoro-4-[4-(trifluoromethyl)phenyl]benzoate (1.5 g, 5.0 mmol) was dissolved in tetrahydrofurane/H₂O 3:1 (53 mL) and the yellow, clear solution treated with lithium hydroxide hydrate (0.22 g, 5.3 mmol) at ambient temperature. The reaction was complete within 2 hours at this temperature. The reaction mixture was partially concentrated in vacuo, and the remaining solution acidified with 1N HCl, and extracted with ethyl acetate, the organic phase dried over Na₂SO₄, filtered concentrated in vacuo to give the title compound as a white solid, Mpt: 231-233° C.

LCMS (method 1); Rt=1.00 min, [M−H] 283. ¹H NMR (400 MHz, DMSO-d₆) δ ppm 7.55 (d, J=8.44 Hz, 2H); 7.77 (br. s., 1H); 7.82 (d, J=8.44 Hz, 2H); 7.95 (d, J=8.07 Hz, 2H).

Step C: 2-fluoro-N-methoxy-N-methyl-4-[4-(trifluoromethyl)phenyl]benzamide

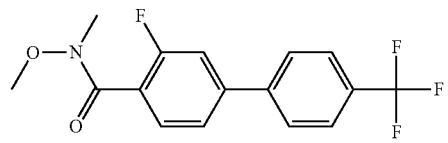 [SMILES: CON(C)C(=O)c1ccc(-c2ccc(C(F)(F)F)cc2)cc1F]

Methyl 2-fluoro-4-[4-(trifluoromethyl)phenyl]benzoate (1.3 g, 4.6 mmol) was dissolved in dichloromethane (26 mL) under an argon atmosphere. To this were added 2 drops of dimethylformamide and then oxalyl chloride (0.75 g, 0.50 mL, 5.9 mmol). The reaction was stirred for 3 hr at ambient temperature by which time LCMS analysis of an aliquot treated with MeOH showed complete conversion to 2-fluoro-4-[4-(trifluoromethyl)phenyl]benzoyl chloride had occurred. The reaction mixture was concentrated in vacuo and used without further purification in the next step. A suspension of N-methoxymethanamine hydrochloride (0.3308 g, 3.392 mmol) was dissolved in a mixture of dry dichloromethane/THF (23.325 mL) under argon. The suspension was cooled to 0° C. and treated with pyridine (0.7317 g, 0.744 mL, 9.250 mmol). To this suspension was added 2-fluoro-4-[4-(trifluoromethyl)phenyl]benzoyl chloride (0.933 g, 3.083 mmol) dissolved in 10 ml of tetrahydrofurane, dropwise at 0° C. The reaction mixture was stirred 1 h at 0° C. then 2 days at rt. After this time, the reaction mixture was The reaction mixture was diluted with saturated aqueous NH₄Cl and the aqueous layer was extracted (×2) times with ethyl acetate. The combined organic layers were washed successively with water and brine, dried over Na₂SO₄, filtered and evaporated in vacuo to give the crude product. This was purified by Combi flash with a column of 24 g and a gradient cyclohexane +0-70% ethyl acetate, to give the title compound as a white solid.

LCMS (method 1); Rt=1.04 min, [M+H] 328. ¹H NMR (400 MHz, CHLOROFORM-d) δ ppm 3.39 (s, 3H); 3.62 (br. s., 3H), 7.35 (dd, J=10.45, 1.65 Hz, 1H), 7.44 (dd, J=8.07, 1.47 Hz, 1H), 7.51-7.59 (m, 1H), 7.67-7.78 (m, 4H).

Step D: 1-[2-fluoro-4-[4-(trifluoromethyl)phenyl]phenyl]ethanone

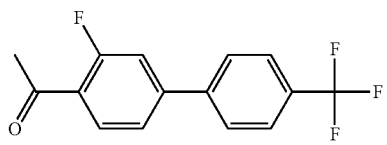 [SMILES: CC(=O)c1ccc(-c2ccc(C(F)(F)F)cc2)cc1F]

A solution of bromo(methyl)magnesium (1.4 M in THF:Toluene 1:3 (1.2 mL, 1.680 mmol) in dry toluene (7.5 mL) was cooled to 0° C. and treated with 2-fluoro-N-methoxy-N-methyl-4-[4-(trifluoromethyl)phenyl]benzamide (0.5 g, 1.528 mmol) dissolved in 3 ml of toluene. The now red reaction mixture was stirred 30' at 0° C. and then 1 hour at ambient temperature. LCMS analysis after this time showed reaction completion. The reaction mixture was slowly quenched with saturated aqueous NH₄Cl and HCl 10% (30 ml) and the resulting mixture vigorously stirred for 15' at ambient temperature. The aqueous layer was extracted with ethyl acetate (×2). The organic phase was washed successively with 10% HCl aq sol, water and brine, dried over Na₂SO₄, filtered and concentrated in vacuo. The crude product was purified by Combi flash with a column of 12 g and a gradient cyclohexane +0-40% ethyl acetate to give the title compound as a white solid.

LCMS (method 1); Rt=1.00 min, [M+H] 283. ¹H NMR (400 MHz, CHLOROFORM-d) δ ppm 2.70 (d, J=5.14 Hz, 3H); 7.39 (dd, J=11.92, 1.65 Hz, 1H); 7.48 (dd, J=8.07, 1.83 Hz, 1H); 7.68-7.78 (m, 4H); 8.00 (t, J=7.89 Hz, 1H).

Step E: 1-[2-ethylsulfanyl-4-[4-(trifluoromethyl)phenyl]phenyl]ethanone

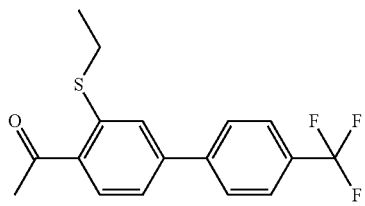 [SMILES: CCSc1cc(-c2ccc(C(F)(F)F)cc2)ccc1C(C)=O]

1-[2-fluoro-4-[4-(trifluoromethyl)phenyl]phenyl]ethanone (300 mg, 1.063 mmol) was dissolved in dimethylformamide (9 mL) and treated with NaSEt (109.3 mg, 1.169 mmol) at 0° C. The reaction mixture was stirred 30' at 0° C., and shown by LCMS to be complete. The reaction mixture was quenched with water and tert-butyl methyl ether (TBME) was added. The aqueous layer was back extracted 2 times with TBME and the combined organic layers washed successively with water (2 times), brine, dried over Na₂SO₄, filtered and concentrated in vacuo. This gave the title compound as a yellow solid (Mpt. 108-109° C.) which was used in the next step without further purification.

¹H NMR (400 MHz, CHLOROFORM-d) δ ppm 1.42 (t, J=7.34 Hz, 3H); 2.67 (s, 3H); 3.01 (q, J=7.34 Hz, 2H); 7.40 (dd, J=8.07, 1.83 Hz, 1H); 7.54 (d, J=1.83 Hz, 1H); 7.69-7.73 (m, 2H); 7.73-7.77 (m, 2H); 7.90 (d, J=8.07 Hz, 1H).

Step F: 1-[2-ethylsulfonyl-4-[4-(trifluoromethyl)phenyl]phenyl]ethanone

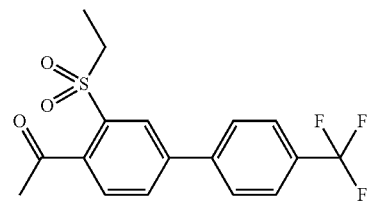 [SMILES: CCS(=O)(=O)c1cc(-c2ccc(C(F)(F)F)cc2)ccc1C(C)=O]

A solution of 1-[2-ethylsulfanyl-4-[4-(trifluoromethyl)phenyl]phenyl]ethanone (0.3 g, 0.9248 mmol) in dichloromethane (9 mL) was cooled to 0° C. and treated with meta-chloroperbenzoic acid (0.4560 g, 1.850 mmol). The reaction was stirred 30' at 0° C. and then warmed up at ambient temperature and stirred over night. After this time, the reaction mixture was quenched with NaOH 1 M (5 ml) and sodium thiosulfate sol (3 ml). The aqueous layer was extracted 3 times with dichloromethane and the combined organic phases washed successively with NaOH 1M, brine, dried over Na₂SO₄, filtered and concentrated in vacuo. The crude product was purified by Combi flash chromatography with a column of 12 g and a gradient cyclohexane +0-55% ethyl acetate, yielding the title product as a white solid.

LCMS (method 1); Rt=1.04 min, [M+H] 357. ¹H NMR (400 MHz, CHLOROFORM-d) δ ppm 1.35 (t, J=7.52 Hz, 3H); 2.70 (s, 3H); 3.44 (q, J=7.58 Hz, 2H); 7.55-7.61 (m, 1H); 7.71-7.80 (m, 4H); 7.91 (dd, J=7.70, 1.83 Hz, 1H); 8.25 (d, J=1.83 Hz, 1H).

Step G: 2-bromo-1-[2-ethylsulfonyl-4-[4-(trifluoromethyl)phenyl]phenyl]ethanone

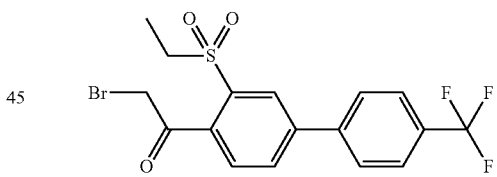

1-[2-ethylsulfonyl-4-[4-(trifluoromethyl)phenyl]phenyl]ethanone (0.29 g, 0.8137 mmol) was dissolved in chloroform (1.45 mL) and ethyl acetate (1.45 mL) in microwave vial and treated with copper(II)bromide (0.2726 g). The reaction mixture was then stirred in the microwave for 1 h at 140° C. After this time a further 0.5 eq of CuBr₂ was added and reaction mixture was stirred in the microwave 1 h at 140° C. After this time the reaction mixture was dissolved in ethyl acetate, dried over Na₂SO₄, filtered and concentrated in vacuo. The crude was purified by Combi flash chromatography with a column of 24 g and a gradient cyclohexane +0-20% ethyl acetate to give the title compound.

LCMS (method 1); Rt=1.08 min, [M−H] 433/435. ¹H NMR (400 MHz, CHLOROFORM-d) δ ppm 1.34 (t, J=7.34 Hz, 3H); 3.32 (q, J=7.58 Hz, 2H); 4.53 (s, 2H); 7.65 (d, J=7.70 Hz, 1H); 7.72-7.82 (m, 4H); 7.94 (dd, J=8.07, 1.83 Hz, 1H); 8.23 (d, J=1.83 Hz, 1H).

Step H: 2-[2-ethylsulfonyl-4-[4-(trifluoromethyl)phenyl]phenyl]-7-(trifluoromethyl)imidazo[1,2-c]pyrimidine (Compound P2, Table P)

(compound P2, Table P)

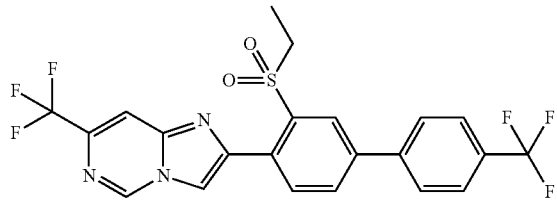

In a Supelco microwave vial, 6-(trifluoromethyl)pyrimidin-4-amine (0.1321 g, 0.8098 mmol) and 2-bromo-1-[2-ethylsulfonyl-4-[4-(trifluoromethyl)phenyl]phenyl]ethanone (0.235 g, 0.5399 mmol) were dissolved in acetonitrile (4.7 mL). The resulting mixture was stirred 1 hour at 150° C. LCMS analysis showed the desired product and starting material. This was procedure was repeated a further three times so the total time heating was 4 hours at 150° C. The reaction mixture was concentrated in vacuo and the residue dissolved in ethyl acetate, which was successively washed with saturated aqueous NaHCO$_3$, brine, dried over Na$_2$SO$_4$, filtered and concentrated in vacuo. The crude protected was purified by Combi flash chromatography with a column of 12 g and a gradient cyclohexane +0-50% EtOAc, to give the title compound as a white solid (Mpt. 179-180° C.).

LCMS (method 1); Rt=1.13 min, [M+H] 500. $^1$H NMR (400 MHz, CHLOROFORM-d) δ ppm 1.28 (t, J=7.34 Hz, 3H); 3.41 (m, J=7.34 Hz, 2H); 7.47-7.68 (m, 6H); 8.01 (dd, J=7.89, 2.02 Hz, 1H); 8.10 (d, J=1.10 Hz, 1H); 8.39 (d, J=1.83 Hz, 1H); 8.96 (s, 1H).

Example H3: 2-[3-ethylsulfonyl-5-[3-(trifluoromethyl)pyrazol-1-yl]-2-pyridyl]-7-(trifluoromethyl)imidazo[1,2-c]pyrimidine (Compound P4, Table P)

(Compound P4, Table P)

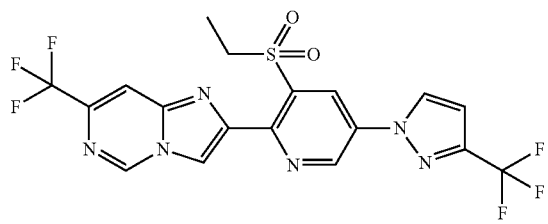

Step A:
5-bromo-3-ethylsulfanyl-pyridine-2-carbonitrile

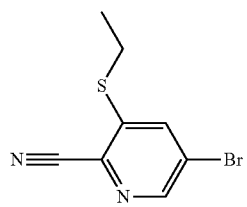

5-bromo-3-nitro-pyridine-2-carbonitrile (75 g, 0.329 mol, prepared as described in *J. Org Chem,* 74, 4547-4553; 2009) was dissolved in N,N-dimethylformamide (1.3 L) and cooled to −40° C. This yellow solution was treated portionwise with NaSEt (36.3 g, 0.345 mol), and then allowed to warm to ambient temperature. After 12 hours stirring at ambient temperature, the reaction was complete (LCMS analysis). The reaction mixture was diluted with AcOEt, and quenched with water. The organic layer was washed with water, and then dried over sodium sulfate and concentrated in vacuo. Purification using a Torrent machine, eluting with Cyclohexane/EA gradient gave the title product as orange crystals. LCMS (method 1); Rt=0.95 min, [M+H] 243/245. $^1$H NMR (400 MHz, CHLOROFORM-d) δ ppm: 1.42 (t, J=7.34 Hz, 3H); 3.08 (q, J=7.34 Hz, 2H); 7.84 (d, J=1.83 Hz, 1H); 8.50 (d, J=1.83 Hz, 1H).

Step B:
5-bromo-3-ethylsulfanyl-pyridine-2-carboxylic Acid

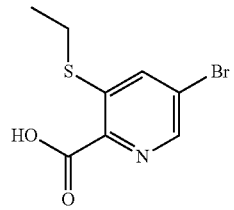

A solution of 5-bromo-3-ethylsulfanyl-pyridine-2-carbonitrile (61 g, 240.87 mmol) in concentrated hydrochloric acid (1132 mL) and 50 ml of Dioxane was heated to 60° C., and stirred for 12 hours. LCMS analysis after this time showed reaction completion. The reaction mixture was cooled to 0°-5° C., treated with NaOH 30% aqueous solutions until pH11, and then extracted with ethyl acetate (2×300 ml). The water phase was acidified with HCl conc. to pH4, and the solid filtered, washed with water and dried in vacuo. This gave the title compound as beige solid. LCMS (method 1); Rt=0.77 min, [M+H] 262/264. $^1$H NMR (400 MHz, DMSO-d$_6$) δ ppm: 1.25 (t, J=7.34 Hz, 3H); 3.03 (q, J=7.34 Hz, 2H); 8.06 (d, J=2.20 Hz, 1H); 8.50 (d, J=1.83 Hz, 1H); 13.40 (br. s., 1H).

Step C: 5-bromo-3-ethylsulfanyl-N-methoxy-N-methyl-pyridine-2-carboxamide

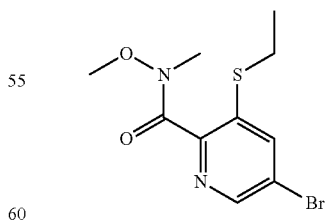

At ambient temperature, a solution of 5-bromo-3-ethylsulfanyl-pyridine-2-carboxylic acid (2 g, 7.63 mmol) in dichloromethane (30 mL) was treated with oxalyl dichloride (1.259 g, 9.92 mmol) and then 2-3 drops of a dimethylformamide (formation of gas). The reaction mixture was stirred at ambient temperature until the gas evolution ceased, and then the solvent was removed by evaporation. The residue, 5-bromo-3-ethylsulfanyl-pyridine-2-carbonyl chloride (1.82 g, 6.49 mmol) was dissolved in dichloromethane (10 mL) and added to a solution of N-methoxymethanamine hydrochloride (0.633 g, 6.49 mmol) and triethylamine (1.66 g, 2.28 mL, 16.2 mmol) in with dichloromethane (27.3 mL) at 0° C. under argon. The reaction mixture was allowed to warm to ambient temperature and stirred until reaction completion. The reaction mixture was quenched with water, the organic layer was separated, and the aqueous layer back extracted with dichloromethane (×2). The combined organic layers were washed with water, dried over Na$_2$SO$_4$, filtered and concentrated in vacuo. The crude product was purified by Combi flash chromatography with a column of 40 g and a gradient cyclohexane +0-60% ethyl acetate, to give the title compound as a beige solid. Mpt 69-71° C. LCMS (method 1); Rt=0.77 min, [M+H] 305/307. $^1$H NMR (400 MHz, chloroform-d) δ ppm: 1.33 (t, J=7.52 Hz, 3H); 2.96 (q, J=7.34 Hz, 2H); 3.39 (br. s., 3H); 3.58 (br. s., 3H); 7.84 (d, J=1.83 Hz, 1H); 8.47 (d, J=1.83 Hz, 1H).

Step D: 1-(5-bromo-3-ethylsulfanyl-2-pyridyl)ethanone

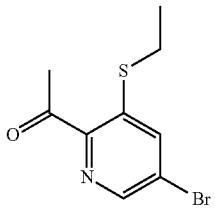

A solution of bromo(methyl)magnesium (1.4 mol/L in THF: toluene (1:3), 7.8 mL, 10.9 mmol) in toluene (42 mL) was cooled to 0° C. and a solution of 5-bromo-3-ethylsulfanyl-N-methoxy-N-methyl-pyridine-2-carboxamide (2.78 g, 9.11 mmol) in 10 mL of Toluene was added dropwise at this temperature. The reaction was then allowed to warm to ambient temperature and stirred for 1 hour. LCMS analysis after this time showed reaction completion. The crude was slowly quenched with NH$_4$Cl sat aq (20 ml) and HCl 10% (10 ml) and the resulting mixture was vigorously stirred for 15 min at ambient temperature. The aqueous layer was extracted twice with ethyl acetate and the combined organic phases was successively with 10% HCl aq sol, water and brine, dried over Na$_2$SO$_4$, filtered and concentrated in vacuo. This gave the title compound which was used without further purification in the next step. LCMS (method 1); Rt=1.01 min, [M+H] 260/262. $^1$H NMR (400 MHz, CHLOROFORM-d) δ ppm: 1.42 (t, J=7.34 Hz, 3H); 2.68 (s, 3H); 2.91 (q, J=7.34 Hz, 2H); 7.77 (d, J=2.20 Hz, 1H); 8.42 (d, J=2.20 Hz, 1H).

Step E: 1-[3-ethylsulfanyl-5-[3-(trifluoromethyl) pyrazol-1-yl]-2-pyridyl]ethanone

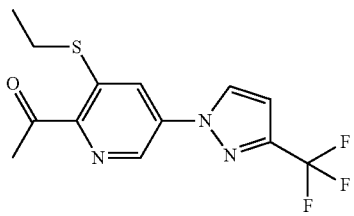 [SMILES: CCSc1cc(-n2ccc(C(F)(F)F)n2)cnc1C(C)=O]

In a supelco vial, copper(I)iodide (0.110 g, 0.561 mmol) N,N'-dimethylethane-1,2-diamine (0.0989 g, 1.12 mmol) and potassium carbonate (0.313 g, 2.24 mmol) were added to a solution of 3-(trifluoromethyl)-1 h-pyrazole (0.840 g, 6.17 mmol) and 1-(5-bromo-3-ethylsulfanyl-2-pyridyl)ethanone (1.46 g, 5.61 mmol.) in dimethylformamide (6 mL). The resulting mixture was stirred at 120° C. under an argon atmosphere for 48 h. Aqueous work-up and purification of the crude by Combi flash chromatography with a column of 24 g and a gradient cyclohexane 0-30% ethylacetate gave the title compound as a white solid. LCMS (method 1); Rt=1.09 min, [M+H] 316. $^1$H NMR (400 MHz, CHLOROFORM-d) δ ppm: 1.40 (t, J=7.52 Hz, 3H); 4.00 (q, J=7.46 Hz, 2H); 7.97 (s, 1H); 8.36 (s, 1H); 8.69 (d, J=2.20 Hz, 1H); 8.95 (d, J=2.20 Hz, 1H); 9.17 (s, 1H).

Step F: 1-[3-ethylsulfonyl-5-[3-(trifluoromethyl) pyrazol-1-yl]-2-pyridyl]ethanone

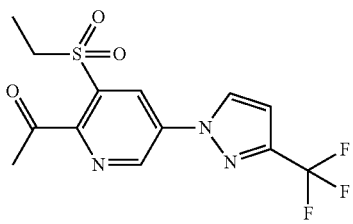 [SMILES: CCS(=O)(=O)c1cc(-n2ccc(C(F)(F)F)n2)cnc1C(C)=O]

A solution of 1-[3-ethylsulfanyl-5-[3-(trifluoromethyl) pyrazol-1-yl]-2-pyridyl]ethanone (1.36 g, 3.88 mmol) in dichloromethane (27 mL) was cooled to 0° C. and treated portionwise with meta-chloroperoxybenzoic acid (1.79 g, 7.76 mmol). The reaction mixture was stirred for 30 min at 0° C. then warmed up to ambient temperature and stirred for a further 3 hours. Reaction mixture was quenched with NaOH 1 M (10 ml) and sodium thiosulfate sol (5 ml). The aqueous layer was extracted 3 times with dichloromethane. The combined organic layer was washed successively with NaOH 1M, and brine, dried over Na$_2$SO$_4$, filtered and concentrated in vacuo. This gave the title compound as a yellow solid. Mpt: 82-84° C.

LCMS (method 1); Rt=0.96 min, [M+H] 348. $^1$H NMR (400 MHz, CHLOROFORM-d) δ ppm 1.40 (t, J=7.52 Hz, 3H) 2.76 (s, 3H) 3.68 (q, J=7.34 Hz, 2H) 6.87 (d, J=2.57 Hz, 1H) 8.15 (dd, J=2.75, 0.92 Hz, 1H) 8.68 (d, J=2.57 Hz, 1H) 9.27 (d, J=2.57 Hz, 1H).

Step G: 2-bromo-1-[3-ethylsulfonyl-5-[3-(trifluoromethyl)pyrazol-1-yl]-2-pyridyl]ethanone

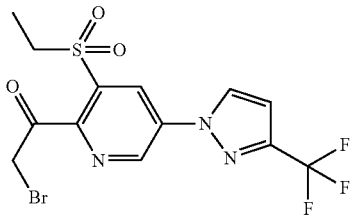 [SMILES: CCS(=O)(=O)c1cc(-n2ccc(C(F)(F)F)n2)cnc1C(=O)CBr]

A solution of 1-[3-ethylsulfonyl-5-[3-(trifluoromethyl) pyrazol-1-yl]-2-pyridyl]ethanone (1.03 g, 2.97 mmol) in chloroform (5 mL) and ethyl acetate (5 mL) was placed in a microwave vial and copper(II) bromide (0.994 g, 4.45 mmol) was added. The reaction mixture was stirred in the microwave for 50 min at 140° C. The reaction mixture was then dissolved in ethyl acetate, dried over Na₂SO₄, filtered and concentrated in vacuo. The crude product was purified by reversed phase flash chromatography to give the title compound as a white solid.

LCMS (method 1); Rt=1.01 min, [M+H] 426/428. ¹H NMR (400 MHz, CHLOROFORM-d) δ ppm: 1.42 (t, J=7.52 Hz, 3H); 3.71 (q, J=7.70 Hz, 2H); 4.78 (s, 2H); 6.89 (d, J=2.57 Hz, 1H); 8.14-8.22 (m, 1H); 8.74 (d, J=2.57 Hz, 1H).

Step H: 2-[3-ethylsulfonyl-5-[3-(trifluoromethyl)pyrazol-1-yl]-2-pyridyl]-7-(trifluoromethyl)imidazo[1,2-c]pyrimidine (Compound P4, Table P)

(Compound P4, table P)

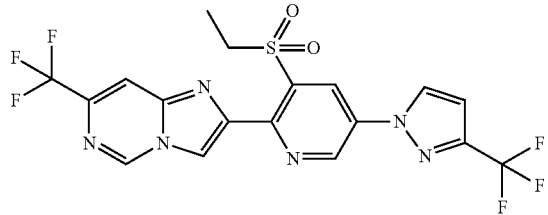

A solution of 6-(trifluoromethyl)pyrimidin-4-amine (0.21 g, 1.290 mmol) and 2-bromo-1-[3-ethylsulfonyl-5-[3-(trifluoromethyl)pyrazol-1-yl]-2-pyridyl]ethanone (0.5 g, 1.173 mmol) were in acetonitrile (10 mL) was stirred for 1.5 h at 150° C. in the microwave. The reaction mixture was then dissolved in ethyl acetate, dried over Na₂SO₄, filtered and concentrated in vacuo. The crude product was purified by combi flash chromatography with a column of 40 g and a gradient cyclohexane +0-60% ethyl acetate to give the title compound as a white solid. Mpt: 229-230° C.

LCMS (method 1); LCMS (method 1); Rt=1.01 min, [M+H] 491. ¹H NMR (400 MHz, CHLOROFORM-d) δ ppm 1.47 (t, J=7.52 Hz, 3H); 4.11 (q, J=7.34 Hz, 2H); 6.91 (d, J=2.57 Hz, 1H); 8.02 (s, 1H); 8.20 (dd, J=2.57, 0.73 Hz, 1H); 8.45 (s, 1H); 8.85 (d, J=2.20 Hz, 1H); 9.22 (s, 1H); 9.40 (d, J=2.57 Hz, 1H).

Example H4: 2-[5-(4-chlorophenyl)-3-ethylsulfonyl-2-pyridyl]-7-(trifluoromethyl)imidazo [1,2-c]pyrimidine (Compound P5, Table P)

(Compound P5, Table P)

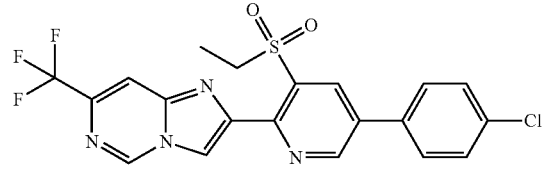

Step A: 1-(5-bromo-3-ethylsulfonyl-2-pyridyl)ethanone

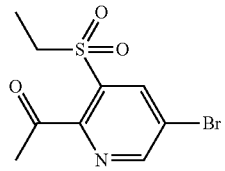

A solution of 1-(5-bromo-3-ethylsulfanyl-2-pyridyl)ethanone (2.31 g, 8.88 mmol, prepared as described in Example H3, step D) in dichloromethane (46 mL) was cooled to 0° C. and treated portionwise with meta-chloroperoxybenzoic acid (4.09 g, 17.8 mmol). The reaction mixture was stirred for 30 min at 0° C. and then allowed to warm to ambient temperature and stirred for a further 3 hr. LCMS analysis after this time showed reaction completion. The reaction mixture was quenched with NaOH 1M (10 mL) and sodium thiosulfate solution (5 mL). The aqueous layer was extracted with dichloromethane (×3) and the combined organic layers washed successively with NaOH 1M, brine, dried over Na₂SO₄, filtered and concentrated in vacuo. The crude product was purified by combi flash chromatography with a column of 40 g and a gradient cyclohexane +0-60% ethylacetate to give the title compound. ¹H NMR (400 MHz, CHLOROFORM-d) δ ppm: 1.42 (t, J=7.34 Hz, 3H); 2.68 (s, 3H); 2.91 (q, J=7.34 Hz, 2H); 7.77 (d, J=2.20 Hz, 1H); 8.42 (d, J=2.20 Hz, 1H).

Step B: 2-bromo-1-(5-bromo-3-ethylsulfonyl-2-pyridyl)ethanone

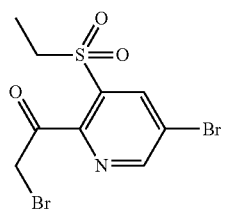 [SMILES: CCS(=O)(=O)c1cc(Br)cnc1C(=O)CBr]

A solution of 1-(5-bromo-3-ethylsulfonyl-2-pyridyl)ethanone (1.7 g, 5.8 mmol) in chloroform (8.5 mL) and acetonitrile (8.5 mL) in a microwave vial was treated with copper(II)bromide (2.6 g, 12 mmol), and the mixture was stirred in the microwave for 55 min at 140° C. After this time, the reaction mixture was dissolved in ethyl acetate, dried over Na₂SO₄, filtered and concentrated in vacuo. The crude product was purified by combi flash chromatography with a column of 24 g and a gradient cyclohexane +0-30% ethyl acetate to give the title compound. LCMS (method 1); Rt=1.01 min, [M+H] 370/372/374. ¹H NMR (400 MHz, chloroform-d) δ ppm: 370/372/374 1.38 (t, J=7.52 Hz, 3H); 3.63 (q, J=7.70 Hz, 2H); 4.72 (s, 2H); 8.58 (d, J=1.83 Hz, 1H); 8.90 (d, J=1.83 Hz, 1H).

Step C: 2-(5-bromo-3-ethylsulfonyl-2-pyridyl)-7-(trifluoromethyl)imidazo[1,2-c]pyrimidine

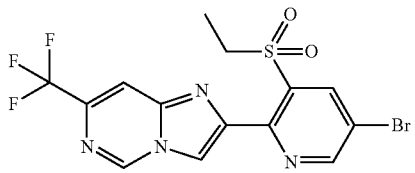 [SMILES: CCS(=O)(=O)c1cc(Br)cnc1-c1cn2cnc(C(F)(F)F)cc2n1]

A solution of 6-(trifluoromethyl)pyrimidin-4-amine (0.14544 g, 0.89175 mmol) and 2-bromo-1-(5-bromo-3-ethylsulfonyl-2-pyridyl)ethanone (0.3 g, 0.81 mmol) in acetonitrile (9 mL) were heated for 1 h at 150° C. in the microwave. After this time, the reaction mixture was evaporated. The solid obtained was dissolved in dichloromethane and washed with NaHCO₃ sat sol. The organic layer was then washed with brine, dried over Na₂SO₄, filtered and concentrated in vacuo. Purification by Combi flash chromatography with a column of 12 g and a gradient of dichloromethane +0-10% ethylacetate gave the title product as white powder.

LCMS (method 1); Rt=0.91 min, [M+H] 435/437. ¹H NMR (400 MHz, chloroform-d) δ ppm: 1.40 (t, J=7.52 Hz, 3H); 4.00 (q, J=7.46 Hz, 2H); 7.97 (s, 1H); 8.36 (s, 1H); 8.69 (d, J=2.20 Hz, 1H); 8.95 (d, J=2.20 Hz, 1H); 9.17 (s, 1H).

Step D: 2-[5-(4-chlorophenyl)-3-ethylsulfonyl-2-pyridyl]-7-(trifluoromethyl)imidazo[1,2-c] pyrimidine (Compound P5, Table P)

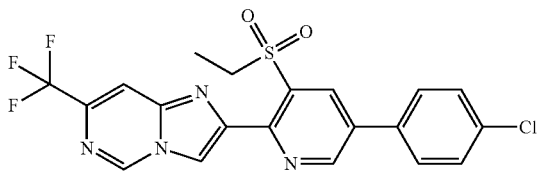

A mixture of 2-(5-bromo-3-ethylsulfonyl-2-pyridyl)-7-(trifluoromethyl)imidazo[1,2-c]pyrimidine (47 mg, 0.08640 mmol), (4-chlorophenyl)boronic acid (0.01621 g, 0.1037 mmol), sodium carbonate (0.2160 mmol), and 1,1-dimethoxyethane (2 mL) were mixed in a vial and argon was bubbled within 5 min through the mixture. To this mixture was added palladium(0) tetrakis(triphenylphosphine) (0.01997 g, 0.01728 mmol) and pale brown mixture was stirred one night at 95° C. The reaction mixture was then diluted with water and extracted with ethyl acetate (2×) and the combined organic layers washed successively with water and brine, dried over Na₂SO₄ and concentrated in vacuo. The crude product was purified by combi flash chromatography with a column of 4 g and a gradient cyclohexane +0-60% ethylacetate, to give the title compound as a white solid. Mpt: 185-187° C.

LCMS (method 1); Rt=0.91 min, [M+H] 467/469. ¹H NMR (400 MHz, CHLOROFORM-d) δ ppm: 1.40 (t, J=7.34 Hz, 3H); 3.97 (q, J=7.58 Hz, 2H); 7.52-7.57 (m, 2H); 7.63-7.68 (m, 2H); 7.99 (s, 1H); 8.42 (s, 1H); 8.71 (d, J=2.20 Hz, 1H); 9.10 (d, J=2.20 Hz, 1H); 9.19 (s, 1H).

Example H5: 2-[3-ethylsulfonyl-5-[4-(trifluoromethyl)phenyl]-2-pyridyl]-7-(trifluoromethyl)imidazo[1,2-c]pyrimidine (Compound P6, Table P)

(compound P6, Table P)

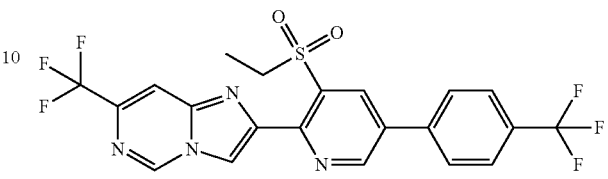

A solution of 2-(5-bromo-3-ethylsulfonyl-2-pyridyl)-7-(trifluoromethyl)imidazo[1,2-c]pyrimidine (0.047 g, 0.1080 mmol), [4-(trifluoromethyl)phenyl]boronic acid (0.0246 g, 0.1296 mmol), and sodium carbonate (0.1350 mL, 0.2700 mmol) in 1,1-dimethoxyethane (2 mL) were placed in a vial and argon was bubbled within 5 min through the mixture. To this degassed solution were added tetrakis palladium (0.02496 g, 0.02160 mmol) and the pale brown mixture was stirred 1 h at 90° C. After 3 hr, further portions of [4-(trifluoromethyl)phenyl]boronic acid (0.0246 g, 0.1296 mmol) and tetrakis palladium (0.02496 g, 0.02160 mmol) were added and reaction mixture was stirred for a further 2 hours at 95° C. The RM was diluted with 10 ml water, and was extracted 2× with EtOAc. The combined organic layers was washed with water, and then brine. Drying over Na₂SO₄ and concentration in vacuo gave the crude product which was purified by combi flash chromatography with a column of 4 g and a gradient cyclohexane +0-60% ethylacetate. Further purification by reverse phase prep HPLC gave the title product as beige solid. Mpt 230-232° C.

LCMS (method 1); Rt=1.08 min, [M+H] 501. ¹H NMR (400 MHz, CHLOROFORM-d) δ ppm: 1.42 (t, J=7.34 Hz, 3H); 4.01 (q, J=7.34 Hz, 2H); 7.84 (s, 4H); 7.86 (s, 1H); 8.00 (s, 1H); 8.44 (s, 1H); 8.76 (d, J=2.20 Hz, 1H); 9.14 (d, J=2.20 Hz, 1H); 9.20 (s, 1H).

Example H6: 2-(3-ethylsulfonyl-5-vinyl-2-pyridyl)-7-(trifluoromethyl)imidazo[1,2-c]pyrimidine (compound P7, Table P)

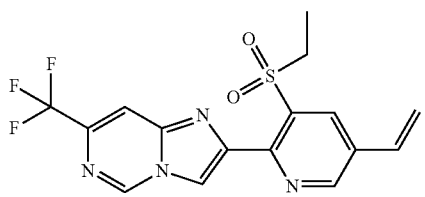

In a microwave vial was placed dibutoxy(vinyl)borane (0.070 g, 0.3676 mmol) and sodium carbonate (0.2757 mL of 2M aqueous solution, 0.5515 mmol), 2-(5-bromo-3-ethylsulfonyl-2-pyridyl)-7-(trifluoromethyl)imidazo[1,2-c]pyrimidine (0.08 g, 0.184 mmol) in acetonitrile (4 mL) were added. The vial was flushed with argon and Chloro(2-dicyclohexylphosphino-2',4',6'-triisopropyl-1,1'-biphenyl)[2-(2'-amino-1,1'-biphenyl)]palladium(II), X-Phos aminobiphenyl palladium chloride precatalyst, XPhos-Pd-G2 (0.01476 g, 0.0184 mmol) was added, the vial capped and stirred in the microwave at 120° C. for 10 min. The reaction mixture was diluted with aqueous NaHCO$_3$ and extracted with dichloromethane (2×). The combined organic layer was dried over Na$_2$SO$_4$, filtered and concentrated in vacuo. The crude product was dissolved in dichloromethane and adsorbed onto teflon bulk sorbents and then purified over a silica gel cartridge (Rf200) eluting with a Cyclohexane/Ethyl acetate gradient to give the title compound as a white solid. Mpt 174-176° C.

LCMS (method 1); 0.88 min (M+H) 383.

$^1$H NMR (400 MHz, chloroform-d) δ ppm 1.37 (t, J=7.34 Hz, 3H); 3.93 (q, J=7.46 Hz, 2H); 5.63 (d, J=11.00 Hz, 1H); 6.07 (d, J=17.61 Hz, 1H); 6.47-6.75 (m, 1H); 7.96 (s, 1H); 8.36 (s, 1H); 8.54 (d, J=2.20 Hz, 1H); 8.88 (d, J=2.20 Hz, 1H); 9.16 (s, 1H).

Example H7: 2-(5-cyclopropyl-3-ethylsulfonyl-2-pyridyl)-7-(trifluoromethyl)imidazo [1,2-c]pyrimidine (Compound P16, Table P)

(Compound P16, Table P)

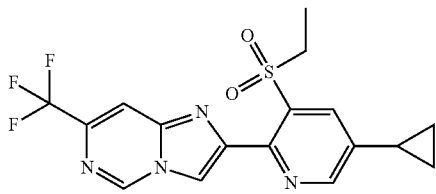

Step A: 1-(5-cyclopropyl-3-ethylsulfonyl-2-pyridyl)ethanone

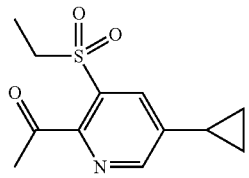 [SMILES: CCS(=O)(=O)c1cc(C2CC2)cnc1C(C)=O]

A sample of 1-(5-bromo-3-ethylsulfonyl-2-pyridyl)ethanone (2 g, 6.85 mmol, prepared as described in step A, example H4) was dissolved in 1,4-dioxane (50 mL) was dissolved in 1,4-dioxane (50 mL). Then cyclopropylboronic acid (1.21 g, 13.7 mmol) and potassium carbonate (2.83 g, 20.53 mmol) were added and the mixture was purged 5 times with vacuum/argon. To this mixture was then added tetrakis(triphenylphosphine)palladium(0) (0.951 g, 0.82150 mmol) and the resulting mixture heated at 90° C. and stirred for 12 hr. After this time, the reaction mixture was treated with water and then extracted with ethyl acetate (three times). The combined organic layers were washed with brine, dried over Na$_2$SO$_4$, filtered and concentrated in vacuo. The crude product was purified by Combiflash chromatography with a column of 40 g and a gradient cyclohexane +0-25% ethyl acetate to give the title compound (1.21 g)) as a colorless oil.

LCMS (method 1); Rt=1.10 min, [M+H] 254

$^1$H NMR (400 MHz, CHLOROFORM-d) δ ppm 0.88-0.94 (m, 2H) 1.20-1.27 (m, 2H) 1.36 (t, J=7.52 Hz, 3H) 2.02-2.12 (m, 1H) 2.73 (s, 3H) 3.62 (q, J=7.34 Hz, 2H) 7.95 (d, J=2.20 Hz, 1H) 8.59 (d, J=2.20 Hz, 1H)

Step B: 2-bromo-1-(5-cyclopropyl-3-ethylsulfonyl-2-pyridyl)ethanone

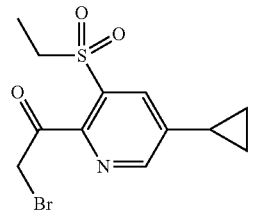 [SMILES: CCS(=O)(=O)c1cc(C2CC2)cnc1C(=O)CBr]

A sample of 1-(5-cyclopropyl-3-ethylsulfonyl-2-pyridyl)ethanone (0.9 g, 3.553 mmol) was dissolved in chloroform (15 mL) and acetonitrile (15 mL) and treated with copper (II)bromide (1.59 g, 7.1 mmol). The resulting mixture was stirred at 140° C. for 55 min in a microwave system. LCMS after this time showed formation of desired product. The reaction mixture was evaporated, residue was dissolved in 100 mL of dichloromethane +5 ml of methanol. The precipitate was filtered over hyflo and filtrate washed with saturated aqueous NaHCO$_3$, dried over Na$_2$SO$_4$, filtered and concentrated in vacuo. The crude was purified by Combi flash chromatography with a column of 40 g and a gradient dichloromethane +0-10% ethylacetate. to give the title compound as a white solid.

LCMS (method 1); Rt=0.93 min, [M+H] 333

$^1$H NMR (400 MHz, CHLOROFORM-d) δ ppm 0.92-0.98 (m, 2H) 1.24-1.31 (m, 2H) 1.38 (t, J=7.52 Hz, 3H) 2.05-2.14 (m, 1H) 3.65 (q, J=7.34 Hz, 2H) 4.79 (s, 2H) 8.01 (d, J=2.20 Hz, 1H) 8.61 (d, J=2.20 Hz, 1H)

Step C: 2-(5-cyclopropyl-3-ethylsulfonyl-2-pyridyl)-7-(trifluoromethyl)imidazo[1,2-c]pyrimidine (Compound P 16, Table P)

(Compound P16, Table P)

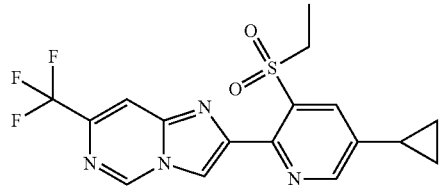

A sample of 6-(trifluoromethyl)pyrimidin-4-amine (73.7 mg, 0.45 mmol, CAS number: [672-41-3]) and 2-bromo-1-(5-cyclopropyl-3-ethylsulfonyl-2-pyridyl)ethanone (150 mg, 0.45 mmol) were dissolved in acetonitrile (3 mL) and the resulting mixture stirred for 1 h at 150° C. in a Microwave System. LCMS showed the formation of product after this time. The reaction mixture concentrated in vacuo, and the residue obtained dissolved in dichloromethane and washed with saturated aqueous NaHCO$_3$. The aqueous layer back-extracted (2 times) with dichloromethane and the combined organic layers washed with NH$_4$OH 1N, brine, dried over Na$_2$SO$_4$ and concentrated in vacuo. The crude product was purified by combi flash chromatography with a column of 12 g and a gradient dichloromethane +0-20% ethyl acetate. The product so obtained was triturated with ethyl acetate, to give the title compound as white solid LCMS (method 1); Rt=0.98 min, [M+H] 397

¹H NMR (400 MHz, CHLOROFORM-d) δ ppm 0.87-0.94 (m, 2H) 1.18-1.24 (m, 2H) 1.34 (t, J=7.34 Hz, 3H) 2.03-2.12 (m, 1H) 3.84 (q, J=7.34 Hz, 2H) 7.95 (s, 1H) 8.10 (d, J=2.20 Hz, 1H) 8.31 (s, 1H) 8.68 (d, J=2.20 Hz, 1H) 9.15 (s, 1H)

Example H8: 2-[5-[2-(3,5-difluorophenyl)ethynyl]-3-ethylsulfonyl-2-pyridyl]-7-(trifluoromethyl)imidazo[1,2-c]pyrimidine: (Compound P29, Table P)

(Compound P29, Table P)

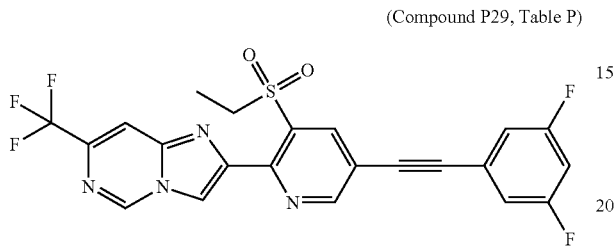

2-(5-chloro-3-ethylsulfonyl-2-pyridyl)-7-(trifluoromethyl)imidazo[1,2-c]pyrimidine (100 mg, 0.26 mmol), 1-ethynyl-3,5-difluoro-benzene (0.126 ml, 1.02 mmol), copper iodide (5 mg, 0.026 mmol), triethylamine (1 mL), dimethylformamide (2 mL), triphenylphosphine (13 mg, 0.051 mmol) and bis (triphenylphosphine) palladium dichloride (36 mg, 0.051 mmol) were mixed together. The vial was gassed with argon and put into microwave for 80 min at 120° C. LCMS analysis showed the formation of desired product. TBME was added. The mixture was extracted three times with water and once with brine. The combined organic layer was dried with Na₂SO₄, filtered and concentrated under vacuum. The crude was purified by flash chromatography over silica gel to give the title compound.

LCMS (method 1); Rt=1.24 min, [M+H] 493.

Example H9: Synthesis of 2-(3-ethylsulfonyl-5-pyrimidin-2-yl-2-pyridyl)-7-(1,1,2,2,2-pentafluoroethyl) imidazo[1,2-c]pyrimidine (Compound P19, Table P)

(Compound P19, Table P)

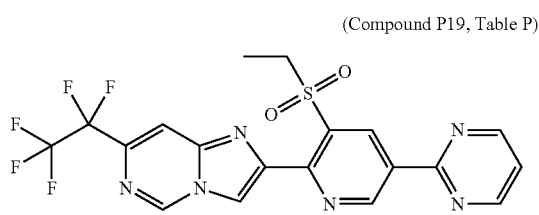 [SMILES: CCS(=O)(=O)c1cc(-c2ncccn2)cnc1-c1cn2cnc(C(F)(F)C(F)(F)F)cc2n1]

Step A: Synthesis of Compound 5 (chenjx20150723-2)

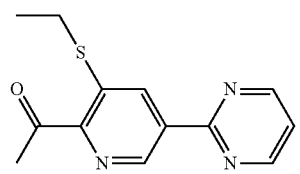 [SMILES: CCSc1cc(-c2ncccn2)cnc1C(C)=O]

A sample of tributyl(pyrimidin-2-yl)stannane (1.1 g, 3 mmol,) was added to a mixture of compound 1-(5-bromo-3-ethylsulfanyl-2-pyridyl)ethanone (520 mg, 3 mmol, prepared as described in step D, Example H3), CuI (76 mg, 0.4 mmol), and PdCl₂(PPh₃)₂ (140 mg, 0.2 mmol) 1,4-dioxane (20 mL) The reaction mixture was refluxed for 2 hours and then concentrated in vacuo. The crude product was purified by column chromatography on silica gel to give the title compound.

¹H-NMR (400 Mz, CDCl₃) δ (ppm): 1.44 (t, 3H), 2.74 (s, 3H), 3.06 (q, 2H), 7.28 (t, 3H), 8.72 (s, 1H), 8.85 (d, 2H), 9.37 (s, 1H). ESI-MS(+): 282 (M+23).

Step B: Synthesis of 1-(3-ethylsulfonyl-5-pyrimidin-2-yl-2-pyridyl)ethanone

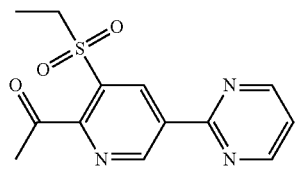

1-(3-ethylsulfanyl-5-pyrimidin-2-yl-2-pyridyl)ethanone (1.16 mmol, 301 mg) and m-CPBA (998 mg, 5.8 mmol) in 20 ml of DCM was stirred at ambient temperature for 3 h. Then the mixture was poured into a saturated solution of NaHCO₃ and Na₂SO₃ in water, and extracted with ethyl acetate three times. The combined organic layers were dried over sodium sulfate, filtered and concentrated under vacuum. The crude product was purified by column chromatography on silica gel to give 1-(3-ethylsulfonyl-5-pyrimidin-2-yl-2-pyridyl)ethanone.

¹H-NMR (400 Mz, CDCl₃) δ (ppm): 1.38 (t, 3H), 2.74 (s, 3H), 3.58 (q, 2H), 7.33 (t, 3H), 8.87 (s, 1H), 8.33 (d, 2H), 9.78 (s, 1H). ESI-MS(+): 314 (M+23).

Step C: Synthesis of 2-bromo-1-(3-ethylsulfonyl-5-pyrimidin-2-yl-2-pyridyl)ethanone

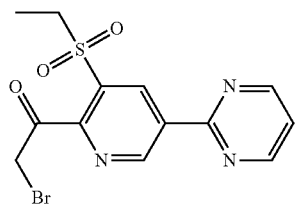 [SMILES: CCS(=O)(=O)c1cc(-c2ncccn2)cnc1C(=O)CBr]

1-(3-ethylsulfonyl-5-pyrimidin-2-yl-2-pyridyl)ethanone (1 mmol, 291 mg) and CuBr₂ (12 mmol, 447 mg) in 2 ml of ethyl acetate and 2 ml of CHCl₃ were stirred at microwave 140° C. for 1.5 h. Then the mixture was concentrated under vacuum. The crude product was used for next step.

Step D: Synthesis of 6-bromopyrimidin-4-amine

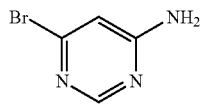

To a solution of 4,6-dibromopyrimidine (12 g, 50.6 mmol, CAS: 36847-10-6) in 300 mL of CH₃CN was added NH₃.H₂O (240 mL). The mixture was stirred at ambient temperature for 16 hours. Then, the mixture was poured into water and extracted with ethyl acetate four times. The combined organic layers were dried over sodium sulfate, filtered and concentrated under vacuum. The crude product was recrystallization with PE/EA to give 6-bromopyrimidin-4-amine ¹H NMR (400 Mz, DMSO-d₆) δ (ppm): 6.58 (s, 1H), 7.17 (s, 2H), 8.10 (s, 1H).

Step E: Synthesis of 6-iodopyrimidin-4-amine

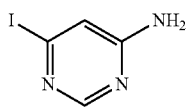

To a solution of 6-bromopyrimidin-4-amine (4.17 g, 24 mmol) in 100 mL of HI was added NaI (14.4 g, 96 mmol). The mixture was stirred at ambient temperature for 2 days. Then, the mixture was adjusted to pH=10 with NaOH solution, and the solid was separated and filtered to give 6-iodopyrimidin-4-amine. ¹H NMR (400 Mz, DMSO-d₆) δ (ppm): 6.85 (s, 1H), 6.99 (s, 2H), 7.99 (s, 1H).

Step F: Synthesis of 6-(1,1,2,2,2-pentafluoroethyl)pyrimidin-4-amine

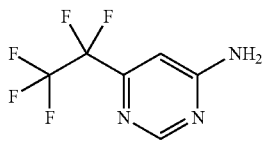 [SMILES: Nc1cc(C(F)(F)C(F)(F)F)ncn1]

To a solution of 6-iodopyrimidin-4-amine (442 mg, 2 mmol) in 5 mL of DMF was added (Phen)CuCF₂CF₃ (1.14 g, 3 mmol, purchased from Aspira scientific). The mixture was stirred at 90° C. for 2 hours. Then, the mixture was poured into water and extracted with ethyl acetate. The combined organic layers were dried over sodium sulfate, filtered and concentrated under vacuum. The crude product was purified by column chromatography on silica gel to give 6-(1,1,2,2,2-pentafluoroethyl)pyrimidin-4-amine.

¹H NMR (400 Mz, DMSO-d₆) δ (ppm): 6.80 (s, 1H), 7.50 (s, 2H), 8.47 (s, 1H). ¹⁹F-NMR (300 Mz, DMSO-d₆) δ: −79.41 (s, 3F), −116.10 (s, 2F); ESI-MS(+): 214 (M+1), ESI-MS(−): 212 (M−1).

Step G: Synthesis of 2-(3-ethylsulfonyl-5-pyrimidin-2-yl-2-pyridyl)-7-(1,1,2,2,2-pentafluoroethyl)imidazo[1,2-c]pyrimidine (Compound P19, Table P)

(Compound P19, Table P)

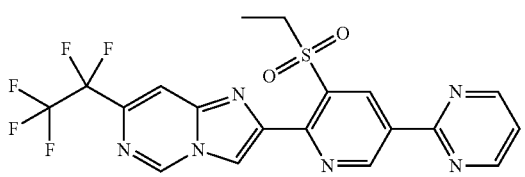

2-bromo-1-(3-ethylsulfonyl-5-pyrimidin-2-yl-2-pyridyl)ethanone (0.27 mmol, 100 mg) and 6-(1,1,2,2,2-pentafluoroethyl)pyrimidin-4-amine (0.47 mmol, 100 mg) in 4 ml of CH₃CN were stirred at microwave 140° C. for 2 h. Then the mixture was concentrated under vacuum. The crude product was purified by column chromatography on silica gel to give 2-(3-ethylsulfonyl-5-pyrimidin-2-yl-2-pyridyl)-7-(1,1,2,2,2-pentafluoroethyl)imidazo[1,2-c]pyrimidine ¹H NMR (400 Mz, CDCl₃) δ (ppm): 1.42 (t, 3H), 4.02 (q, 2H), 7.34 (t, 1H), 8.00 (s, 1H), 8.44 (s, 1H), 8.89 (d, 2H), 9.17 (s, 1H), 9.88 (s, 1H); ¹⁹F-NMR (300 Mz, CDCl₃) δ: −81.21 (s, 3F), −116.03 (s, 2F); ESI-MS(+): 485 (M+1).

Example H10: Synthesis of 2-[3-ethylsulfonyl-5-[4-(trifluoromethyl)phenyl]-2-pyridyl]-7-(1,1,2,2,2-pentafluoroethyl)imidazo[1,2-c]pyrimidine (Compound P 20, Table P)

(Compound P20, Table P)

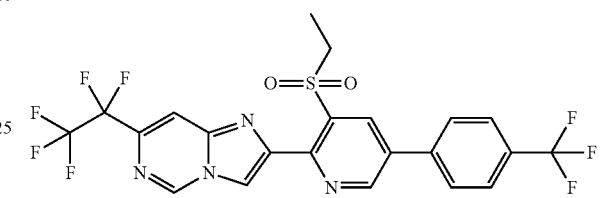

Step A: Synthesis of 1-(5-bromo-3-ethylsulfonyl-2-pyridyl)ethanone

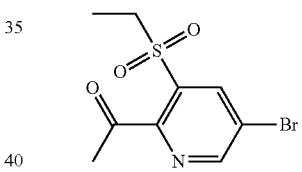

A sample of 1-(5-bromo-3-ethylsulfanyl-2-pyridyl)ethanone (4 mmol, 1.04 g, prepared as described in Step D, Example H3) and meta-chloroperoxybenzoic acid (2.06 g, 12 mmol) in 20 ml of dichloromethane was stirred at ambient temperature for 4 hours. The mixture was poured into a saturated solution of NaHCO₃ and Na₂SO₃ in water, and extracted with ethyl acetate (three times).

The combined organic layers were dried over sodium sulfate, filtered and concentrated in vacuo. The crude product was purified by column chromatography on silica gel to give 1-(5-bromo-3-ethylsulfonyl-2-pyridyl) ethanone.

¹H NMR (400 Mz, CDCl₃) δ (ppm): 1.34 (t, 3H), 2.66 (s, 3H), 3.58 (q, 2H), 8.47 (s, 1H), 8.83 (s, 1H).

Step B: Synthesis of 1-[3-ethylsulfonyl-5-[4-(trifluoromethyl)phenyl]-2-pyridyl]ethanone

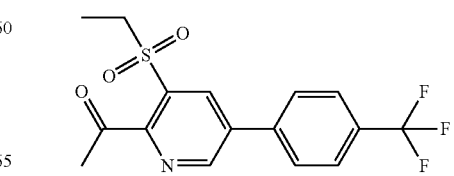

1-(5-bromo-3-ethylsulfonyl-2-pyridyl)ethanone (507 mg, 2.67 mmol) was added to a mixture of [4-(trifluoromethyl)phenyl]boronic acid (520 mg, 1.78 mmol), Pd(PPh$_3$)$_4$ (206 mg, 0.178 mmol), K$_2$CO$_3$ (738 mg, 5.34 mmol) in 20 ml of 1,4-dioxane under N$_2$. The mixture was refluxed overnight and then concentrated in vacuo. The crude product was purified by column chromatography on silica gel to give the title compound.

$^1$H-NMR (400 Mz, CDCl$_3$) δ (ppm): 1.37 (t, 3H), 2.73 (s, 3H), 3.62 (q, 2H), 7.78 (t, 4H), 8.53 (s, 1H), 9.00 (s, 1H). $^{19}$F-NMR (300 Mz, CDCl$_3$) δ: −61.04 (s, 3F); ESI-MS(+): 380 (M+23).

Step C: Synthesis of 2-bromo-1-[3-ethylsulfonyl-5-[4-(trifluoromethyl)phenyl]-2-pyridyl] ethanone

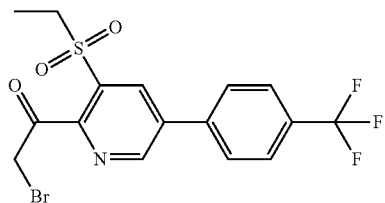 [SMILES: CCS(=O)(=O)c1cc(-c2ccc(C(F)(F)F)cc2)cnc1C(=O)CBr]

A sample of 1-[3-ethylsulfonyl-5-[4-(trifluoromethyl)phenyl]-2-pyridyl]ethanone (1 mmol, 357 mg) and CuBr$_2$ (12 mmol, 447 mg) in 2 ml of ethyl acetate and 2 ml of CHCl$_3$ were stirred at sealed tube 140° C. for 20 h. The mixture was concentrated in vacuo and the crude product was used as such for next step.

Step D: Synthesis of 2-[3-ethylsulfonyl-5-[4-(trifluoromethyl)phenyl]-2-pyridyl]-7-(1,1,2,2,2-pentafluoroethyl)imidazo[1,2-c]pyrimidine (Compound P20, Table P)

(Compound P20, Table P)

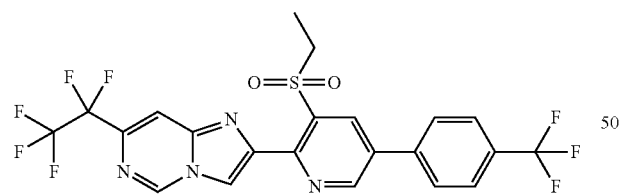

A sample of 2-bromo-1-[3-ethylsulfonyl-5-[4-(trifluoromethyl)phenyl]-2-pyridyl]ethanone (0.27 mmol, 118 mg) and 6-(1,1,2,2,2-pentafluoroethyl)pyrimidin-4-amine (0.5 mmol, 107 mg, prepared as described in step F, Example H9) in 4 ml of CH$_3$CN were stirred at microwave 140° C. for 2 h. Then the mixture was concentrated in vacuo. and the crude product purified by column chromatography on silica gel to give the title compound.

$^1$H NMR (400 Mz, CDCl$_3$) δ 1.41 (t, 3H), 4.02 (q, 2H), 7.81 (s, 4H), 8.01 (s, 1H), 8.43 (s, 1H), 8.74 (s, 1H), 9.12 (s, 1H), 9.18 (s, 1H); $^{19}$F-NMR (300 Mz, CDCl$_3$) δ: −61.13 (s, 3F), −81.18 (s, 3F), −116.04 (s, 2F); ESI-MS(+): 551 (M+1).

Example H11: Synthesis of 2-[5-(5,6-dichloro-2-pyridyl)-3-ethylsulfonyl-2-pyridyl]-7-(trifluoromethylsulfanyl)imidazo[1,2-c]pyrimidine (Compound P26, Table P)

(Compound P26, Table P)

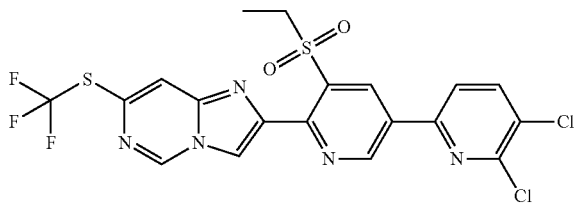

Step A: Synthesis of 6-bromo-2-chloro-pyridin-3-amine

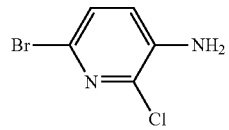

A sample of 2-chloropyridin-3-amine (10 mmol, 1.28 g CAS: [169833-70-9]) and N-brom-succinamide (20 mmol, 3.56 g) in 40 ml of DMF were stirred at ambient temperature for 4 h. After this time, the mixture was poured into water and extracted with ethyl acetate (three times) The combined organic layers were dried over sodium sulfate, filtered and concentrated in vacuo. The crude product was purified by column chromatography on silica gel to give the title compound.

$^1$H-NMR (400 Mz, DMSO-d$_6$) δ: 5.71 (s, 2H), 7.10 (d, 1H), 7.31 (d, 1H).

Step B: Synthesis of 6-bromo-2,3-dichloro-pyridine

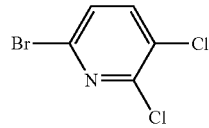

Isoarmyl nitrite (2.64 g, 22.56 mmol) was added to a mixture of 6-bromo-2,3-dichloro-pyridine (1.55 g, 7.52 mmol), and CuCl$_2$ (2.03 g, 15.04 mmol) in 30 ml of CH$_3$CN, and the mixture stirred at ambient temperature for 4 h. After this time, the solvent was removed in vacuo and the crude product was purified by column chromatography on silica gel to give the title compound.

$^1$H-NMR (400 Mz, DMSO-d$_6$) δ: 7.71 (d, 1H), 8.05 (d, 1H).

Step C: Synthesis of tributyl-(5,6-dichloro-2-pyridyl)stannane

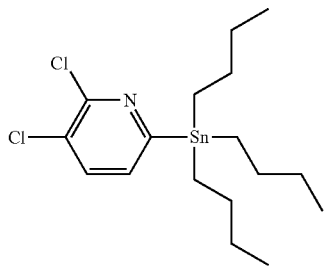 [SMILES: CCC[CH2][Sn]([CH2]CCC)([CH2]CCC)[c]1ccc(Cl)c(Cl)n1]

To a solution of 6-bromo-2,3-dichloro-pyridine (1.125 g, 5 mmol) in 40 mL of dry toluene at −60° C. was added n-butyllithium (2.4 mL of a 2.5 M solution in hexane, 6 mmol) under an nitrogen atmosphere. After stirring for 30 min, Bu$_3$SnCl (1.8 g, 5.5 mmol) was added slowly during a 10 min period, and the mixture was stirred at −60° C. for 1 h. The cooling bath was removed and the solution was allowed to warm to ambient temperature over 1 hour. The reaction mixture was poured into water and extracted with ether (3×100 mL) and the combined organic layers washed with water, dried over MgSO$_4$, and concentrated in vacuo. The crude product was purified by column chromatography on silica gel to give the title compound.

$^1$H NMR (400 Mz, CDCl$_3$) δ (ppm): 0.87 (t, 9H), 1.15 (m, 6H), 1.32 (m, 6H), 1.55 (m, 6H), 7.28 (d, 1H), 7.55 (d, 1H).

Step D: Synthesis of 6-(trifluoromethylsulfanyl)pyrimidin-4-amine

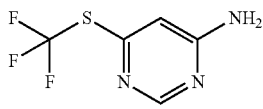 [SMILES: Nc1cc(SC(F)(F)F)ncn1]

To a solution of 6-bromopyrimidin-4-amine (1.75 g, 10 mmol) in 45 mL of dry CH$_3$CN was added (bpy)CuSCF$_3$ (4.8 g, 15 mmol, purchased from Aspira Scientific). The mixture was refluxed at 100° C. for 2 h under an nitrogen atmosphere. Then, the mixture was filtered and concentrated in vacuo The crude product was purified by column chromatography on silica gel to give the title compound, 6-(trifluoromethylsulfanyl)pyrimidin-4-amine.

$^1$H-NMR (400 Mz, DMSO-d$_6$) δ: 6.60 (s, 1H), 7.26 (s, 2H), 8.29 (s, 1H). $^{19}$F-NMR (300 Mz, DMSO-d$_6$) δ: −42.45 (s, 3F).

Step E: Synthesis of 2-(5-bromo-3-ethylsulfonyl-2-pyridyl)-7-(trifluoromethylsulfanyl)imidazo[1,2-c]pyrimidine

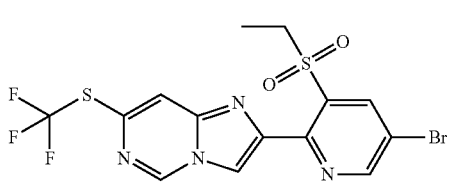 [SMILES: CCS(=O)(=O)c1cc(Br)cnc1-c1cn2cnc(SC(F)(F)F)cc2n1]

2-bromo-1-(5-bromo-3-ethylsulfonyl-2-pyridyl)ethanone (370 mg, 1 mmol) and 6-(trifluoromethylsulfanyl)pyrimidin-4-amine (234 mg, 1.2 mmol) in 5 ml of CH$_3$CN were stirred at microwave 135° C. for 2 hours. Then the mixture was concentrated under vacuum. The crude product was purified by column chromatography on silica gel to give the title compound.

$^1$H NMR (400 Mz, CDCl$_3$) δ 1.35 (t, 3H), 3.91 (q, 2H), 7.89 (s, 1H), 8.28 (s, 1H), 8.65 (s, 1H), 8.92 (s, 1H), 9.06 (s, 1H); $^{19}$F-NMR (300 Mz, CDCl$_3$) δ: −38.47 (s, 3F); ESI-MS(+): 491 (M+Na).

Step F: Synthesis of compound 2-[5-(5,6-dichloro-2-pyridyl)-3-ethylsulfonyl-2-pyridyl]-7-(trifluoromethylsulfanyl)imidazo[1,2-c]pyrimidine (Compound P26, Table P)

(Compound P26, Table P)

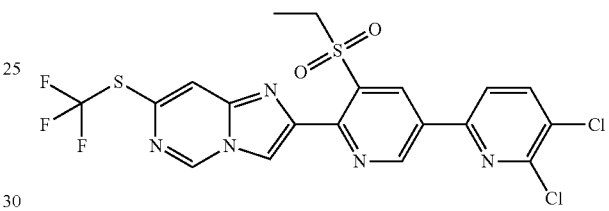

A sample of tributyl-(5,6-dichloro-2-pyridyl)stannane (262 mg, 0.6 mmol) was added to a mixture of 2-(5-bromo-3-ethylsulfonyl-2-pyridyl)-7-(trifluoromethylsulfanyl)imidazo[1,2-c]pyrimidine (140 mg, 0.3 mmol), CuI (57 mg, 0.3 mmol), and PdCl$_2$(PPh$_3$)$_2$ (42 mg, 0.06 mmol) in 30 ml of 1,4-dioxane, and the mixture refluxed at 120° C. for 8 hours. After concentration. in vacuo, purification by column chromatography on silica gives the title compound.

$^1$H NMR (400 Mz, DMSO-d$_6$) δ: 1.30 (t, 3H), 4.19 (q, 2H), 8.27 (s, 1H), 8.36 (d, 2H), 8.69 (s, 1H), 9.01 (s, 1H), 9.60 (d, 2H); $^{19}$F-NMR (300 Mz, DMSO-d$_6$) δ: −37.41 (s, 3F); ESI-MS(−): 570 (M+Cl); LC-MS: 534 (M+1).

Example H12: Synthesis of 2-[3-ethylsulfonyl-5-[4-(trifluoromethyl)-2-pyridyl]-2-pyridyl]-7-(trifluoromethylsulfanyl)imidazo[1,2-c]pyrimidine (Compound P27, Table P)

(Compound P27, Table P)

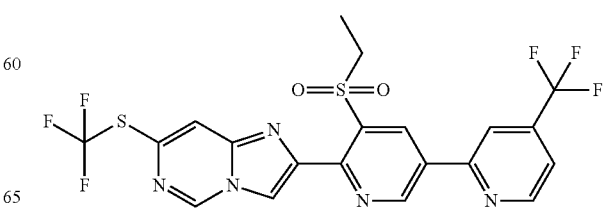

Step A: Synthesis of tributyl-[4-(trifluoromethyl)-2-pyridyl]stannane

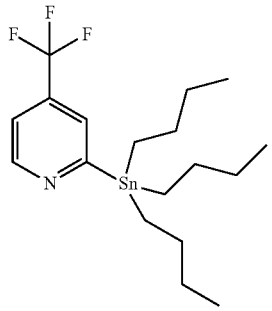 [SMILES: CCC[CH2][Sn]([CH2]CCC)([CH2]CCC)[c]1cc(C(F)(F)F)ccn1]

A mixture of 2-bromo-4-(trifluoromethyl)pyridine (1.827 g, 8 mmol) in toluene (20 ml) cooled to −70° C. was added n-butyllithium (0.9 ml, 9.6 mmol) dropwise under nitrogen protection. After 30 minutes, Tri-n-butyltin chloride (2.58 ml, 8.8 mmol) was added to the mixture slowly. Then the mixture was stirred at ambient temperature. After 1 h, the solution was washed and extracted with ethyl acetate. The residue was purified by column chromatography on silica gel (petroleum ether/ethyl acetate=20:1) to give tributyl-[4-(trifluoromethyl)-2-pyridyl]stannane.

$^1$H NMR (400 Mz, CDCl$_3$) δ 8.90 (d, 1H, J=12 Hz), 7.56 (m, 1H), 7.28 (m, 1H), 1.54 (m, 6H), 1.30 (m, 6H), 1.14 (m, 6H), 0.86 (m, 9H).

Synthesis of 1-[3-ethylsulfonyl-5-[4-(trifluoromethyl)-2-pyridyl]-2-pyridyl]ethanone

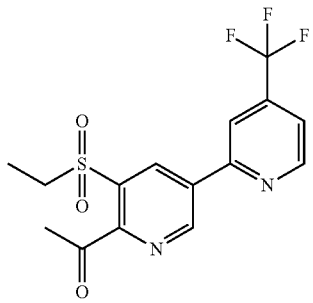 [SMILES: CCS(=O)(=O)c1cc(-c2cc(C(F)(F)F)ccn2)cnc1C(C)=O]

A mixture of tributyl-[4-(trifluoromethyl)-2-pyridyl]stannane (1.5 g, 3.4 mmol), 1-(5-bromo-3-ethylsulfonyl-2-pyridyl)ethanone (1 g, 3.4 mmol), cuprous iodide (131 mg, 0.68 mmol) and bis(triphenylphosphine) palladium(II) dichloride (241 mg, 0.34 mmol) in 1,4-dioxane (15 ml) was heated to reflux overnight under nitrogen protection. After the mixture was cooled to ambient temperature, the solvent was evaporated in vacuo. The residue was purified by column chromatography on silica gel (petroleum ether/ethyl acetate=4:1) to give 1-[3-ethylsulfonyl-5-[4-(trifluoromethyl)-2-pyridyl]-2-pyridyl]ethanone.

$^1$H NMR (300 Mz, CDCl$_3$) δ(ppm): 9.47 (s, 1H), 8.98 (s, 2H), 8.045 (s, 1H), 7.926 (s, 1H), 3.636 (m, 2H), 2.772 (s, 3H), 1.394 (m, 3H). $^{19}$F (300 Mz, CDCl$_3$) δ(ppm): −63.04 (s, 3H); ESI-MS(Na$^+$): 381.

Step B: Synthesis of 1-bromo-3-[(Z)-2-[4-(trifluoromethyl)-2-pyridyl]prop-2-enylideneamino]propan-2-one

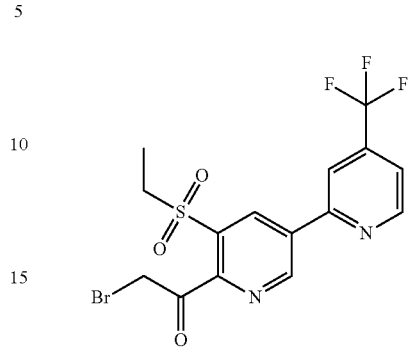

A mixture of 1-[3-ethylsulfonyl-5-[4-(trifluoromethyl)-2-pyridyl]-2-pyridyl]ethanone (358 mg, 1 mol) and CuBr$_2$ (446 mg, 2 mmol) in acetonitrile and trichloromethane was heated at 130° C. in a sealed tube for 8 h. After the reaction mixture was cooled to ambient temperature, the solvent was evaporated in vacuo. The residue was purified by column chromatography on silica gel (petroleum ether/ethyl acetate=4:1) to give the crude 1-bromo-3-[(Z)-2-[4-(trifluoromethyl)-2-pyridyl]prop-2-enylideneamino]propan-2-one that was used in the next step without further purification.

Step C: Synthesis of compound 2-[3-ethylsulfonyl-5-[4-(trifluoromethyl)-2-pyridyl]-2-pyridyl]-7-(trifluoromethylsulfanyl)imidazo[1,2-c]pyrimidine (Compound P27, Table P)

(Compound P27, Table P)

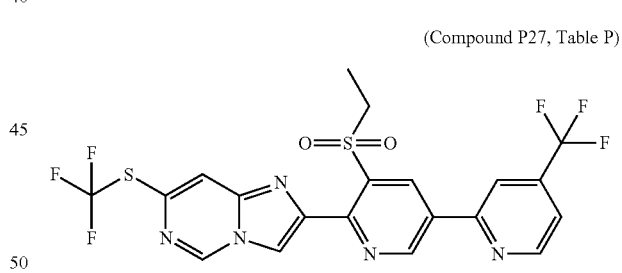

A mixture of compound 5 (184 mg, 0.42 mol) and 6-(trifluoromethylsulfanyl)pyrimidin-4-amine (82.1 mg, 0.42 mmol) in acetonitrile was heated at 140° C. in microwave reactor for 2 h. After the reaction mixture was cooled to ambient temperature, the solvent was evaporated in vacuo. The residue was purified by column chromatography on silica gel (petroleum ether/ethyl acetate=1:3) to give 2-[3-ethylsulfonyl-5-[4-(trifluoromethyl)-2-pyridyl]-2-pyridyl]-7-(trifluoromethylsulfanyl)imidazo[1,2-c]pyrimidine.

$^1$H NMR (400 Mz, CDCl$_3$) δ(ppm): 9.578 (br, 1H), 9.1 (br, 2H), 8.973 (d, J=4.4 Hz, 1H), 8.398 (br, 1H), 8.062 (s, 1H), 7.92 (br, 1H), 7.589 (d, J=5.2 Hz, 1H), 3.975 (m, 2H), 1.628 (br, 3H). $^{19}$F (400 Mz, CDCl$_3$) δ (ppm): −39.4 (s, 3H), −63.7 (s, 3H). ESI-MS(H$^+$): 534.

Example H13: 1-[5-ethylsulfonyl-6-[7-(trifluoromethyl)imidazo[1,2-c]pyrimidin-2-yl]-3-pyridyl]cyclopropanecarbonitrile (Compound P 8, Table P)

(Compound P8, Table P)

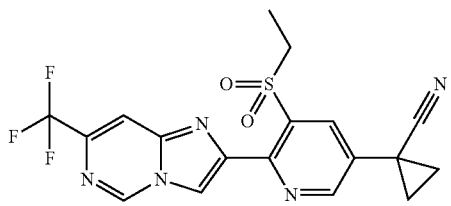

Step A: Synthesis of 1-(5-chloro-3-ethylsulfanyl-2-pyridyl)ethanone

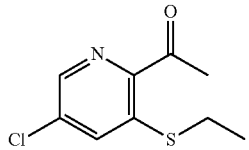

1-(5-chloro-3-fluoro-2-pyridyl)ethanone (50 g, 288.07 mmol) and potassium carbonate (79.628 g, 576.14 mmol) was mixed in N,N-dimethylformamide (576.14 mL) and cooled down at −10° C. Ethanethiol (22 mL, 288.07 mmol) was added and reaction mixture was stirred at ambient temperature for 16 hours. Water was added and aqueous layer was extracted with ethylacetate. The combined organic layers was washed with water, dried over anhydrous magnesium sulfate and then concentrated under reduced pressure. The crude was purified by flash chromatography over silica gel to give 1-(5-chloro-3-ethylsulfanyl-2-pyridyl)ethanone.

LCMS (Method 1): 216 (M+H)+; retention time: 1.01 min.

1H NMR (400 MHz, CHLOROFORM-d) ä ppm 1.41 (t, J=7.52 Hz, 4H) 2.68 (s, 3H) 2.90 (q, J=7.34 Hz, 2H) 7.61 (d, J=1.83 Hz, 1H) 8.31 (d, J=2.20 Hz, 1H)

Step B: Synthesis of 1-(5-chloro-3-ethylsulfonyl-2-pyridyl)ethanone

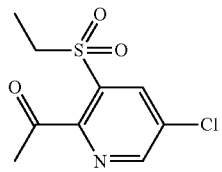

In a three neck flask under argon, 1-(5-chloro-3-ethylsulfanyl-2-pyridyl)ethanone (24 g, 111.27 mmol) was dissolved in dichloromethane (480 mL) and cooled down at 0° C. Then 3-chloroperoxybenzoic acid (57.602 g, 233.66 mmol) was added and reaction was stirred 30' at 0° C. then warmed up at ambient temperature and stirred one night. LCMS showed reaction completion. Reaction mixture was quenched with NaOH 1 M and sodium thiosulfate sol. The aqueous layer was extracted 3 times with dichloromethane. The combined organic layers was washed with NaOH 1M (5 times), brine, dried over Na$_2$SO$_4$, filtered and evaporated under vacuum to give 1-(5-chloro-3-ethylsulfonyl-2-pyridyl)ethanone.

LCMS (Method 1): 248 (M+H)+; retention time: 0.84 min. 1H NMR (400 MHz, CHLOROFORM-d) ä ppm 1.36 (t, J=7.34 Hz, 3H) 2.70 (s, 3H) 3.60 (q, J=7.70 Hz, 2H) 3.56-3.65 (m, 2H) 8.36 (d, J=2.20 Hz, 1H) 8.75 (d, J=2.20 Hz, 1H)

Step C: Synthesis of 2-bromo-1-(5-chloro-3-ethylsulfonyl-2-pyridyl)ethanone

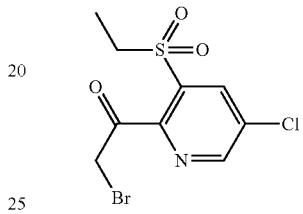

In microwave vial, 1-(5-chloro-3-ethylsulfonyl-2-pyridyl)ethanone (6 g, 24.223 mmol), dibromocopper (10.820 g, 48.446 mmol), acetonitrile (21 mL) and chloroform (21 mL) were mixed together and reaction mixture was stirred 55' at 140° C. under microwave system. LCMS showed the formation of product. The reaction mixture was evaporated under vacuum. The rest was dissolved in dichloromethane (200 mL) and methanol (5 mL9 and filtered. The mother liquid was washed with NaHCO$_3$. and NH4OH 1 N. The aqueous layer was extracted with ethylacetate (100 mL). The combined organic layers was dried over Na$_2$SO$_4$, filtered and evaporated under vacuum. The crude was purified by flash chromatography over silica gel to give 2-bromo-1-(5-chloro-3-ethylsulfonyl-2-pyridyl)ethanone.

LCMS (Method 1): 327 (M+H)+; retention time: 0.89 min.

1H NMR (400 MHz, CHLOROFORM-d) ä ppm 1.40 (t, J=7.52 Hz, 3H) 3.66 (q, J=7.58 Hz, 2H) 4.75 (s, 2H) 8.45 (d, J=2.20 Hz, 1H) 8.81 (d, J=2.20 Hz, 1H)

Step D: Synthesis of 2-(5-chloro-3-ethylsulfonyl-2-pyridyl)-7-(trifluoromethyl)imidazo[1,2-c] pyrimidine

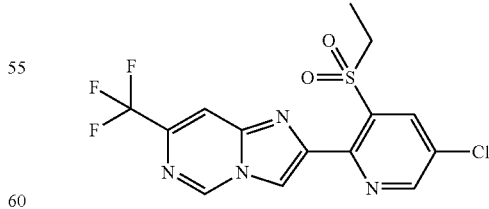

In a microwave vial 2-bromo-1-(5-chloro-3-ethylsulfonyl-2-pyridyl)ethanone (1.05 g, 3.21 mmol) and 4-(trifluoromethyl)-1,6-dihydropyrimidin-6-amine (0.541 g, 3.21 mmol) were dissolved in acetonitrile (10.5 mL). The vials were stirred 1 hour at 150° C. in a microwave system. LCMS analysis showed mass of the product. The reaction mixture was evaporated under vacuum. The residue was dissolved in dichloromethane and washed with NaHCO$_3$ sat sol and NH$_4$OH 1N. The combined organic layers was washed with brine, dried over Na$_2$SO$_4$, filtered and concentrated in vacuo. The crude product was purified by flash chromatography over silica gel to give the title compound.

LCMS (Method 1): 391 (M+H)+; retention time: 0.95 min.

1H NMR (400 MHz, CHLOROFORM-d) δ ppm 1.39 (t, J=7.34 Hz, 3H) 3.99 (q, J=7.34 Hz, 2H) 7.96 (s, 1H) 8.35 (s, 1H) 8.54 (d, J=2.20 Hz, 1H) 8.84 (d, J=2.57 Hz, 1H) 9.17 (s, 1H)

Step D: Synthesis of 2-[5-ethylsulfonyl-6-[7-(trifluoromethyl)imidazo[1,2-c]pyrimidin-2-yl]-3-pyridyl]acetonitrile (Compound P30, Table P)

(Compound P30, Table P)

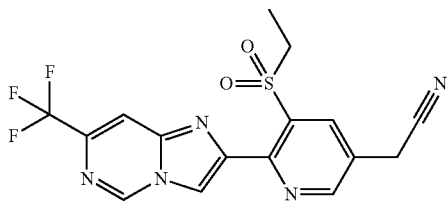

In a microwave vial, under argon, 2-(5-chloro-3-ethylsulfonyl-2-pyridyl)-7-(trifluoromethyl)imidazo[1,2-c]pyrimidine (0.3 g, 0.7677 mmol) was diluted in dimethylformamide (1.5 mL). TMSAN (0.321 mL, 2.303 mmol), difluorozinc (0.04761 g, 0.4606 mmol), XANTPHOS (0.0181 g, 0.03071 mmol) and PD2(DBA)3 (0.01406 g, 0.01535 mmol) were added and the vial was capped and heated at 140° C. for 45 min in the microwave system. LCMS analysis showed the formation of product. Reaction mixture was diluted with ethylacetate and filtered over hyflo. The mother liquid was extracted with a mixture of water and ammonium chloride then with brine, dried over Na$_2$SO$_4$, filtered and evaporated under vacuum. The crude was purified by flash chromatography on silicagel to give 2-[5-ethylsulfonyl-6-[7-(trifluoromethyl)imidazo[1,2-c]pyrimidin-2-yl]-3-pyridyl]acetonitrile.

LCMS (Method 1): 396 (M+H)+; retention time: 0.82 min.

1-[5-ethylsulfonyl-6-[7-(trifluoromethyl)imidazo[1,2-c]pyrimidin-2-yl]-3-pyridyl]cyclopropanecarbonitrile (Compound P8, Table P)

(Compound P8, Table P)

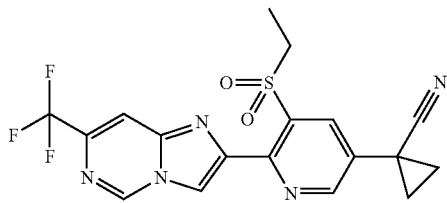

A sample of 2-[5-ethylsulfonyl-6-[7-(trifluoromethyl)imidazo[1,2-c]pyrimidin-2-yl]-3-pyridyl]acetonitrile (0.075 g, 0.1897 mmol) was dissolved in acetonitrile (2.25 mL). Dicesium carbonic acid (0.1234 g, 0.3794 mmol) and 1,2-dibromoethane (0.0334 mL, 0.3794 mmol) were added at ambient temperature. The resulting mixture was stirred at 80° C. 1 hour. LCMS analysis showed the formation of product. Reaction mixture was evaporated. Residue was diluted in ethylacetate and water. The aqueous layer was extracted 3 times with ethylacetate. The combined organic layer was washed once with water and brine, dried over Na$_2$SO$_4$, filtered and evaporated. The crude was purified by flash chromatography on silica gel to give 1-[5-ethylsulfonyl-6-[7-(trifluoromethyl)imidazo[1,2-c]pyrimidin-2-yl]-3-pyridyl]cyclopropanecarbonitrile.

LCMS (Method 1): 422 (M+H)+; retention time: 0.89 min

Example I2: Preparation of Methyl 5-(1-cyanocyclopropyl)-3-ethylsulfonyl-pyridine-2-carboxylate; (Compound I8, Table I)

(Compound I8, Table I)

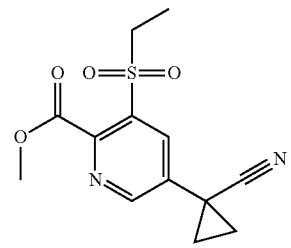

Step 1: Preparation of Methyl 5-bromo-3-ethylsulfonyl-pyridine-2-carboxylate

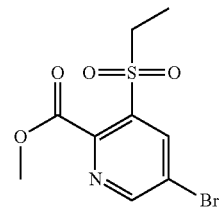 [SMILES: CCS(=O)(=O)c1cc(Br)cnc1C(=O)OC]

Methyl 5-bromo-3-ethylsulfanyl-pyridine-2-carboxylate (24.4 g, 88.4 mmol, step B1 from example P1)) was suspended in dichloromethane (250 mL), cooled to 0° C., and treated portion wise with mCPBA (37.6 g, 185.7 mmol). The mixture was stirred at ambient temperature for 18 hours. The mixture was diluted with water and dichloromethane, the aqueous phase was back extracted with dichloromethane (two times), and the combined organic phases washed with Na$_2$S$_2$O$_4$, and dried over Na$_2$SO$_4$. Partial concentration of the solvent, led to a solid (the desired title compound) that was filtered. The filtrate was evaporated to dryness, which was purified by chromatography on silica to give further pure title compound as white solid.

LCMS (method 1): 308/310 (M+H)$^+$; retention time: 0.76 min.

(d$^6$-DMSO, 400 MHz): 9.08 (d, J=2.4 Hz, 1H), 8.58 (d, J=2.4 Hz, 1H), 3.87 (s, 3H), 3.52 (q, J=7.8 Hz, 2H), 1.18 (t, J=7.8 Hz, 3H).

Step 2: Preparation of Methyl 5-(cyanomethyl)-3-ethylsulfonyl-pyridine-2-carboxylate

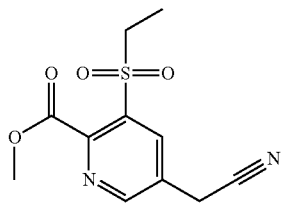 [SMILES: CCS(=O)(=O)c1cc(CC#N)cnc1C(=O)OC]

A solution of methyl-5-bromo-3-ethylsulfonyl-pyridine-2-carboxylate, (2.00 g, 6.49 mmol) in DMF (13.0 mL) was treated with TMS-acetonitrile (2.25 g, 2.71 mL, 19.5 mmol), difluorozinc (0.403 g, 3.89 mmol), XANTPHOS (0.153 g, 0.260 mmol) and $Pd_2(dba)_3$ (0.119 g, 0.130 mmol) under argon. The resulting mixture was stirred for 5 hours at 100° C. LCMS after this time showed no further reaction progression. The mixture was cooled, diluted with EtOAc, and filtered over hyflo. The filtrate was washed with water/NH4Cl, brine, dried over $Na_2SO_4$, filtered and concentrated in vacuo. The crude product was purified by combi flash chromatography with a column of 40 g and a gradient cyclohexane +0-50% ethyl acetate. This gave the title compound as yellow oil.

LCMS (method 1): 269 (M+H)$^+$; retention time: 0.58 min.
$^1$H NMR (400 MHz, CHLOROFORM-d) δ ppm: 1.38 (t, J=7.5 Hz, 3H), 3.58 (q, J=7.5 Hz, 2H), 3.95 (s, 2H), 4.06 (s, 3H), 8.37 (d, J=2.20 Hz, 1H), 8.86 (d, J=2.20 Hz, 1H).

Step 3: Preparation of Methyl 5-(1-cyanocyclopropyl)-3-ethylsulfonyl-pyridine-2-carboxylate (Compound I-8, Table I)

(Compound I-8, Table I)

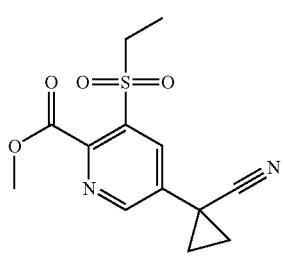

Methyl 5-(cyanomethyl)-3-ethylsulfonyl-pyridine-2-carboxylate (0.63 g, 2.3 mmol) was dissolved in acetonitrile (19 mL) and cesium carbonate (2.3 g, 7.0 mmol) was added to the colourless solution (solution darkened), followed by addition of 1,2-dibromoethane (0.90 g, 0.41 mL, 4.7 mmol) The brown solution was stirred at 80° C. bath temperature. LC/MS detected desired mass at 0.73 after 1.5 h. The reaction mixture was concentrated in vacuo and diluted with EtOAc and water. The organic layer was separated, washed successively with water and brine, dried over $Na_2SO_4$, filtered and concentrated in vacuo. The crude product was dissolved in dichloromethane and adsorbed onto TEFLON BULK SORBENTS. Purification over a silica gel cartridge (Rf200) eluting with Cyclohexane/EtOAc, gave the title compound as a beige resin.

LCMS (method 1): 295 (M+H)$^+$; retention time: 0.72 min.

$^1$H NMR (400 MHz, CHLOROFORM-d) δ ppm: 1.36 (t, J=7.5 Hz, 3H), 1.57-1.62 (m, 2H), 1.95-2.00 (m, 2H), 2.05 (s, 2H), 4.04 (s, 4H), 8.13 (d, J=2.20 Hz, 1H), 8.87 (d, J=2.20 Hz, 1H).

Example I-3

Preparation of 5-(1-cyanocyclopropyl)-3-ethylsulfonyl-pyridine-2-carboxylic Acid

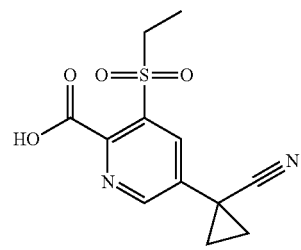 [SMILES: CCS(=O)(=O)c1cc(C2(C#N)CC2)cnc1C(=O)O]

A solution of methyl 5-(1-cyanocyclopropyl)-3-ethylsulfonyl-pyridine-2-carboxylate (0.27 g, 0.92 mmol) was dissolved in THF (4 mL) and water (1.5 mL) (red solution), and then treated with $LiOH.H_2O$ (0.058 g, 1.4 mmol) The mixture was stirred at ambient temperature for 2 hours by which time LCMS analysis showed reaction completion (only desired product at Rt=0.32, method 1). The THF was evaporated in vacuo and the residue was acidified with 1M HCl and extracted with EtOAc. The organic layer was washed with brine, dried over $Na_2SO_4$ filtrated and concentrated in vacuo to give pure title product as a beige solid.

LCMS (method 1): 281 (M+H)$^+$; retention time: 0.30 min.
$^1$H NMR (400 MHz, methanol-d$_4$) δ ppm: 1.31 (t, J=7.3 Hz, 3H), 1.71-1.78 (m, 2H), 1.92-1.98 (m, 2H), 3.60 (q, J=7.3 Hz, 2H), 8.28 (d, J=2.20 Hz, 1H), 8.83 (d, J=2.20 Hz, 1H).

Example H13: Synthesis of 4-bromo-2-[5-ethylsulfonyl-6-[7-(trifluoromethyl)imidazo[1,2-c]pyrimidin-2-yl]-3-pyridyl]butanenitrile (Compound P13, Table P)

(Compound P13, Table P)

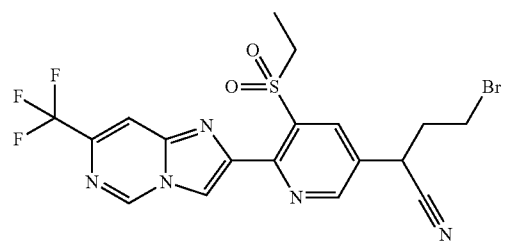

Step A: Synthesis of 2-(6-acetyl-5-ethylsulfonyl-3-pyridyl)acetonitrile

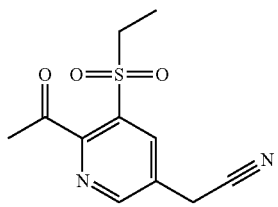 [SMILES: CCS(=O)(=O)c1cc(CC#N)cnc1C(C)=O]

In a vial, 1-(5-chloro-3-ethylsulfonyl-2-pyridyl)ethanone (2 g, 8.0743 mmol) was diluted in dimethylformamide (14.534 mL, 187 mmol). Under argon 2-trimethylsilylacetonitrile (3.38 mL, 24.223 mmol), difluorozinc (0.51098 g, 4.8446 mmol), XANTPHOS (0.191 g, 0.32297 mmol) and PD2(DBA)3 (0.15245 g, 0.16149 mmol) were added. The vial was capped and heated at 140° C. for 45 min in the microwave system. LCMS analysis showed the formation of product. Reaction mixture was diluted with ethylacetate and filtered over hyflo. The mother liquid was washed with NH4Cl/water and brine, dried over Na$_2$SO$_4$, filtered and evaporated. The crude was purified by flash chromatography over silicagel to give the title compound.

LCMS (method 1); Rt=0.64 min, [M+H] 253
$^1$H NMR (400 MHz, CHLOROFORM-d) δ ppm 1.17 (t, J=7.34 Hz, 4H) 2.53 (s, 3H) 3.40 (q, J=7.34 Hz, 2H) 3.74 (s, 2H) 8.15 (d, J=1.83 Hz, 1H) 8.63 (d, J=1.83 Hz, 1H)

Step B: Synthesis of 1-(6-acetyl-5-ethylsulfonyl-3-pyridyl)cyclopropanecarbonitrile (Compound I9, Table I)

(Compound I9, Table I)

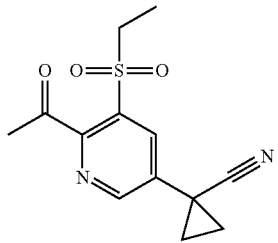

2-(6-acetyl-5-ethylsulfonyl-3-pyridyl)acetonitrile (0.75 g, 2.973 mmol) was dissolved in acetonitrile (22.5 mL, 430 mmol) and dicesium carbonic acid (2.901 g, 8.918 mmol) was added to the colourless solution (solution darkened), followed by the addition of 1,2-dibromoethane (0.523 mL, 5.945 mmol). The resulting mixture was stirred at 80° C. for 3 hours. LCMS analysis showed the formation of product. Reaction mixture was evaporated and the residue was diluted in ethylacetate and water. The aqueous layer was extracted 3 times with ethylacetate. The combined organic layer was washed with water then brine, dried over Na2SO4, filtered and evaporated. The crude was purified by flash over silicagel to give the title compound.

LCMS (method 1); Rt=0.76 min, [M+H] 279
$^1$H NMR (400 MHz, CHLOROFORM-d) δ ppm 1.38 (t, J=7.52 Hz, 3H) 1.60-1.66 (m, 2H) 1.97-2.03 (m, 2H) 2.76 (s, 3H) 3.62 (q, J=7.46 Hz, 2H) 8.12 (d, J=2.20 Hz, 1H) 8.90 (d, J=2.20 Hz, 1H)

Step C: Synthesis of 4-bromo-2-[6-(2-bromoacetyl)-5-ethylsulfonyl-3-pyridyl]butanenitrile

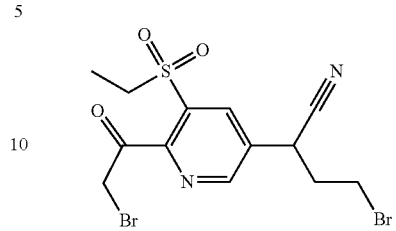

A sample of 1-(6-acetyl-5-ethylsulfonyl-3-pyridyl)cyclopropanecarbonitrile (0.34 g, 1.222 mmol), dibromocopper (0.5457 g, 2.443 mmol), acetonitrile (1.19 mL) and chloroform (1.19 mL) were mixed together and the resulting mixture was stirred 55' at 140° C. in the microwave. LCMS showed the formation of product. The reaction mixture was evaporated under vacuum and the residue obtained was dissolved in dichloromethane, NaHCO$_3$. and NH$_4$OH 1 N. The aqueous layer was extracted 3 times with dichloromethane. The combined organic layers was dried over Na2SO4, filtered and evaporated under vacuum. The crude was purified by flash chromatography over silicagel and then on reverse phase to give the title compound.

LCMS (method 1); Rt=0.94 min, [M+H] 504 $^1$H NMR (400 MHz, CHLOROFORM-d) δ ppm 1.41 (t, J=7.34 Hz, 3H) 2.38-2.49 (m, 1H) 2.59-2.70 (m, 1H) 3.51 (ddd, J=10.91, 5.96, 4.77 Hz, 1H) 3.61-3.73 (m, 3H) 4.46 (dd, J=9.17, 6.24 Hz, 1H) 8.46 (d, J=2.20 Hz, 1H) 8.92 (d, J=2.20 Hz, 1H)

Step D: Synthesis of 4-bromo-2-[5-ethylsulfonyl-6-[7-(trifluoromethyl)imidazo[1,2-c]pyrimidin-2-yl]-3-pyridyl] butanenitrile (Compound P 13, Table P)

(Compound P13, Table P)

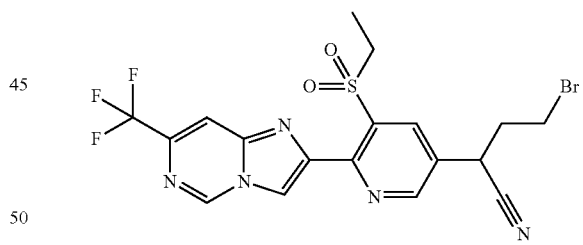

A sample of 4-bromo-2-[6-(2-bromoacetyl)-5-ethylsulfonyl-3-pyridyl]butanenitrile (0.085 g, 0.1940 mmol) and 6-(trifluoromethyl)pyrimidin-4-amine (0.03262 g, 0.1940 mmol) were dissolved in acetonitrile (0.85 mL, 16.3 mmol) and the resulting mixture was stirred 1 hour at 150° C. in a microwave. LCMS analysis showed the formation of product. The reaction mixture was evaporated under vacuum and the crude was purified by flash chromatography over silicagel and then on reverse phase to give the title compound.

LCMS (method 1); Rt=0.93 min, [M+H] 438
$^1$H NMR (400 MHz, CHLOROFORM-d) δ ppm 1.44 (t, J=7.52 Hz, 3H) 2.42-2.53 (m, 1H) 2.61-2.72 (m, 1H) 3.48-3.56 (m, 1H) 3.64-3.74 (m, 1H) 4.05 (dd, J=7.52, 5.32 Hz, 2H) 4.45 (dd, J=8.80, 6.60 Hz, 1H) 8.01 (s, 1H) 8.42 (s, 1H) 8.58 (d, J=2.57 Hz, 1H) 8.98 (d, J=2.20 Hz, 1H) 9.22 (s, 1H)

Preferred compositions are composed in particular as follows (%=percent by weight):

Emulsifiable concentrates:
active ingredient: 1 to 95%, preferably 5 to 20%
surfactant: 1 to 30%, preferably 10 to 20%
solvent: 5 to 98%, preferably 70 to 85%

Dusts:
active ingredient: 0.1 to 10%, preferably 0.1 to 1%
solid carrier: 99.9 to 90%, preferably 99.9 to 99%

Suspension concentrates:
active ingredient: 5 to 75%, preferably 10 to 50%
water: 94 to 24%, preferably 88 to 30%
surfactant: 1 to 40%, preferably 2 to 30%

Wettable powders:
active ingredient: 0.5 to 90%, preferably 1 to 80%
surfactant: 0.5 to 20%, preferably 1 to 15%
solid carrier: 5 to 99%, preferably 15 to 98%

Granulates:
active ingredient: 0.5 to 30%, preferably 3 to 15%
solid carrier: 99.5 to 70%, preferably 97 to 85%

PREPARATORY EXAMPLES

"Mp" means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated.

LCMS Methods:
Method 1:
Spectra were recorded on a Mass Spectrometer from Waters (SQD, SQDII or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 mm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 1.2 min; Flow (ml/min) 0.85

Method 2—Standard Long:
Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 □m, 30×2.1 mm, Temp: 60° C., DAD wavelength range (nm): 210 to 500, Solvent Gradient: A=water+5% MeOH+0.05% HCOOH, B=acetonitrile+0.05% HCOOH: gradient: gradient: 0 min 0% B, 100% A; 2.7-3.0 min 100% B; Flow (ml/min) 0.85

ESI MS Method
Mass Spectroscopy Method MS
LC-20AD Mass Spectrometer from Shimadzu (Single quadrupole mass spectrometer)
Instrument Parameters:
Ionisation method: Electrospray
Polarity: positive and negative ions
Capillary (kV) 1.50
Cone (V) unknown
Extractor (V) 5.00
Source Temperature (° C.) 200
Desolvation Temperature (° C.) 250
Cone gas Flow (l/Hr) 90
Desolvation gas Flow (l/Hr) 90
Mass range: 50 to 1000 Da

TABLE P1

Examples of compounds of formula (I):

| Compound No. | Compound | Melting Point °C. | LCMS/NMR |
|---|---|---|---|
| P1 | | — | LCMS (method 1): 425/427 (M + H)$^+$ R$_t$ = 1.05 min |
| P2 | | 179-180 | LCMS (method 1): 500(M + H)$^+$ Rt = 1.13 min |

TABLE P1-continued

Examples of compounds of formula (I):

| Compound No. | Compound | Melting Point °C. | LCMS/NMR |
|---|---|---|---|
| P3 | | 225-226 | LCMS (method 1): 466/468(M + H)+ R_t = 1.12 min |
| P4 | | 229-230 | LCMS (method 1): 491(M + H)+ 1.01 min |
| P5 | | 185-187 | LCMS (method 1): 467/469 (M + H)+ 1.07 min |
| P6 | | 230-232 | LCMS (method 1): 501(M + H)+ 1.08 min |
| P7 | | 174-176 | LCMS (method 1): 383 (M + H)+ 0.88 min |
| P8 | | — | LCMS (method 1): 422(M + H)+ 0.89 min |
| P9 | | 210-211 | LCMS (method 1): 479(M + H)+ 1.08 min |

TABLE P1-continued
Examples of compounds of formula (I):
| Compound No. | Compound | Melting Point °C. | LCMS/NMR |
|---|---|---|---|
| P10 | 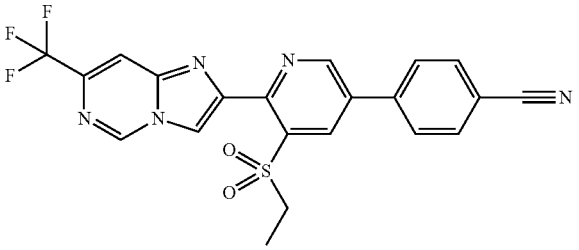 [SMILES: CCS(=O)(=O)c1cc(-c2ccc(C#N)cc2)cnc1-c1cn2cnc(C(F)(F)F)cc2n1] | 279-281 | LCMS (method 1): 458(M + H)+ 0.98 min |
| P11 | 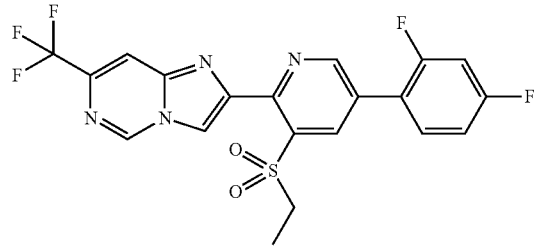 [SMILES: CCS(=O)(=O)c1cc(-c2ccc(F)cc2F)cnc1-c1cn2cnc(C(F)(F)F)cc2n1] | 205-208 | LCMS (method 1): 469(M + H)+ 1.05 min |
| P12 | 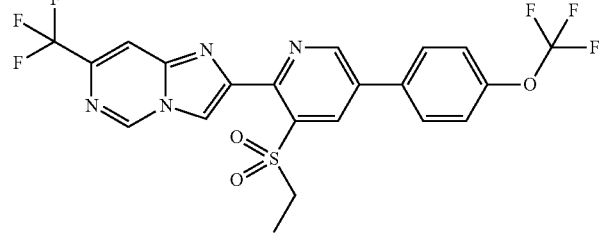 | 214-215 | LCMS (method 1): 517(M + H)+ 1.12 min |
| P13 | 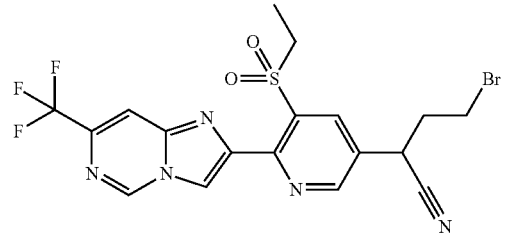 [SMILES: CCS(=O)(=O)c1cc(C(C#N)CCBr)cnc1-c1cn2cnc(C(F)(F)F)cc2n1] | 93-95 | LCMS (method 1): 502/504(M + H)+ 0.95 min |
| P14 | 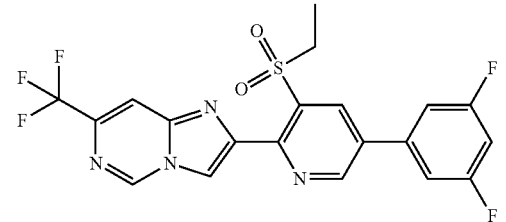 [SMILES: CCS(=O)(=O)c1cc(-c2cc(F)cc(F)c2)cnc1-c1cn2cnc(C(F)(F)F)cc2n1] | 249-250 | LCMS (method 1): 469(M + H)+ 1.10 min |
| P15 | 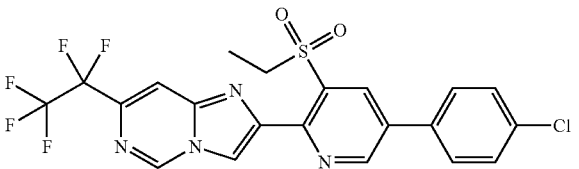 [SMILES: CCS(=O)(=O)c1cc(-c2ccc(Cl)cc2)cnc1-c1cn2cnc(C(F)(F)C(F)(F)F)cc2n1] | 223-225 | LCMS (method 1): 517 (M + H)+ 1.17 min |

TABLE P1-continued

Examples of compounds of formula (I):

| Compound No. | Compound | Melting Point °C. | LCMS/NMR |
|---|---|---|---|
| P16 | | 186-188 | LCMS (method 1): 397 (M + H)+ 1.44 min |
| P17 | | 202-204 | LCMS (method 1): 534 (M + H)+ 1.05 min.- |
| P18 | | 215-217 | LCMS (method 1): 523 (M + H)+ $R_t$ = 0.94 min |
| P19 | | 216-217 | LCMS (method 1): 485 (M + H)+ $R_t$ = 0.96 min |
| P20 | | 180-181 | LCMS (method 1): 485 (M + H)+ $R_t$ = 0.96 min - |
| P21 | | 220-221 | LCMS (method 1): 551 (M + H)+ $R_t$ = 1.12 min - |
| P22 | | 229-231 | LCMS (method 1): 501 (M + H)+ $R_t$ = 1.05 min - |

TABLE P1-continued

Examples of compounds of formula (I):

| Compound No. | Compound | Melting Point °C. | LCMS/NMR |
|---|---|---|---|
| P23 | | — | LCMS (method 1): 501/503 (M + H)⁺ $R_t$ = 1.24 min |
| P24 | | | LCMS (method 1): 451 (M + H)⁺ $R_t$ = 1.13 min |
| P25 | | | LCMS (method 1): 467/469 (M + H)⁺ $R_t$ = 1.16 min |
| P26 | | >250 | $^1$H NMR (400 Mz, DMSO-d$_6$) δ: 1.30 (t, 3H), 4.19 (q, 2H), 8.27 (s, 1H), 8.36 (d, 2H), 8.69(s, 1H), 9.01 (s, 1H), 9.60(d, 2H); $^{19}$F-NMR (300 Mz, DMSO-d$_6$) δ: −37.41 (s, 3F); ESI-MS(−): 570(M + Cl); |
| P27 | | >250 | $^1$H NMR (400 Mz, CDCl$_3$) δ(ppm): 9.578 (br, 1 H), 9.1 (br, 2 H), 8.973 (d, J = 4.4 Hz, 1 H), 8.398 (br, 1 H), 8.062 (s, 1 H), 7.92 (br, 1 H), 7.589 (d, J = 5.2 Hz, 1H), 3.975(m, 2 H), 1.628 (br, 3 H). $^{19}$F (400 Mz, CDCl$_3$) δ (ppm): −39.4 (s, 3 H), −63.7(s, 3 H). ESI-MS(H⁺): 534. |
| P28 | | 211-214 | $^1$H NMR (400 MHz, CDCl$_3$) δ: 9.29-2.28 (m, 1 H), 9.07 (s, 1 H), 8.70 (d, J = 2.4 Hz, 1 H), 8.32 (s, 1 H), 8.03 (d, J = 2.4 Hz, 1 H), 7.90 (s, 1 H), 6.53 (d, J = 2.0 Hz, 1 H), 3.98 (q, J = 7.6 Hz, 2 H), 1.38 (t, J = 7.6 Hz, 3H). ESI-MS: 489 (M + H)⁺. $^{19}$F NMR (300 MHz, d$_6$-DMSO) δ −38.55 (s, 3F). |

TABLE P1-continued

Examples of compounds of formula (I):

| Compound No. | Compound | Melting Point °C. | LCMS/NMR |
|---|---|---|---|
| P29 | (structure) | — | LCMS(method 1): 493 (M + H)+ Rt = 1.24 min |
| P30 | (structure) | — | LCMS (method 1): 396 (M + H)+ Rt = 0.81 min |

All other compounds listed in tables 1-6 can be prepared by analogous methods to those described here in the experimental section, and using methods known to those skilled in the art.

Table of Intermediates:

| Compound No. | Compound | Melting Point °C. | LCMS/NMR |
|---|---|---|---|
| I-1 | (structure) | 227-229 | LCMS (method 1): 391 (M + H)+ 0.94 min |
| I-2 | (structure) | 195-197 | LCMS (method 1): 401/4023/405 (M + H)+ 0.88 min |
| I-3 | (structure) | 228-229 | LCMS (method 1): 485/487 (M + H)+ 0.99 min |
| I-4 | (structure) | 170-171 | LCMS (method 1): 475(M + H)+ 1.02 min |

Table of Intermediates:

| Compound No. | Compound | Melting Point °C. | LCMS/NMR |
|---|---|---|---|
| I-5 | [structure: trifluoromethylthio-imidazo-pyrimidine linked to bromopyridine with ethylsulfonyl] | 159-160 | LCMS (method 1): 481/484(M + H)+ 0.98 min |
| I-6 | [structure: 4-amino-6-(trifluoromethylthio)pyrimidine] | — | $^1$H-NMR (400 Mz, DMSO-d$_6$) δ: 6.60 (s, 1H), 7.26 (s, 2H), 8.29 (s, 1H). $^{19}$F-NMR (300 Mz, DMSO-d$_6$) δ: −42.45 (s, 3F). |
| I-7 | [structure: 4-amino-6-(1,1,2,2,2-pentafluoroethyl)pyrimidine] | — | $^1$H-NMR (400 Mz, DMSO-d$_6$) δ (ppm): 6.80 (s, 1 H), 7.50 (s, 2 H), 8.47 (s, 1 H). $^{19}$F-NMR (300 Mz, DMSO-d$_6$) δ: −79.41 (s, 3 F), −116.10 (s, 2 F); ESI-MS(+): 214(M + 1), ESI-MS(−): 212(M − 1). |
| I-8 | [structure: methyl 3-(ethylsulfonyl)-5-(1-cyanocyclopropyl)picolinate] | | LCMS (method 1): 295 (M + H)+ 0.72 min |
| I-9 | [structure: 1-(3-(ethylsulfonyl)-5-(1-cyanocyclopropyl)pyridin-2-yl)ethanone] | | LCMS (method 1): 279 (M + H)+ 0.76 min |

Formulation Examples (%=Percent by Weight)

Example F1: Emulsion concentrates

| | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2: Solutions

| | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3: Granules

|  | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4: Dusts

|  | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

Example F5: Wettable powders

|  | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutyl-naphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6: Extruder granules

| Active ingredient | 10% |
|---|---|
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7: Coated granules

| Active ingredient | 3% |
|---|---|
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8: Suspension concentrate

| Active ingredient | 40% |
|---|---|
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

Example F9: Powders for dry seed treatment

|  | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

Example F10: Emulsifiable concentrate

| active ingredient | 10% |
|---|---|
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

Example F11: Flowable concentrate for seed treatment

| active ingredients | 40% |
|---|---|
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1 to 6 of the present invention"):

an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No. 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinacti (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TXTX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis (dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone

[CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure B₁ (839)+TX, trimedlure B₂ (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, *Bacillus thuringiensis* delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No. 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin [CCN]+TX, jasmolin I (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metoflu-thrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+

TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, copperpersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl] methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX; and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain I-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, Chromobacterium subtsugae strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo*-miniatus+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, *Enterobacteriaceae*+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, *Granulovirus* (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone-formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX,

*Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum* rifai (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670 30 TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibacillus marismortui*+TX, *Xanthomonas campestris* pv. Poae (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near ambrosioides (Requiem®)+TX, *Chrysanthemum* extract (Crisant®)+TX, extract of neem oil (Trilogy®)+TX, essentials oils of *Labiatae* (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, *Pedaliaceae* oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, *Rutaceae* plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove peppermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX,Z)-3+TX,8+TX,11 Tetradecatrienyl acetate+TX, (Z+TX,Z+TX, E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (Aphelinus-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius califomicus* (Amblyline®+TX, Spical®)+TX, *Amblyseius cucumeris* (Thripex®+TX, Bugline Cucumeris®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cepha/onomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Dephastus catalinae* (Delphastus®)+TX, *Dephastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (Dac-Digline®+TX, Minex®)+TX, *Diversinervus* spp.+TX, *Encarsia citrina*+TX, *Encarsia formosa* (Encarsia Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline E®)+TX, *Eretmocerus eremicus* (Bemimix®)+TX, *Eretmocerus hayati*+TX, *Eretmocerus mundus* (Bemipar®+TX, Eretline M®)+TX, *Eretmocerus siphonini*+TX, *Exochomus quadripustulatus*+TX, *Feltiella acarisuga* (Spidend®)+TX,

*Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (Harmo-Beetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline Hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline M®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline C®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline I®)+TX, *Orius laevigatus* (Thripor-L®+TX, Oriline I®)+TX, *Orius majusculus* (Oriline M®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline P®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, Steinemema carpocapsae (Nematac C®+TX, Millenium®+TX, BioNem C®+TX, NemAttack®+TX, Nemastar®+TX, Capsanem®)+TX, *Steinemema feltiae* (NemaShield®+TX, Nemasys F®+TX, BioNem F®+TX, Steinernema-System®+TX, NemAttack®+TX, Nemaplus®+TX, Exhibitline Sf®+TX, Scia-Rid®+TX, Entonem®)+TX, *Steinemema kraussei* (Nemasys L®+TX, BioNem L®+TX, Exhibitline Srb®)+TX, Steinemema riobrave (BioVector®+TX, BioVektor®)+TX, *Steinemema scapterisci* (Nematac S®)+TX, *Steinemema* spp.+TX, *Steinemematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine B®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline D®)+TX, *Erwinia amylovora* (Harpin) (ProAct®+TX, Ni-HIBIT Gold CST®)+TX, Ferri-phosphate (Ferramol®)+TX, Funnel traps (Trapline Y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline F®)+TX, *Microctonus hyperodae*+TX, *Myco/eptodiscus terrestris* (Des-X®)+TX, BioGain®+TX, Aminomite®+TX, Zenox®+TX, Pheromone trap (Thripline Ams®)+TX, potassium bicarbonate (MilStop®)+TX, potassium salts of fatty acids (Sanova®)+TX, potassium silicate solution (SD-Matrix®)+TX, potassium iodide+potassium-thiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+B®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood-.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Tables 1 to 6 with active ingredients described above comprises a compound selected from Tables 1 to 6 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1 to 6 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 6 and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

Example B1: *Bemisia tabaci* (Cotton White Fly)

Cotton leaf discs were placed on agar in 24-well microtiter plates and sprayed with aqueous test solutions prepared from 10,000 ppm DMSO stock solutions. After drying the leaf discs were infested with adult white flies. The samples were checked for mortality 6 days after incubation.

The following compounds resulted in at least 80% mortality at an application rate of 200 ppm: P10, P13, P15 and P4.

Example B2: *Diabrotica balteata* (Corn Root Worm)

Maize sprouts placed onto an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm:
P8, P9, P10, P11, P12, P13, P30, P14, P15, P16, P6, P5, P4, P1, P3 and P2.

Example B3: *Diabrotica balteata* (Corn Root Worm)

Maize sprouts placed onto an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality 4 days after infestation.

The following compounds resulted in at least 80% mortality at an application rate of 200 ppm: P8, P9, P10, P11, P12, P13, P30, P14, P16, P6, P5, P4, P1, P3 and P2.

Example B4: *Euschistus heros* (Neotropical Brown Stink Bug)

Soybean leaves on agar in 24-well microtiter plates were sprayed with aqueous test solutions prepared from 10,000 ppm DMSO stock solutions. After drying the leaves were infested with N2 nymphs. The samples were assessed for growth inhibition in comparison to untreated samples 5 days after infestation. Control of *Euschistus heros* by a test sample is given when the growth inhibition is higher than the untreated sample.

The following compounds resulted in at least 80% growth inhibition at an application rate of 200 ppm: P8 and P5.

Example B5: *Euschistus heros* (Neotropical Brown Stink Bug)

Soybean leaves on agar in 24-well microtiter plates were sprayed with aqueous test solutions prepared from 10,000 ppm DMSO stock solutions. After drying the leaves were infested with N2 nymphs. The samples were assessed for mortality 5 days after infestation.

The following compounds resulted in at least 80% mortality at an application rate of 200 ppm:
P8, P9, P11, P12, P13, P30, P14, P15, P16, P6, P5, P4 and P1.

Example B6: *Euschistus heros* (Neotropical Brown Stink Bug)

Soybean leaves on agar in 24-well microtiter plates were sprayed with aqueous test solutions prepared from 10,000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm:
P8, P9, P11, P12, P13, P30, P14, P15, P16, P6, P5, P4 and P1.

Example B7: *Frankliniella occidentalis* (Western Flower Thrips)

Sunflower leaf discs were placed on agar in 24-well microtiter plates and sprayed with aqueous test solutions prepared from 10,000 DMSO stock solutions. After drying the leaf discs were infested with a Frankliniella population of mixed ages. The samples were assessed for mortality 7 days after infestation.

The following compounds resulted in at least 80% mortality at an application rate of 200 ppm:
P10, P11, P13, P15, P16 and P5.

Example B8: *Myzus persicae* (Green Peach Aphid)

Sunflower leaf discs were placed onto agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm: P8, P11, P13, P14, P16 and P1.

Example B9: *Myzus persicae* (Green Peach Aphid)

Roots of pea seedlings infested with an aphid population of mixed ages were placed directly into aqueous test solutions prepared from 10,000 DMSO stock solutions. The samples were assessed for mortality 6 days after placing seedlings into test solutions.

The following compounds resulted in at least 80% mortality at a test rate of 24 ppm: P30

Example B10: *Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for growth inhibition in comparison to untreated samples 5 days after infestation. Control of *Plutella xylostella* by a test sample is given when the growth inhibition is higher than the untreated sample.

The following compounds resulted in at least 80% growth inhibition at an application rate of 200 ppm: P8, P9, P13, P30, P14, P16 and P1.

Example B12: *Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality 5 days after infestation.

The following compounds resulted in at least 80% mortality at an application rate of 200 ppm:
P8, P9, P10, P11, P12, P13, P14, P15, P16, P6, P5, P4, P1 and P2.

Example B13: *Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:
P8, P9, P10, P11, P12, P13, P30, P14, P15, P16, P6, P5, P4, P1 and P2.

Example B14: *Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for anti-feeding effect in comparison to untreated samples 3 days after infestation. Control of *Spodoptera littoralis* by a test sample is given when the anti-feedant effect is higher than the untreated sample.

The following compounds resulted in at least 80% control at an application rate of 200 ppm:
P8, P9, P10, P11, P12, P13, P14, P15, P16, P6, P5, P4, P1, P3 and P2.

Example B15: *Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for growth inhibition in comparison to untreated samples 3 days after infestation. Control of *Spodoptera littoralis* by a test sample is given when the growth inhibition is higher than the untreated sample.

The following compounds resulted in at least 80% control at an application rate of 200 ppm:
P8, P9, P10 and P16.

Example B16: *Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality 3 days after infestation.

The following compounds resulted in at least 80% mortality at an application rate of 200 ppm: P8, P9, P10, P11, P12, P13, P14, P15, P16, P6, P5, P4, P1, P3 and P2.

Example B17: *Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm:
P8, P9, P10, P11, P12, P13, P14, P15, P16, P6, P5, P4, P1, P3 and P2.

Example B18: *Spodoptera littoralis* (Egyptian Cotton Leaf Worm)

Test compounds were applied by pipette from 10,000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compounds gave an effect of at least 80% in at least one of the three categories (mortality, anti-feeding, or growth inhibition) at a test rate of 12.5 ppm:
P11, P12, P13, P14, P15, P6, P5, P4 and P1.

Example B19: *Spodoptera littoralis* (Egyptian Cotton Leaf Worm)

Test compounds were applied by pipette prepared from 10,000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for anti-feedant effect in comparison to untreated samples 6 days after infestation.

The following compounds gave an effect of at least 80% anti-feeding at a test rate of 12.5 ppm:
P11, P12, P13, P14, P15, P6, P5, P4 and P1.

Example B20: *Spodoptera littoralis* (Egyptian Cotton Leaf Worm)

Test compounds were applied by pipette prepared from 10,000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate.

*Spodoptera* eggs were pipetted through a plastic stencil onto a humid gel blotting paper and the lid plate was closed with it. The samples were assessed for mortality 6 days after infestation.

The following compounds gave an effect of at least 80% mortality at a test rate of 12.5 ppm:
P11, P12, P13, P14, P15, P6, P5, P4 and P1.

Example B21: *Tetranychus urticae* (Two-Spotted Spider Mite)

Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm:
P13 and P14.

Example B22: Thrips tabaci (Onion Thrips)

Sunflower leaf discs were placed on agar in 24-well microtiter plates and sprayed with aqueous test solutions prepared from 10,000 ppm DMSO stock solutions. After drying the leaf discs were infested with a thrips population of mixed ages. The samples were assessed for mortality 6 days after infestation.

The following compound resulted in at least 80% mortality at an application rate of 200 ppm:
P13.

Example B23: *Aedes aegypti* (Yellow Fever Mosquito)

Test solutions, at an application rate of 200 ppm in ethanol, were applied to 12 well tissue culture plates. Once the deposits were dry, five, two to five day old adult female *Aedes aegypti* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Aedes aegypti* after 48 h and/or 24 h:
P9, P12, P13, P14, P16, P6, P4, P1 and P2.

Example B24: *Anopheles stephensi* (Indian Malaria Mosquito)

Test solutions, at an application rate of 200 ppm in ethanol, were applied to 12 well tissue culture plates. Once the deposits were dry, five, two to five day old adult female *Anopheles stephensi* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Anopheles stephensi* after 48 h and/or 24 h: P13, P14, P16, P6, P4 and P1.

The invention claimed is:
1. A compound of formula I,

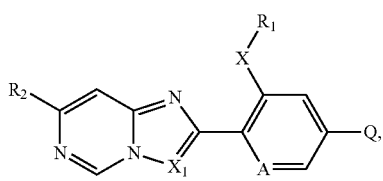

(I)

wherein
A is CH or N;
Q is phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or
Q is a five- to ten-membered monocyclic or fused bicyclic ring system linked via a carbon atom to the ring which contains the group A, said ring system can be aromatic, partially saturated or fully saturated and contains 1 to 4 hetero atoms selected from the group consisting of nitrogen, oxygen and sulfur,
with the proviso that each ring system cannot contain more than 2 oxygen atoms and more than 2 sulfur atoms, said five- to ten-membered ring system can be mono- to polysubstituted by substituents independently selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or
Q is a five- to six-membered, aromatic, partially saturated or fully saturated ring system linked via a nitrogen atom to the ring which contains the group A, said ring system can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; and said ring system contains 1, 2 or 3 heteroatoms selected from the group consisting of nitrogen, oxygen and sulfur, with the proviso that said ring system cannot contain more than one oxygen atom and more than one sulfur atom;
or Q is $C_3$-$C_6$cycloalkyl, or $C_3$-$C_6$cycloalkyl mono- or polysubstituted by substituents selected from the group consisting of halogen, cyano, hydroxycarbonyl, amidocarbonyl, $C_1$-$C_4$alkyl, $C_1$-$C_4$haloalkyl, $C_3$-$C_6$cycloalkyl, and phenyl, whereby the phenyl group can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl;
or Q is $C_2$-$C_6$alkenyl, or $C_2$-$C_6$alkenyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, whereby said phenyl group can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl;
or Q is $C_2$-$C_6$alkynyl, or $C_2$-$C_6$alkynyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, whereby said phenyl group can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$halo-alkylsulfanyl, $C_1$-$C_4$haloalkylsulfinyl, $C_1$-$C_4$haloalkylsulfonyl and —C(O)$C_1$-$C_4$haloalkyl;
or Q is a $C_1$-$C_4$alkyl, which can be mono- or polysubstituted by substituents selected from the group of halogen, cyano, $C_3$-$C_6$cycloalkyl, $C_1$-$C_4$haloalkoxy, $C_1$-$C_4$alkoxy, $C_1$-$C_4$sulfanyl, $C_1$-$C_4$alkylsulfinyl, $C_1$-sulfonyl and —C(O)$C_1$-$C_4$alkyl;
X is S, SO or $SO_2$;
$R_1$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl; or
$R_1$ is $C_3$-$C_6$cycloalkyl mono- or polysubstituted by substituents selected from the group consisting of halogen, cyano and $C_1$-$C_4$alkyl; or $R_1$ is $C_2$-$C_6$alkenyl, $C_2$-$C_6$haloalkenyl or $C_2$-$C_6$alkynyl;
$R_2$ is halogen, cyano, $C_1$-$C_6$haloalkyl or $C_1$-$C_6$haloalkyl substituted by one or two substituents selected from the group consisting of hydroxyl, methoxy and cyano; or
$R_2$ is $C_1$-$C_4$haloalkylsulfanyl, $C_1$-$C_4$haloalkylsulfinyl, $C_1$-$C_4$haloalkylsulfonyl, O($C_1$-$C_4$haloalkyl), or —C(O)$C_1$-$C_4$haloalkyl; or R₂ is C₃-C₆cycloalkyl which can be mono- or polysubstituted by substituents selected from the group consisting of halogen, cyano and C₁-C₄alkyl;

X₁ is CR₃, wherein R₃ is hydrogen, C₁-C₄alkyl, C₂-C₆alkenyl, C₂-C₆alkynyl, C₁-C₄alkoxy-C₁-C₄alkyl or C₃-C₆cycloalkyl;

and agrochemically acceptable salts, stereoisomers, enantiomers, tautomers and N-oxides of those compounds.

2. A compound of formula I according to claim 1, wherein Q is selected from the group consisting of pyrrolyl, pyrazolyl, isoxazolyl, furanyl, thienyl, imidazolyl, oxazolyl, thiazolyl, isothiazolyl, triazolyl, oxadiazolyl, thiadiazolyl, tetrazolyl, furyl, pyridyl, pyrimidyl, pyrazinyl, pyridazinyl, triazinyl, pyranyl, quinazolinyl, isoquinolinyl, indolizinyl, isobenzofuranylnaphthyridinyl, quinoxalinyl, cinnolinyl, phthalazinyl, benzothiazolyl, benzoxazolyl, benzotriazolyl, indazolyl, indolyl, (1H-pyrrol-1-yl)-, (1H-pyrrol-2-yl)-, (1H-pyrrol-3-yl)-, (1H-pyrazol-1-yl)-, (1H-pyrazol-3-yl)-, (3H-pyrazol-3-yl)-, (1H-pyrazol-4-yl)-, (3-isoxazolyl)-, (5-isoxazolyl)-, (2-furanyl)-, (3-furanyl)-, (2-thienyl)-, (3-thienyl)-, (1H-imidazol-2-yl)-, (1H-imidazol-4-yl)-, (1H-imidazol-5-yl)-, (2-oxazol-2-yl)-, (oxazol-4-yl)-, (oxazol-5-yl)-, (thiazol-2-yl)-, (thiazol-4-yl)-, (thiazol-5-yl)-, (isothiazol-3-yl)-, (isothiazol-5-yl)-, (1H-1,2,3-triazol-1-yl)-, (1H-1,2,4-triazol-3-yl)-, (4H-1,2,4-triazol-4-yl)-, (1H-1,2,4-triazol-1-yl)-(1,2,3-oxadiazol-2-yl)-, (1,2,4-oxadiazol-3-yl)-, (1,2,4-oxadiazol-4-yl)-, (1,2,4-oxadiazol-5-yl)-, (1,2,3-thiadiazol-2-yl)-, (1,2,4-thiadiazol-3-yl)-, (1,2,4-thiadiazol-4-yl)-, (1,3,4-thiadiazol-5-yl)-, (1H-tetrazol-1-yl)-, (1H-tetrazol-5-yl)-, (2H-tetrazol-5-yl)-, (2-pyridyl)-, (3-pyridyl)-, (4-pyridyl)-, (2-pyrimidinyl)-, (4-pyrimidinyl)-, (5-pyrimidinyl)-, (2-pyrazinyl)-, (3-pyridazinyl)-, (4-pyridazinyl)-, (1,3,5-triazin-2-yl)-, (1,2,4-triazin-5-yl)-, (1,2,4-triazin-6-yl)-, (1,2,4-triazin-3-yl)-, (furazan-3-yl)-, (2-quinolinyl)-, (3-quinolinyl)-, (4-quinolinyl)-, (5-quinolinyl)-, (6-quinolinyl)-, (3-isoquinolnyl)-, (4-isoquinolnyl)-, (2-quinozolinyl)-, (2-quinoxalinyl)-, (5-quinoxalinyl)-, (pyrido[2,3-b]pyrazin-7-yl)-, (benzoxazol-5-yl)-, (benzothiazol-5-yl)-, (benzo[b]thien-2-yl)- and (benzo[1,2,5]oxadiazol-5-yl)-, indolinyl and tetrahydroquinolynyl.

3. A compound of formula I according to claim 1, wherein Q is selected from the group consisting of J-1 to J-47:

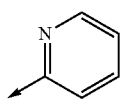

J-1

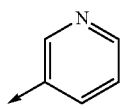

J-2

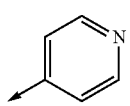

J-3

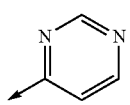

J-4

-continued

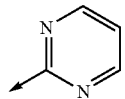

J-5

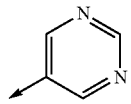

J-6

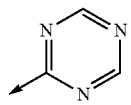

J-7

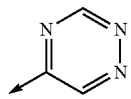

J-8

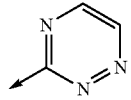

J-9

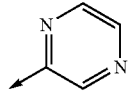

J-10

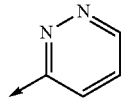

J-11

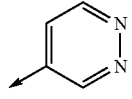

J-12

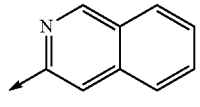

J-13

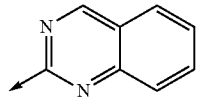

J-14

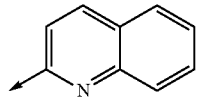

J-15

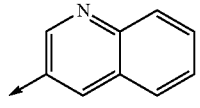

J-16

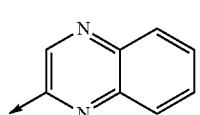

J-17

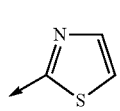

J-18

-continued
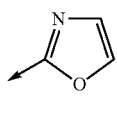
J-19
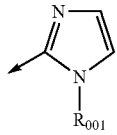
J-20
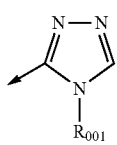
J-21
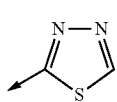
J-22
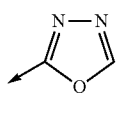
J-23
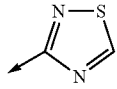
J-24
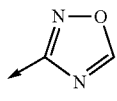
J-25
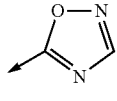
J-26
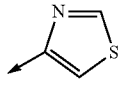
J-27
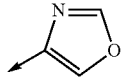
J-28
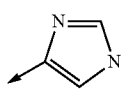
J-29
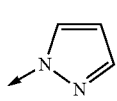
J-30
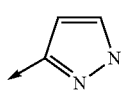
J-31
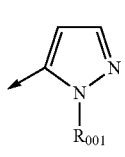
J-32
-continued
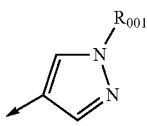
J-33
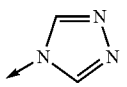
J-34
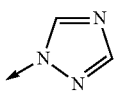
J-35
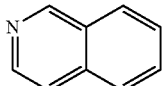
J-36
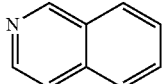
J-37
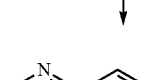
J-38
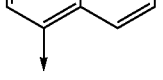
J-39
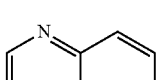
J-40
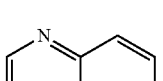
J-41
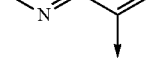
J-42
J-43

-continued

J-44

J-45

J-46

J-47 wherein each group J-1 to J-47 is mono- di- or trisubstituted with Rx, wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl, and $R_{001}$ is hydrogen or $C_1$-$C_2$alkyl.

4. A compound of formula I according to claim 1 represented by the compounds of formula I-1

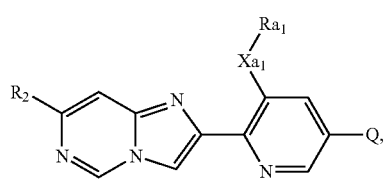
(I-1)

wherein $R_2$ and Q are as defined under formula I in claim 1;

$Xa_1$ is S, SO or $SO_2$; $Ra_1$ is methyl, ethyl, n-propyl, i-propyl or cyclopropylmethyl; and agrochemically acceptable salts, stereoisomers, enantiomers, tautomers and N-oxides of those compounds.

5. A compound of formula I according to claim 1, represented by the compounds of formula I-2

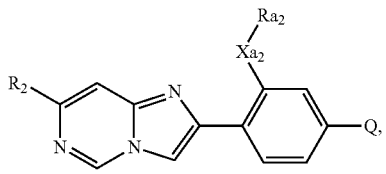
(I-2)

wherein $R_2$ and Q are as defined under formula I in claim 1; and $Xa_2$ is S, SO or $SO_2$; $Ra_2$ is methyl, ethyl, n-propyl, i-propyl or cyclopropylmethyl; and agrochemically acceptable salts, stereoisomers, enantiomers, tautomers and N-oxides of those compounds.

6. A compound of formula I according to claim 1, wherein represented by the compounds of formula Ia-1

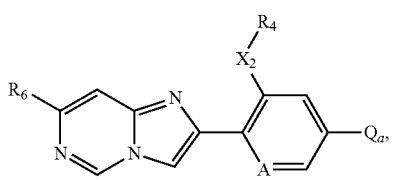
(Ia-1)

wherein
A is CH or N;
$X_2$ is S or $SO_2$;
$R_4$ is $C_1$-$C_4$alkyl;
$R_6$ is $C_1$-$C_4$haloalkyl; and
$Q_a$ is selected from the group consisting of the substituents

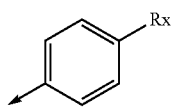
J-0a

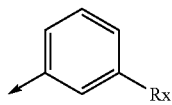
J-0b

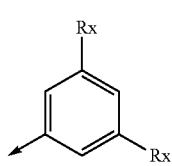
J-0c

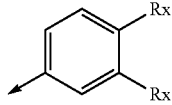
J-0d

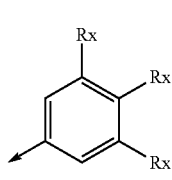
J-0e

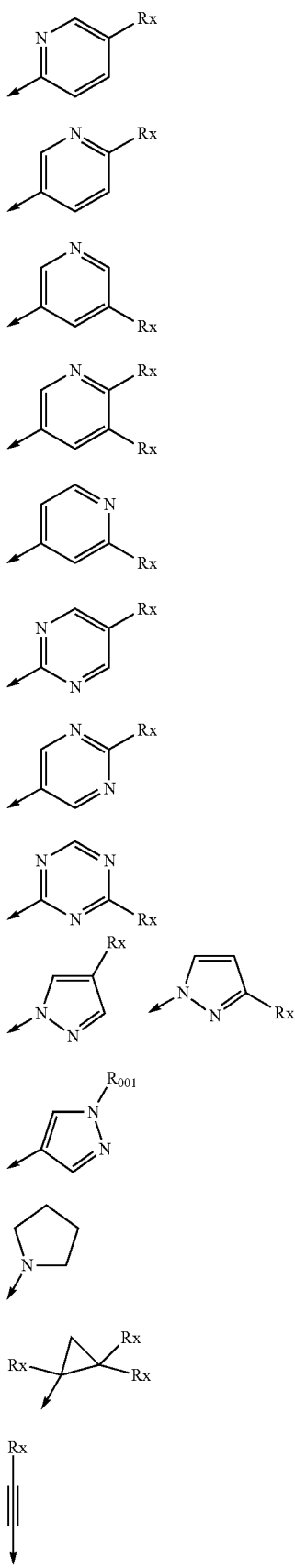
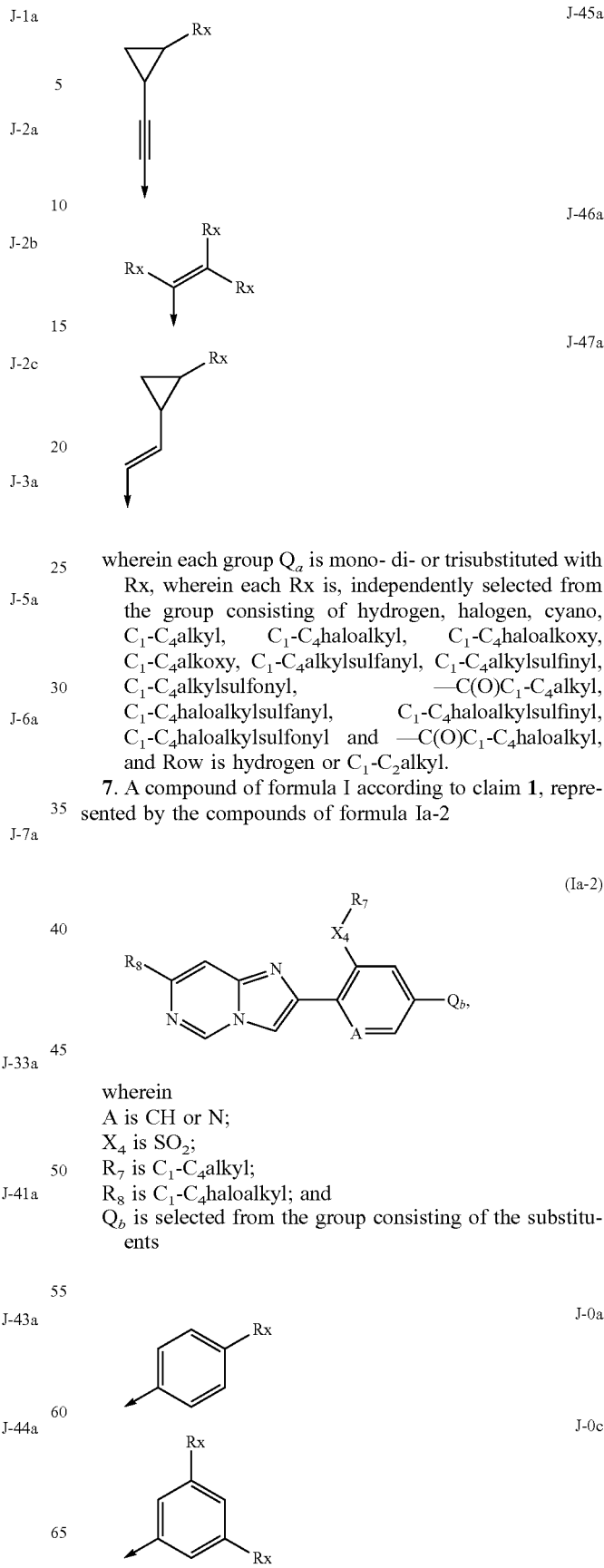

wherein each group $Q_a$ is mono- di- or trisubstituted with Rx, wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl, and Row is hydrogen or $C_1$-$C_2$alkyl.

7. A compound of formula I according to claim 1, represented by the compounds of formula Ia-2 wherein
A is CH or N;
$X_4$ is $SO_2$;
$R_7$ is $C_1$-$C_4$alkyl;
$R_8$ is $C_1$-$C_4$haloalkyl; and
$Q_b$ is selected from the group consisting of the substituents -continued

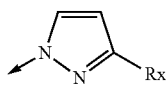
J-30b

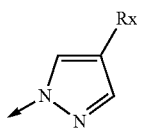
J-30a

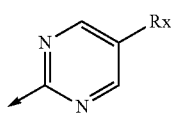
J-5a

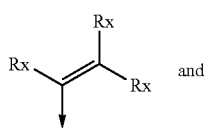
J-44a and

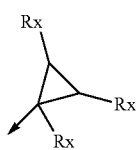
J-43c

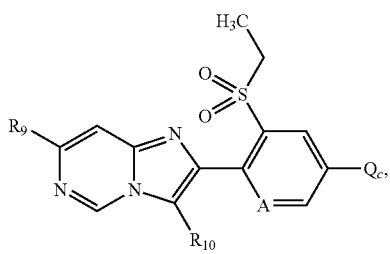

wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

8. A compound of formula I according to claim 1, represented by the compounds of formula Ia-3

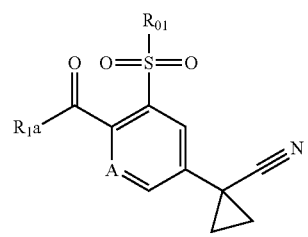
(Ia-3)

wherein
A is CH or N;
$R_9$ is $C_1$-$C_4$haloalkyl;
$R_{10}$ is hydrogen or $C_1$-$C_2$alkyl, and $Q_c$ is selected from the group consisting of the substituents

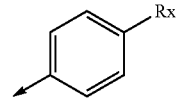
J-0a

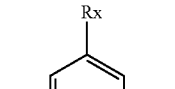
J-0c

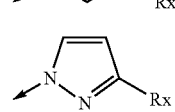
J-30b

J-43c

J-44a

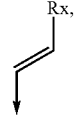
J-46c wherein Rx is selected from the group consisting of hydrogen, halogen, $C_1$-$C_4$alkyl, $C_1$-$C_4$haloalkyl, $C_1$-$C_4$alkoxy and $C_1$-$C_4$haloalkoxy.

9. A compound of formula $Z_0$;

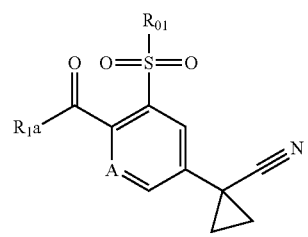
($Z_0$)

wherein $R_{01}$ is $C_1$-$C_4$alkyl, $C_3$-$C_6$cycloalkyl or $C_3$-$C_6$cycloalkyl-$C_1$-$C_4$alkyl;
$R_{1a}$ is $C_1$-$C_4$alkyl, hydroxy, $C_1$-$C_4$alkoxy, or $C_1$-$C_4$haloalkyl; and
A is nitrogen or CH.

10. A method for controlling pests, which comprises a pesticidally effective amount of at least one compound of formula I according to claim 1 or a tautomer thereof, in each case in free form or in agrochemically utilizable salt form, as an active ingredient and at least one auxiliary.

11. A method for controlling pests from the orders: Acarina, Anoplura, Coleoptera, Diptera, Hemiptera, Hymenoptera, Isoptera, Lepidoptera, Mallophaga, Orthoptera, Psocoptera, Siponaptera, Thysanoptera, and Thysanura, which comprises applying a composition according to claim 10 to the pests or their environment with the exception of a method for treatment of the a human or animal body by surgery or therapy and diagnostic methods practiced on the human or animal body.

12. A method for the protection of plant propagation material from attack by pests from the orders: Acarina, Anoplura, Coleoptera, Diptera, Hemiptera, Hymenoptera, Isoptera, Lepidoptera, Mallophaga, Orthoptera, Psocoptera, Siphonaptera, Thysanoptera, and Thysanura, which comprises treating the propagation material or site, where the propagation material is planted, with a composition according to claim 10.

13. Plant propagation material treated in accordance with the method described in claim 12.

* * * * *